(12) United States Patent
Boerjan et al.

(10) Patent No.: US 12,163,138 B2
(45) Date of Patent: Dec. 10, 2024

(54) MUTANT PLANT CINNAMOYL-CoA REDUCTASE PROTEINS

(71) Applicants: VIB VZW, Ghent (BE); UNIVERSITEIT GENT, Ghent (BE)

(72) Inventors: Wout Boerjan, Kalken (BE); Barbara De Meester, Oeselgem (BE); Ruben Vanholme, Destelbergen (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 927 days.

(21) Appl. No.: 16/972,290

(22) PCT Filed: Jun. 6, 2019

(86) PCT No.: PCT/EP2019/064764
§ 371 (c)(1),
(2) Date: Dec. 4, 2020

(87) PCT Pub. No.: WO2019/234141
PCT Pub. Date: Dec. 12, 2019

(65) Prior Publication Data
US 2021/0115462 A1 Apr. 22, 2021

(30) Foreign Application Priority Data
Jun. 6, 2018 (GB) .................................... 1809273

(51) Int. Cl.
*C12N 15/82* (2006.01)
*C12N 9/02* (2006.01)

(52) U.S. Cl.
CPC ....... *C12N 15/8255* (2013.01); *C12N 9/0008* (2013.01); *C12N 15/8262* (2013.01); *C12Y 102/01044* (2013.01)

(58) Field of Classification Search
None
See application file for complete search history.

(56) References Cited

PUBLICATIONS

Tamasloukht, et al. (Journal of experimental botany 62.11 (2011): 3837-3848). (Year: 2011).*
Sattler, Steven A., et al. "Structural and biochemical characterization of cinnamoyl-CoA reductases." Plant physiology 173.2 (2017): 1031-1044. (Year: 2017).*
Barakat, et al. "Comparative and phylogenomic analyses of cinnamoyl-CoA reductase and cinnamoyl-CoA-reductase-like gene family in land plants." Plant Science 181.3 (2011): 249-257. (Year: 2011).*
Chao, Nan, et al. "Characterization of the Cinnamoyl-CoA Reductase (CCR) Gene Family in Populus Tomentosa Reveals the Enzymatic Active Sites and Evolution of CCR." Planta, vol. 245, No. 1, 2017, pp. 61-75.
Leple, Jean-Charles, et al. "Downregulation of Cinnamoyl-Coenzyme A Reductase in Poplar: Multiple-Level Phenotyping Reveals Effects on Cell Wall Polymer Metabolism and Structure." The Plant Cell, vol. 19, No. 11, 2007, pp. 3669-3691.
PCT International Search Report and Written Opinion; Application No. PCT/EP2019/064764, VIB VZW International filing date of Jun. 6, 2019, date of mailing Aug. 7, 2019, 10 pages.
Rinaldi, Roberto, et al. "Paving the Way for Lignin Valorisation: Recent Advances in Bioengineering, Biorefining and Catalysis." Angewandte Chemie (International Ed.), vol. 55, No. 29, 2016, pp. 8164-8215.
Sattler, Steven A., et al. "Structural and Biochemical Characterization of Cinnamoyl-CoA Reductases." Plant Physiology (Bethesda), vol. 173, No. 2, 2017, pp. 1031-1044. document, 2 pages.
Zhou, Rui, et al. "Distinct Cinnamoyl CoA Reductases Involved in Parallel Routes to Lignin in Medicago Truncatula." Proceedings of the National Academy of Sciences—PNAS, vol. 107, No. 41, 2010, pp. 17803-17808.

* cited by examiner

*Primary Examiner* — Charles Logsdon
(74) *Attorney, Agent, or Firm* — Patent Law Works LLP

(57) ABSTRACT

The present invention relates to a mutant plant Cinnamoyl-CoA Reductase (CCR) protein capable of restoring the yield penalty in plants with lignin traits such as ccr-related deficiencies and methods and uses thereof. More specifically, the invention relates to plants lacking functional wild type CCR protein but having a weak ccr allele resulting in lower lignin amounts and increased saccharification, further accompanied by plant growth restoration of the lignin modification-induced dwarfism.

15 Claims, 14 Drawing Sheets
(14 of 14 Drawing Sheet(s) Filed in Color)
Specification includes a Sequence Listing.

Figure 4A
```
>Populus alba CCR2 protein sequence
MPVDASSLSGQGQTICVTGAGGFIASWMVKLLLDKGYTVRGTARNPADPKNSHLRELEGAQERLTLCKADLLDYESLKEAIQGCD
GVFHTASPVTDDPEEMVEPAVNGTKNVIIAAAEAKVRRVVFTSSIGAVYMDPNKGPDVVIDESCWSDLEFCKNTKNWYCYGKAVA
EQAAWDMAKEKGVDLVVVNPVLVLGPLLQPTVNASIVHILKYLTGSAKTYANSVQAYVHVRDVALAHILVFETPSASGRYLCSES
VLHRGEVVEILAKFFPEYPIPTKCSDEKNPRKQPYKFSNQKLRDLGFEFTPVKQCLYETVKSLQERGHLPIPKQAAEESLKIQ >Populus alba ccr2 12 CCR2 protein sequence
MPVDASSLSGQGQTICVTGAGGFIASWMVKLLLDKGYTVRGTARNPADPKNSHLRELEGAQERLTLCKADLLDYESLKEAIQGCD
GVFHTASPVTDDPEEMVEPAVNGTKNVI~TAAEAKVRRVVFTSSIGAVYMDPNKGPDVVIDESCWSDLEFCKNTKNWYCYGKAVA
EQAAWDMAKEKGVDLVVVNPVLVLGPLLQPTVNASIVHILKYLTGSAKTYANSVQAYVHVRDVALAHILVFETPSASGRYLCSES
VLHRGEVVEILAKFFPEYPIPTKCSDEKNPRKQPYKFSNQKLRDLGFEFTPVKQCLYETVKSLQERGHLPIPKQAAEESLKIQ
```

Figure 4B

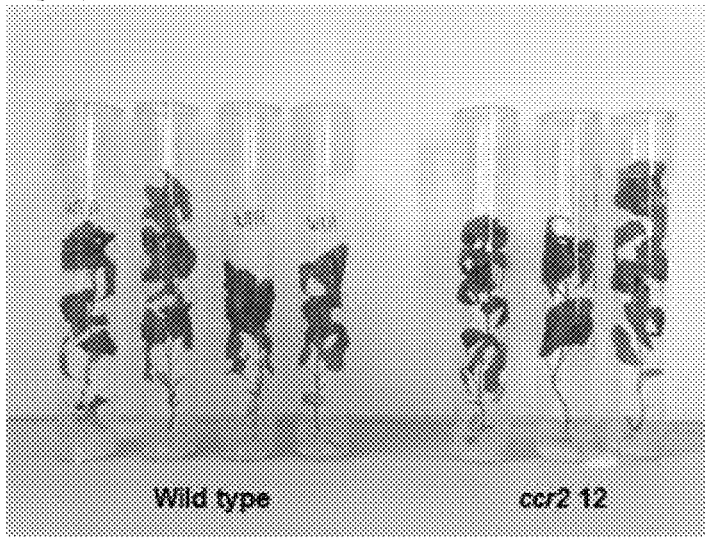

Figure 4C

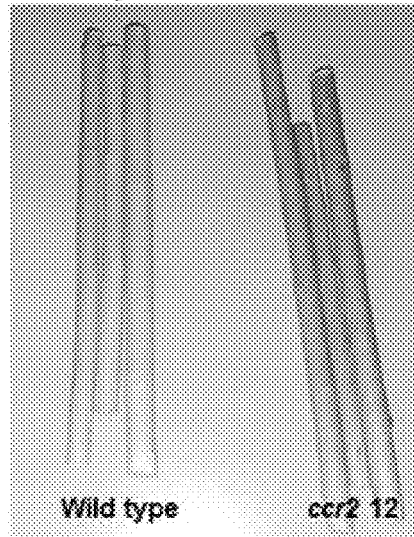

Figure 4D

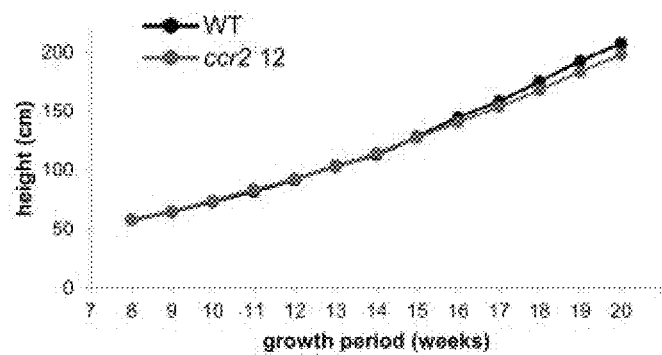

Figure 4E

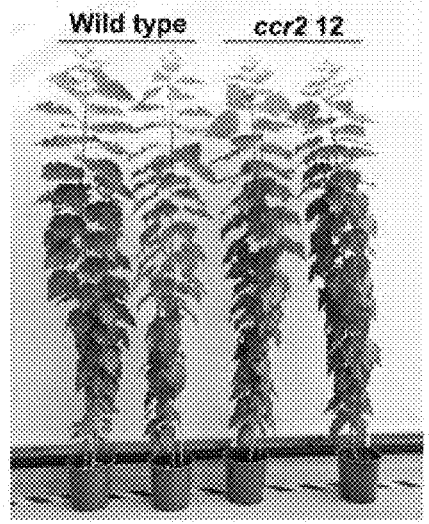

>*Populus tremula* CCR2 WT protein sequence

MPVDASSLSGQGQTICVTGAGGFIASWMVKLLLDKGYTVRGTARNPADPKNSHLRELEGAQERLTLCKADLL
DYESLKEAIQGCDGVFHTASPVTDDPEEMVEPAVNGTKNV<u>II</u>AAAEAKVRRVVFTSSIGAVYMDPNKGPDVV
IDESCWSDLEFCKNTKNWYCYGKAVAEQAAWDMAKEKGVDLVVVNPVLVLGPLLQPTVNASIVHILKYLTGS
AKTYANSVQAYVHVRDVALAHILVFETPSASGRYLCSESVLHRGEVVEILAKFFPEYPIPTKCSDEKNPRKQ
PYKFSNQKLRDLGFEFTPVKQCLYETVKSLQERGHLPIPKQAAEESVKIQ

>*Populus tremula* CCR2 mutated protein sequence

MPVDASSLSGQGQTICVTGAGGFIASWMVKLLLDKGYTVRGTARNPADPKNSHLRELEGAQERLTLCKADLL
DYESLKEAIQGCDGVFHTASPVTDDPEEMVEPAVNGTKNV<u>I*</u>AAAEAKVRRVVFTSSIGAVYMDPNKGPDVV
IDESCWSDLEFCKNTKNWYCYGKAVAEQAAWDMAKEKGVDLVVVNPVLVLGPLLQPTVNASIVHILKYLTGS
AKTYANSVQAYVHVRDVALAHILVFETPSASGRYLCSESVLHRGEVVEILAKFFPEYPIPTKCSDEKNPRKQ
PYKFSNQKLRDLGFEFTPVKQCLYETVKSLQERGHLPIPKQAAEESVKIQ

Figure 11B.

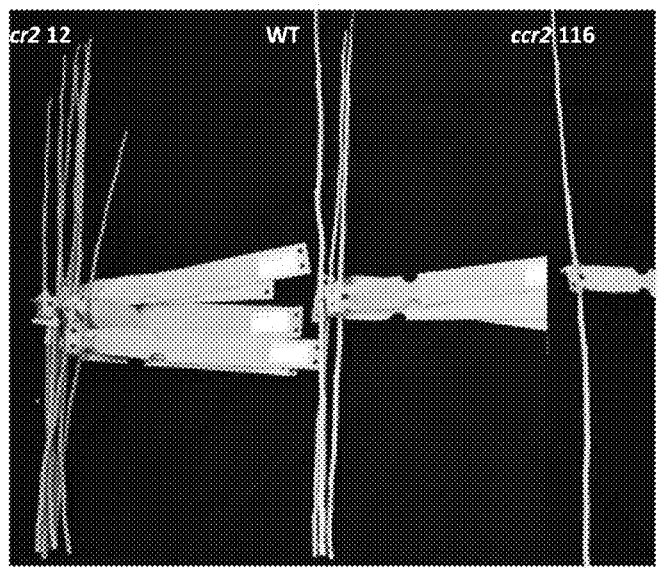

MUTANT PLANT CINNAMOYL-CoA REDUCTASE PROTEINS

CROSS-REFERENCE TO RELATED APPLICATIONS

This application is a national phase entry under 35 U.S.C. § 371 of International Patent Application PCT/EP2019/064764, filed Jun. 6, 2019, designating the United States of America and published in English as International Patent Publication WO 2019/234141 on Dec. 12, 2019, which claims the benefit under Article 8 of the Patent Cooperation Treaty to Great Britain Patent Application Serial No. 1809273.4, filed Jun. 6, 2018, the entireties of which are hereby incorporated by reference.

FIELD OF THE INVENTION

The present invention relates to a mutant plant Cinnamoyl-CoA Reductase (CCR) protein capable of restoring the yield penalty in plants with lignin traits such as ccr-related deficiencies and methods and uses thereof. More specifically, the invention relates to plants lacking functional wild type CCR protein but having a weak ccr allele resulting in lower lignin amounts and increased saccharification, further accompanied by plant growth restoration of the lignin modification-induced dwarfism.

BACKGROUND

Because of the increasing energy demand, depletion of the fossil fuel feedstock and global warming, a shift from today's fossil-based economy towards a bio-based economy is inevitable. In the latter, lignocellulosic biomass, which mainly consists of the polysaccharides cellulose and hemi-cellulose embedded in lignin, might play a crucial role since it can be used for the production of both energy and a plethora of chemicals. In the biorefinery, the cell wall polysaccharides are depolymerized into monomeric sugars through a process called saccharification. These sugar monomers can be converted further towards ethanol or other compounds through e.g. fermentation by microorganisms. However, the plant cell wall is recalcitrant towards deconstruction mainly because of the presence of lignin. This aromatic heteropolymer, that provides strength and hydrophobicity to the plant cell wall, hinders the saccharification process by immobilizing the hydrolytic enzymes and physically limiting their access to the cellulose and hemi-cellulose substrates. To improve the accessibility of the polysaccharides for enzymatic digestion, the biomass is pretreated with chemicals to break-down and extract lignin. Since pretreatment is a costly step in the conversion process, strategies are being sought to develop plant varieties that deposit less lignin. However, lignin-modified plants that show the highest improvement in saccharification efficiency typically suffer from growth perturbations. This lignin modification induced dwarfism (LMID) was shown to be mainly caused by the loss of vascular integrity leading to vessel collapse in the respective lignin-modified plants (Piquemal et al., 1998; Zhong et al., 1998; Jones et al., 2001; Franke et al., 2002; Stout and Chapple, 2004; Besseau et al., 2007; Huang et al., 2010; Voelker et al., 2010; Vanholme et al., 2013b; Yang et al., 2013; Vargas et al., 2016; De Meester et al., 2018).

Cinnamoyl-CoA reductase (CCR) catalyzes the first step of the monolignol-specific pathway. It converts the hydroxy-cinnamoyl-CoA thioesters to their corresponding hydroxy-cinnamaldehydes and downregulation of CCR typically results in a significant reduction in lignin content (Chabannes et al., 2001; Jones et al., 2001; Goujon et al., 2003; Dauwe et al., 2007; Leple et al., 2007; Jackson et al., 2008; Tamasloukht et al., 2011; Van Acker et al., 2014; Smith et al., 2017a). Plants deficient in CCR have tremendously increased saccharification efficiency. For example, the cellulose-to-glucose conversion in the *Arabidopsis thaliana* ccr1 mutant is more than 3-fold higher than that in wild-type plants. However, these plants also have a reduced biomass yield. By using the vessel-specific artificial SECONDARY WALL NAC BINDING ELEMENT of the XYLEM CYSTEINE PROTEASE 1 promoter (ProSNBE) to drive the expression of the CINNAMOYL-COA REDUCTASE1 (CCR1) gene in an *Arabidopsis* ccr1 mutant background, the total plant biomass was fully recovered while still having the high cellulose-to-glucose conversion efficiency of ccr1 mutants (De Meester et al., 2018).

Poplar (*Populus* ssp.) is a promising lignocellulosic biorefinery-crop since this tree is fast-growing, nutrient-efficient and requires no tillage for growth. Furthermore, this species can be clonally propagated, has a fully sequenced and annotated genome and several poplar species, including commercial hybrids, are easy to transform (Gelfand et al., 2013). Hybrid poplar shows great potential as a woody energy crop (Carroll and Somerville, 2009), and wood of CCR downregulated poplar had up to 161% increased ethanol yield per unit of biomass (Van Acker et al., 2014). CCR2 downregulated poplars are characterized by a red coloration of the xylem that often appeared in patches along the stem (Leple et al., 2007; Van Acker et al., 2014). Unfortunately, these transgenic poplars were not stably downregulated for CCR2 and suffered from collapsed vessels and associated yield penalties. As in *Arabidopsis* (De Meester et al., 2018), restoring the yield penalty of ccr2 poplars without settling in sugar yield by sufficiently reinforcing the vessels is a possibility. But still, RNAi or antisense transgenic poplars with reduced amounts of lignin are i) not stably downregulated for the respective lignin biosynthesis gene and ii) may still suffer from yield penalties by other mechanisms.

So, an unmet need exists for the generation of woody plants such as poplars i) that have stably reduced activity of the targeted lignin biosynthesis enzyme and, hence, stable reductions in lignin amounts, and ii) that do not suffer from yield penalties. In maize for instance, it has been shown that simply a lower wild type CCR activity was sufficient to reduce lignin content, and to retain growth similar to wild type (Tamasloukht et al., 2011; Smith et al., 2017a).

So, in conclusion, woody plants or trees with altered lignin content would be very promising feedstock for the bio-refinery for the production of biofuels and other bio-based materials. Furthermore, breeding efforts have been done to reduce lignin contents in bioenergy and silage, but the currently obtained solutions display some disadvantages still, since they are either transgenic (including RNAi, and often too costly to deregulate) and/or have a yield drag, so there is a need to find alternatives to circumvent these disadvantages.

SUMMARY OF THE INVENTION

The present invention is based on the finding that a novel mutant plant CCR protein, encoded by a weak allele upon genetically modifying hybrid poplar, was capable of introducing the advantage of lowering lignin amounts and increasing saccharification without inducing a yield drag or dwarfism. This finding allows to elegantly edit the genome by targeting certain positions in lignin biosynthesis genes, such as CCR to modify the protein stability or enzymatic activity, for instance of those CCR proteins, thereby fine-tuning the balance of overcoming a yield penalty issue, which is often observed in lignin traits, while preserving the valuable lignin trait. Those mutant plant CCR protein variants may be transgenically introduced in plants already pronouncing lignin trait-related deficiencies to restore dwarfism. Furthermore, such novel alleles are key for production of non-genetically modified organism (GMO) products with high sugar yield in bioenergy crops. Finally, such mutant plant CCR proteins may as well improve digestibility in the case of silage maize.

In a first aspect the invention relates to a nucleic acid molecule encoding a mutant plant Cinnamoyl-CoA Reductase (CCR) protein that is mutated in the conserved domain of said CCR amino acid sequence as depicted in SEQ ID NO: 1, wherein said conserved domain corresponds to the most conserved part of a FR_SDR_e annotated domain, which contains the typical OCR signature and NADP and active site residues important for CCR identity and activity. The mutation is characterized in that amino acid position(s) 98, 99 and/or 100 of said conserved domain as depicted in SEQ ID NO:1 are the mutation site(s). Alternatively, the invention relates to a nucleic acid molecule encoding a mutant plant CCR protein that is mutated in the conserved domain of said CCR amino acid sequence with a conserved domain with at least 50% amino acid identity to SEQ ID NO: 1, and characterized in that amino acid position(s) 98, 99 and/or 100 of said conserved domain with at least 50% amino acid identity to SEQ ID NO: 1 are the mutation site(s). Although the mutated position(s) concern residues that are different from said hall mark residues for CCR identity and activity, position 98 and 100 residues are conserved among plant CCR proteins, position 99 shows some variation in its residue identity (FIG. 6). In one embodiment, said mutation constitutes of at least one deletion at position 98, 99, and/or 100. In another embodiment, said mutation concerns exactly one of those 3 amino acid positions to be deleted. In a specific embodiment, the amino acid residue of position 98 is deleted, or alternatively, position 99 is deleted, or position 100 is deleted. In another embodiment, the mutation constitutes at least one deletion of 98, 99, and/or 100, and in addition a substitution of amino acid residues 99 or 100 as compared to SEQ ID NO:1, or as compared to the conserved domain with at least 50% amino acid identity to SEQ ID NO: 1. Specifically, residue 98 is deleted and residue 99 or 100 is substituted, alternatively residue 99 is deleted and 100 is substituted, or one embodiment contains a mutation wherein residue 100 is deleted and residue 99 is substituted. Another embodiment relates to a mutation consisting of at least one deletion of the residue at position 98-100, and a substitution of the residue at position 99 or 100, said substitution consisting of a polar amino acid. Specifically said substitution at position 99 or 100 results in a threonine, serine, glutamine, asparagine, tyrosine, or cysteine. One specific embodiment relates to a mutation wherein residue 99 and 100 of SEQ ID NO:1 are replaced by a single amino acid that is different from the ones at position 99 and 100 in SEQ ID NO:1.

Another embodiment relates to an expression vector comprising said nucleic acid molecule for expression in a plant cell. One particular embodiment describes the mutant plant CCR protein encoded by said nucleic acid molecule or by said expression vector.

Another aspect relates to a plant lacking functional CCR protein, further comprising the nucleic acid, the vector, or the mutant plant CCR protein of the invention, characterized in that plant growth is at least comparable to a control plant. In another embodiment, a plant with at least one knock-out ccr allele, and further comprising the nucleic acid, the vector, or the mutant plant CCR protein of the invention, is further characterized in that plant growth is at least comparable to a control plant. And one embodiment relates to a plant with reduced lignin amounts as compared to a control plant, further comprising the nucleic acid, the vector, or mutant plant CCR protein of the invention, being characterized in that plant growth is at least comparable to a control plant. In a specific embodiment, said reduction of lignin amounts is at least 10% as compared to a wild-type or control plant. And another embodiment relates to a plant with higher saccharification efficiency as compared to a control plant, further comprising the nucleic acid, the vector, or mutant plant CCR protein of the invention, being characterized in that plant growth is at least comparable to a control plant. In a specific embodiment, said increase in saccharification efficiency is at least 30% as compared to a wild-type or control plant.

In a specific embodiment, said plant is a crop. Alternatively, said plant is a cereal plant. And in another embodiment, said plant is a woody plant, which may be envisaged to be a tree, such as poplar, pine or eucalyptus. One specific embodiment relates to a seed or a plant cell derived from said plant of the invention.

In a second aspect of the invention, a method to produce a plant with restored growth with a lignin trait is disclosed, comprising the steps of: (i) introducing the nucleic acid molecule, vector or mutant CCR protein of the present invention in said plant with abnormal growth or in its plant cells, and ii) incubate and isolate a plant regenerated from said plant, and iii) identify the plants with normal restored growth. In a specific embodiment, said introducing of the mutant protein or mutant sequence is obtained via transformation of a recombinant DNA element, or using gene editing targeting the endogenous CCR gene(s) to insert a mutation and/or disruption in at least 1 allele. Specifically, said introduced mutation is the mutation wherein the amino acid residues of CCR corresponding to position 99 and 100 as depicted in SEQ ID NO:1 are replaced by one amino acid that is different from both, and preferably is a polar amino acid, most preferably threonine and serine.

A final aspect of the invention relates to a method to identify mutant plant lignin biosynthesis proteins capable of restoring growth in a dwarf plant is depicted, comprising the steps of: (i) introducing a mutation in a plant that has at least one knock-out allele of a lignin biosynthesis gene, so as to induce at least one mutation in a second allele of said lignin biosynthesis gene of said plant, (ii) followed by screening for plants with a normal growth phenotype but with the lignin trait, and (iii) identifying the nature of the mutation in said plant mutant lignin biosynthesis allele. In a specific embodiment, said lignin biosynthesis gene is CCR. In another specific embodiment, said method to introduce said mutation in a plant that has at least one knock-out allele of a lignin biosynthesis gene, makes use of gene editing, so as to induce the at least one mutation in a second allele in a targeted manner. In another specific embodiment, said introducing of a mutation in a plant is bi-allelic, and concerns the mutation of a lignin biosynthesis gene, such as CCR, resulting in a plant with mutant CCR protein, and in step ii) to screen for a plant with normal growth, and reduced or altered lignin amounts, and iii) to identify the nature of the mutation in the plant mutant lignin biosynthesis gene. In a further specific embodiment, said induced mutation in step i) results in reduced or altered lignin biosynthesis activity in said plant. Specifically, said mutation results in reduced activity of the lignin biosynthesis gene, such as CCR, and said reduction is preferably an enzymatic activity lower than wild type activity in a normal plant, and within the range of at least 60% to maximally 90% of wild type activity. In a particular embodiment, said reduced activity is obtained for the plant via reducing lignin biosynthesis gene expression in said plant, or via insertion of a mutation and/or disruption in at least 1 allele of said lignin biosynthesis gene of said plant. In a specific embodiment, said lignin biosynthesis gene is CCR.

DESCRIPTION OF THE FIGURES

The patent or application file contains at least one drawing executed in color. Copies of this patent or patent application publication with color drawing(s) will be provided by the Office upon request and payment of the necessary fee.

The drawings described are only schematic and are non-limiting. In the drawings, the size of some of the elements may be exaggerated and not drawn to scale for illustrative purposes.

Wild type and ccr2 after growing for three months on MS medium in long day conditions.

Figure 2:

FIG. 2. Phenotype of ccr2 poplars grown on soil.

Plants were grown for four months in the greenhouse. The ccr2 mutant poplars carrying biallelic frameshift mutations were grown under a dome to keep them alive. The dome was removed prior to taking the picture.

Figure 3:
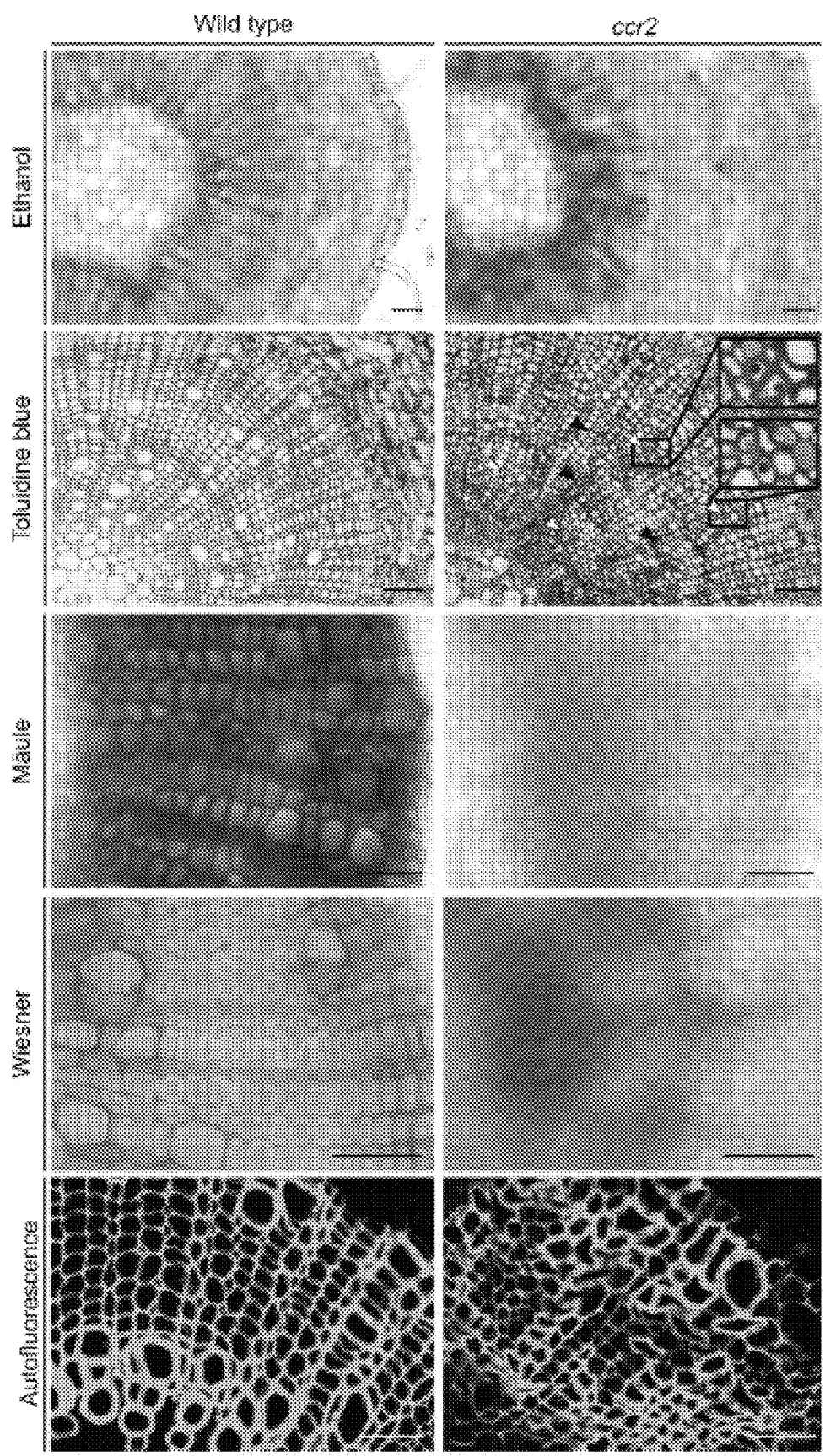

FIG. 3. Lignin deposition in stems of ccr2 poplars.

Transverse stem sections of wild type and ccr2 mutants (carrying biallelic frameshift mutations) grown for 4 months in MS medium. Ethanol treated sections showed a red coloration of the xylem cells in the ccr2 lines. Toluidine blue staining revealed the presence of round, open vessels in the xylem of wild type and collapsed vessels (black arrowheads) in the xylem of ccr2. Furthermore, circle-shaped blue structures were found in ccr2 vessels and fibers (white arrowheads and insets). Mäule and Wiesner staining showed reduced lignification in the ccr2 lines when compared to wild type. The images shown are representative for all ccr2 lines carrying biallelic frameshift mutations. Scale bars=50 µm.

FIGS. 4A-4D. Protein sequence and phenotype of ccr212.

(FIG. 4A) Amino acid sequence of the wild-type (SEQ ID NO:3) and mutated (SEQ ID NO:4) CCR2 proteins of the *Populus alba* allele. The amino acids that are changed in ccr2 12 are indicated in bold red. (FIG. 4B) Phenotype of wild-type and ccr2 12 poplars grown on MS-medium in long-day conditions for 3 months. (FIG. 4C) Phenotype of debarked wild-type and ccr2 12 stems grown in the greenhouse when they reached heights of 1.20 m. ccr2 12 stems color red indicative for CCR deficiency (FIG. 4D) Growth curve of wild type and ccr2 12 (after cutting back the original stem). No significant differences in height were found between the wild type and ccr212 lines (Dunnett-Hsu adjust t-test; p-value>0.05; wild type, n=11; ccr212, n=11). (E) Phenotype of ccr2 12 after growing for 20 weeks in the greenhouse (after cutting back the original stem).

Figure 5:
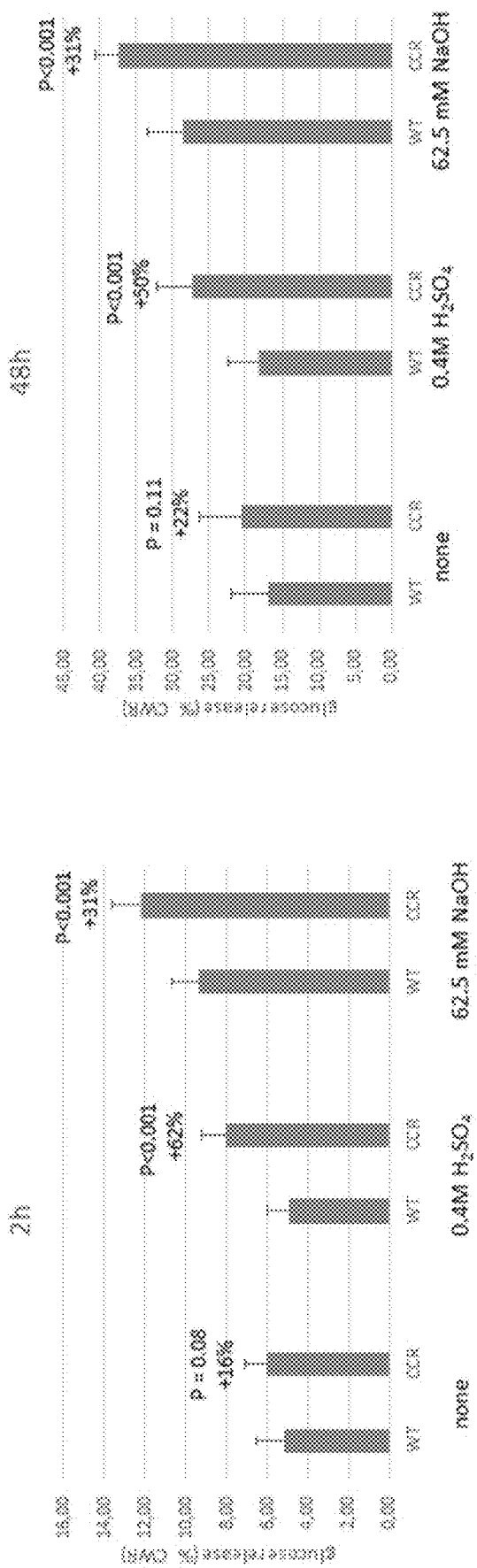

FIG. 5. Saccharification efficiency of ccr2 poplars.

Glucose release (% CWR) after 2 h and 48 h of saccharification of 3 months old (~1.2 m size) wild type and ccr2 12 stems (n=12). Samples were saccharified using no pre-treatment, acid pretreatment (0.4 M $H_2SO_4$), or alkaline pretreatment (62.5 mM NaOH). The percentage of increased glucose yield (and associated p-value) in the ccr212 lines when compared to the wild type is indicated for every pretreatment used. The ccr212 lines showed an increased up to 50% higher glucose release as compared to wild type in pretreated conditions.

Figure 6A:
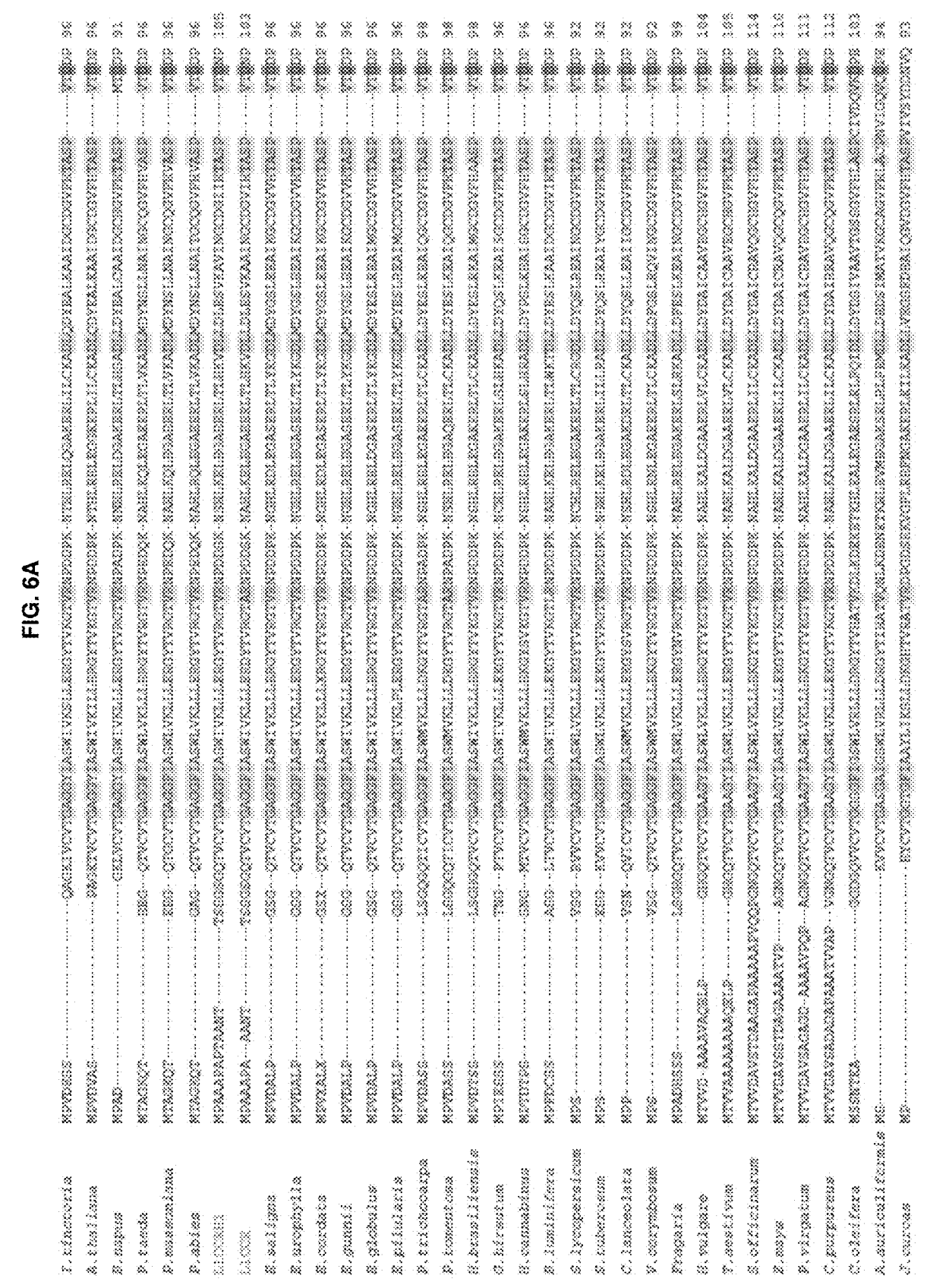
Figure 6B:
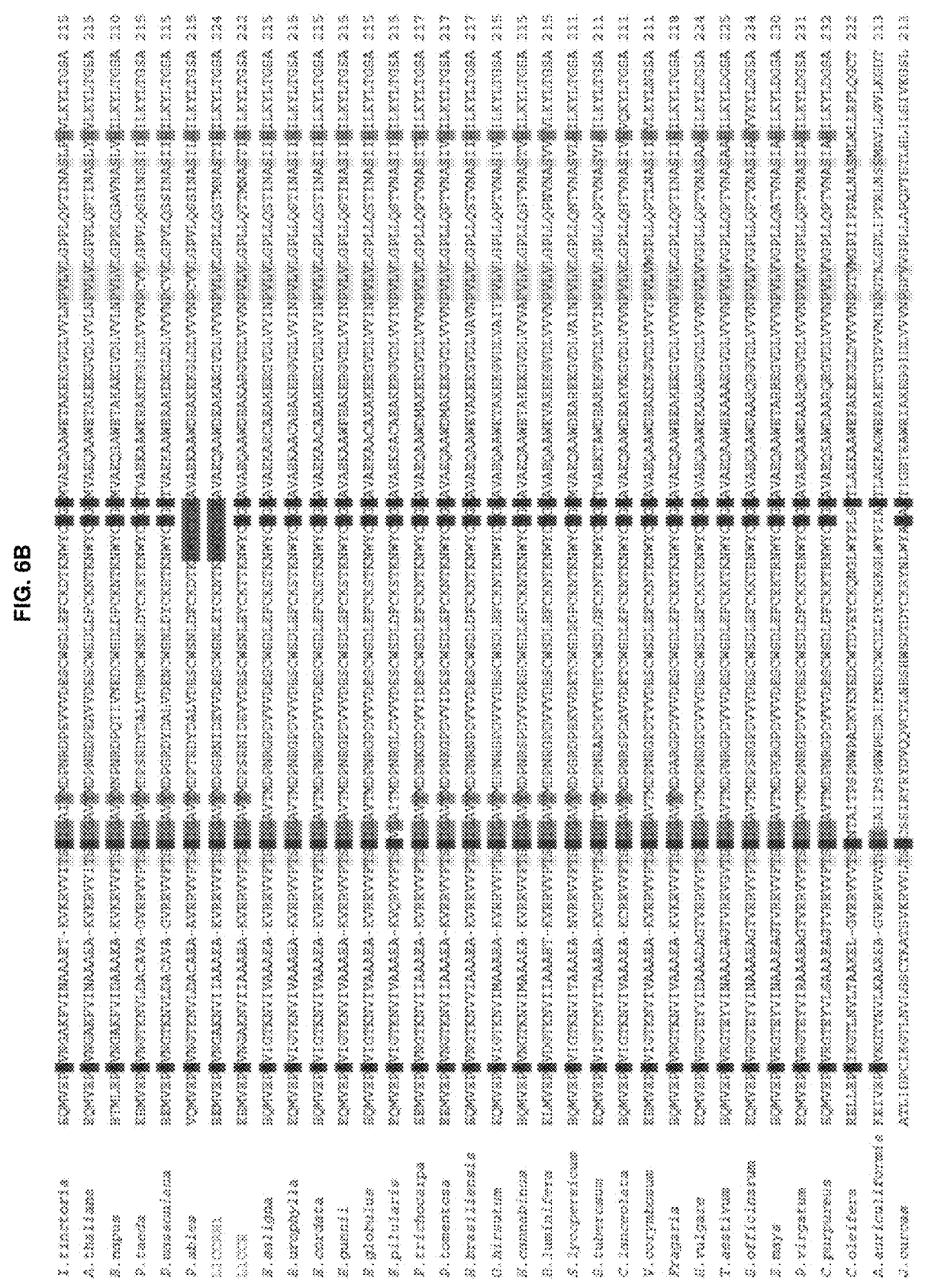
Figure 6C:
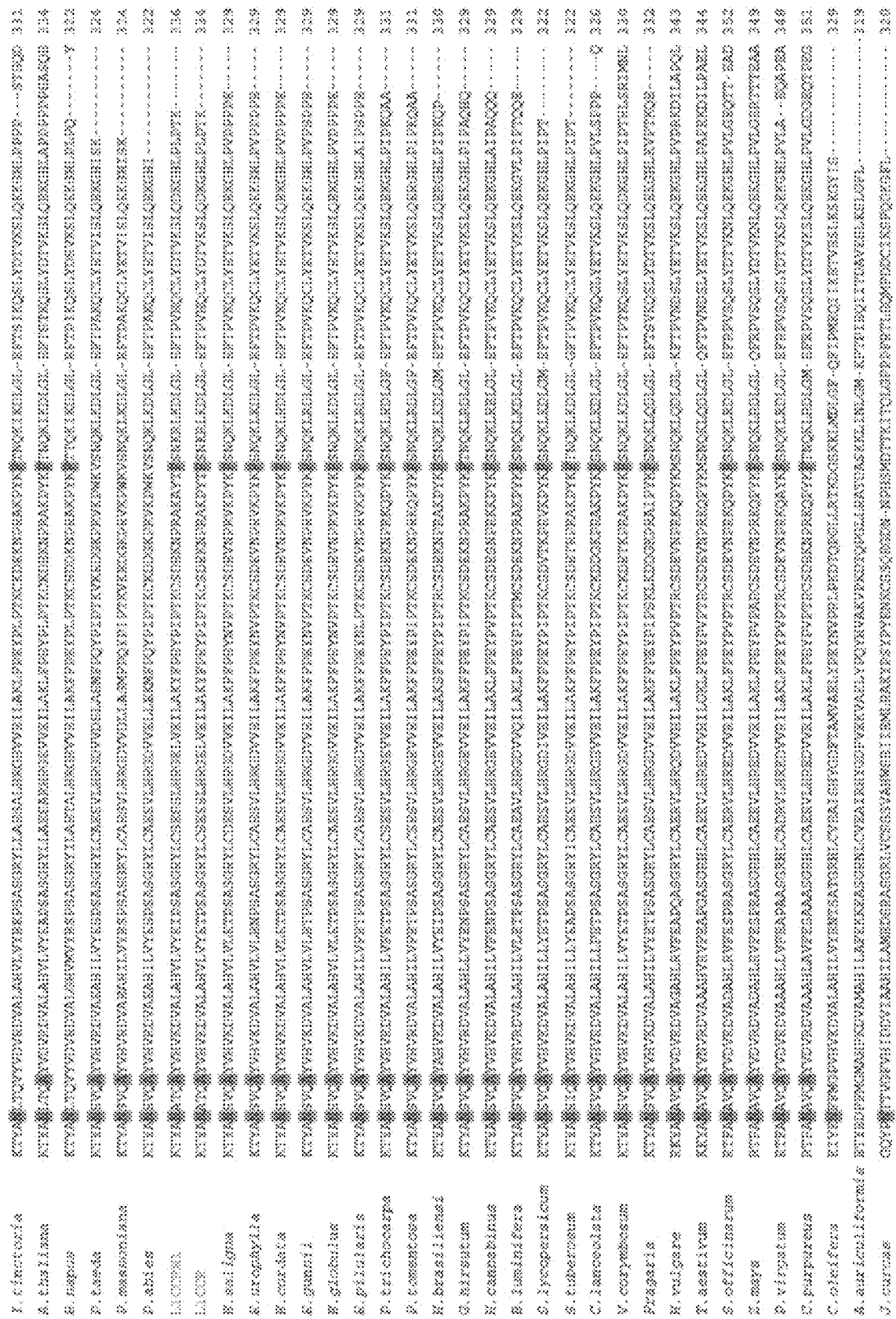

FIGS. 6A-6C. Alignment of CCR amino acid sequences from different plants illustrating a functional conserved domain FR_SDR_e (Dihydroflavanol reductase).

The LI-CCRH1 (presented in grey color) sequence was aligned with homologous CCR sequences, showing the Signatural CCR sequence (NWYCYGK (SEQ ID NO:65); pink color). Active site residues obtained from Conserved Database Domain (CDD) search are shown in red color; NADP binding domain residues are distinguished by yellow color; substrate binding pocket is indicated by green color. Gaps are introduced to maximize homology and are shown by dashes. Highly conserved residues; Tyr (172), Lys (174) and Ser (136) are present in all conserved motifs of CCRs and are supposed to play critical role in catalysis. The amino acid positions corresponding to the changed amino acids in the protein encoded by the ccr212 weak allele are boxed. GenBank accession numbers of all CCRs used in alignment are as follows (starting from top): ADC40029 (*Isatis tinctoria* SEQ ID NO:8), NP_173047 (*Arabidopsis thaliana* SEQ ID NO:9), AEK27166 (*Brassica napus* SEQ ID NO:10), AAL47684 (*Pinus taeda* SEQ ID NO:11), ACE76870 (*Pinus massoniana* SEQ ID NO:12), CAK18610 (*Picea abies* SEQ ID NO:13), ABL01801.3 (*Leucaena leucocephala* SEQ ID NO:14), EU195224 (*Leucaena leucocephala* SEQ ID NO:15), AF297877_1 (*Eucalyptus saligna* SEQ ID NO:16), CBG37721 (*Eucalyptus urophylla* SEQ ID NO:17), AAT74875 (*Eucalyptus cordata* SEQ ID NO:18), CAA56103 (*Eucalyptus gunnii* SEQ ID NO:19), AAT74876 (*Eucalyptus globulus* SEQ ID NO:20), ACZ59064 (*Eucalyptus pilularis* SEQ ID NO:21), CAC07424 (*Populus trichocarpa* SEQ ID NO:22), ACE95172 (*Populus tomentosa* SEQ ID NO:23), ADU64758 (*Hevea brasiliensis* SEQ ID NO:24), ACQ59094 (*Gossypium hirsutum* SEQ ID NO:25), ADK24219 (*Hibiscus cannabinus* SEQ ID NO:26), ACJ38670 (*Betula luminifera* SEQ ID NO:27), AAY41879 (*Solanum lycopersicum* SEQ ID NO:28), AAN71761 (*Solanum tuberosum* SEQ ID NO:29), BAE48787 (*Codonopsis lanceolate* SEQ ID NO:30), AC114382 (*Vaccinium corymbosum* SEQ ID NO:31), AAP46143 (*Fragaria×ananassa* SEQ ID NO:32), AAN71760 (*Hordeum vulgare* SEQ ID NO:33), ABE01883 (*Triticum aestivum* SEQ ID NO:34), CAA13176 (*Saccharum officinarum* SEQ ID NO:35), ACG33996 (*Zea Mays* SEQ ID NO:36), ACZ74584 (*Panicum virgatum* SEQ ID NO:37), ADY39751 (*Cenchrus purpureus* SEQ ID NO:38), ACQ41893 (*Camellia oleifera* SEQ ID NO:39), ADQ53455 (*Acacia auriculiformis×Acacia mangium* SEQ ID NO:40), ACS32301 (*Jatropha curcas* SEQ ID NO:41). Adopted from Sonawane et al., 2013.

Figure 7:
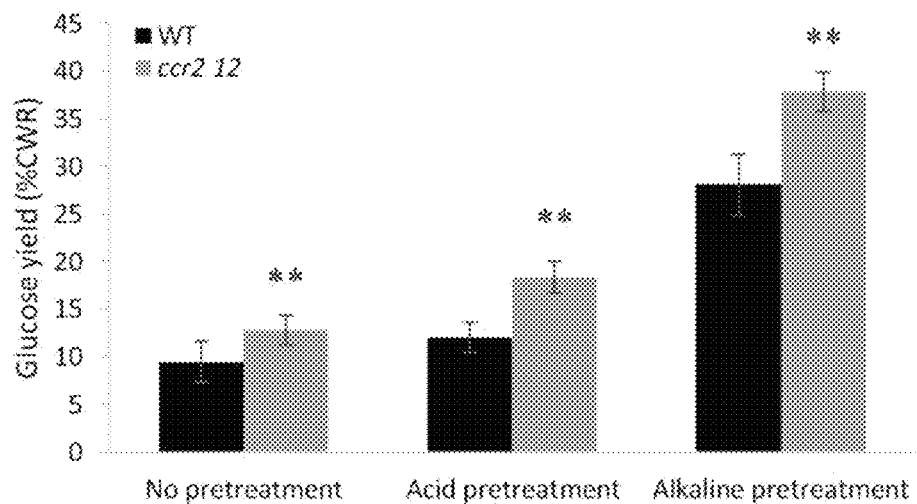

FIG. 7. Saccharification assays of ccr212.

Saccharification efficiency of stem biomass from 2 m tall wild-type (WT) and ccr2 12 plants. Samples were saccharified using no pretreatment, acid pretreatment (1 m HCl), or alkaline pretreatment (62.5 mm NaOH). In all pretreatments tested, ccr212 had an increased amount of glucose released (% CWR) (two-tailed Student's t-test; **P<0.01; wild type, n=10; ccr2 12, n=11). Error bars indicate the standard error (wild type, n=10; ccr212, n=11).

Figure 8:

FIG. 8. Dwarf phenotype of the biallelic knock-out T2_1 ccr2 poplar generated with the gRNA targeting the fourth exon of the CCR2 gene, versus wild-type poplar hybrids.

Figure 9:
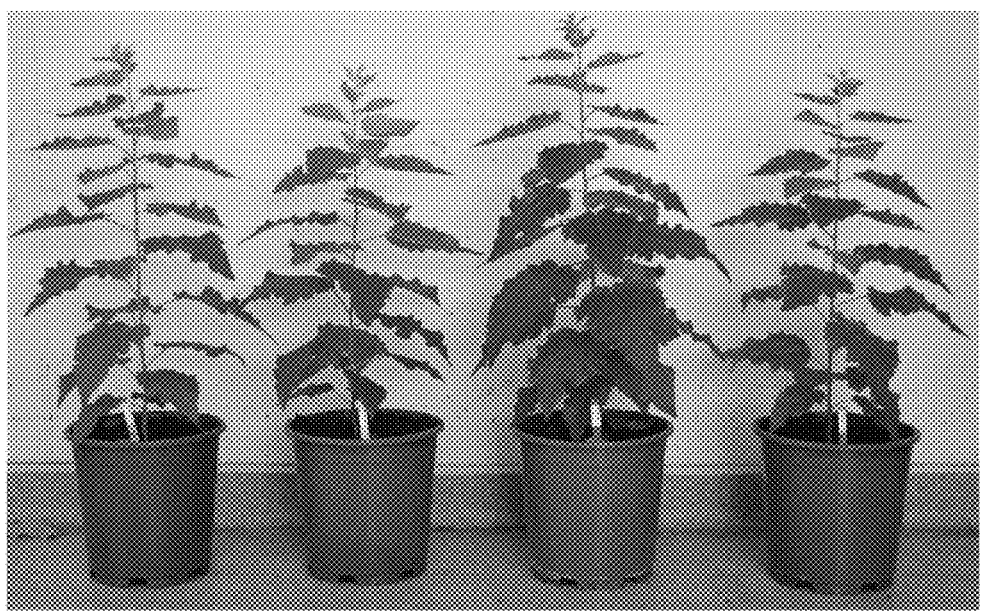

FIG. 9. Plant growth of different poplar lines.

Phenotype of the ccr2 mutated poplars and wild type. From right to left, wild type, *Populus tremula* mono-allelic CCR2 knock out, *Populus alba* mono-allelic CCR2 knock out and ccr212.

Figure 10:
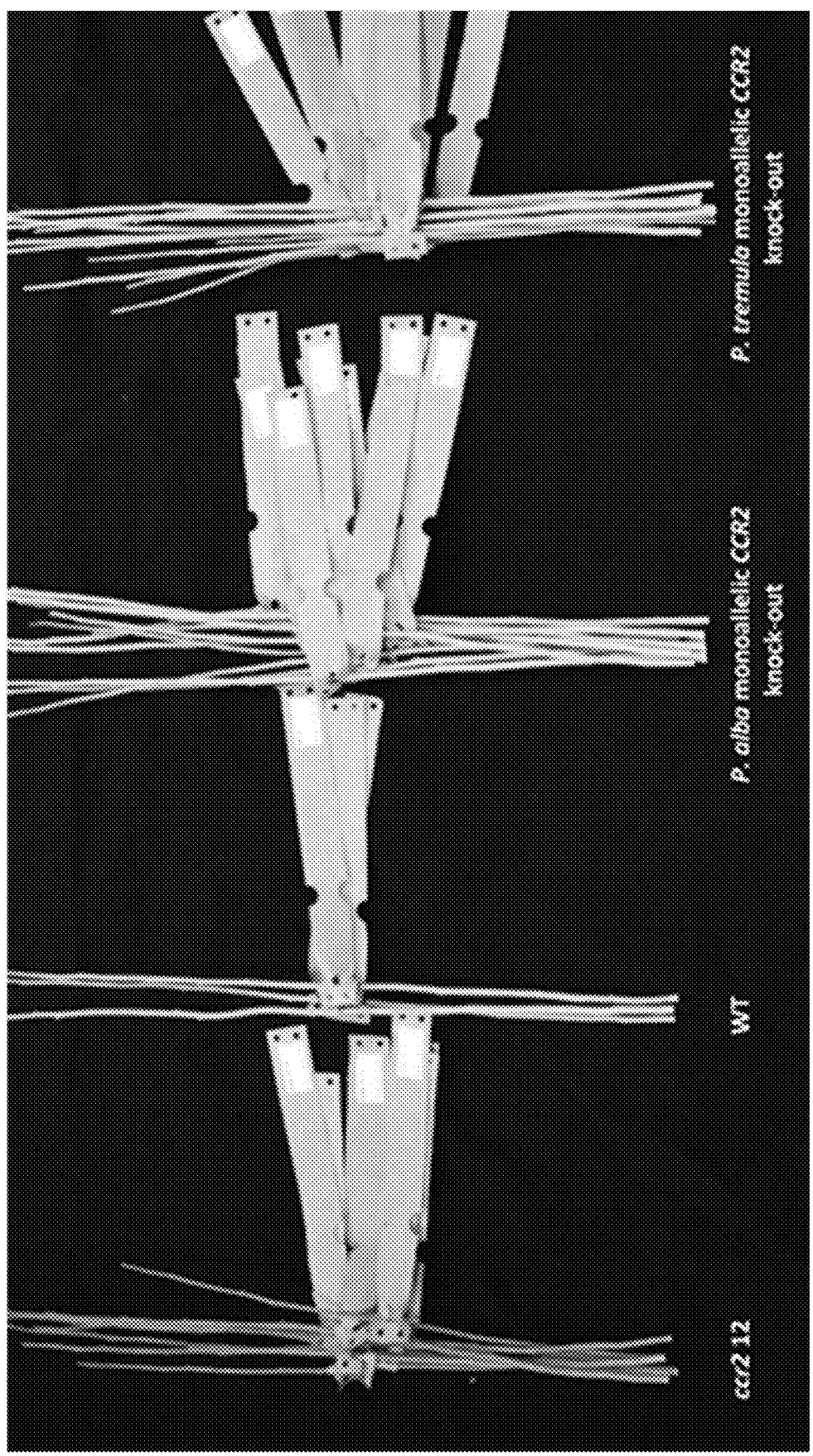

FIG. 10. Phenotype of debarked stems of WT, *P. alba* monoallelic CCR2 knock-out plants, *P. tremula* monoallelic CCR2 knock-out plants and ccr212.

Plants were grown for 11 weeks in the greenhouse. The red xylem phenotype is only present in ccr2 12.

FIGS. 11A-11B. ccr2116 mutant poplar sequence and phenotype.

FIG. 11A. Amino acid sequence of the mutant (SEQ ID NO:93) and wild-type (SEQ ID NO:2) CCR2 proteins of *Populus tremula*. The mutated amino acid in ccr2 116 is indicated in bold/underlined. FIG. 11B. Phenotype of debarked stems of WT, ccr2116 plants and ccr212. Plants were grown for 11 weeks in the greenhouse. The red xylem phenotype is only present in ccr2 12.

Figure 12:
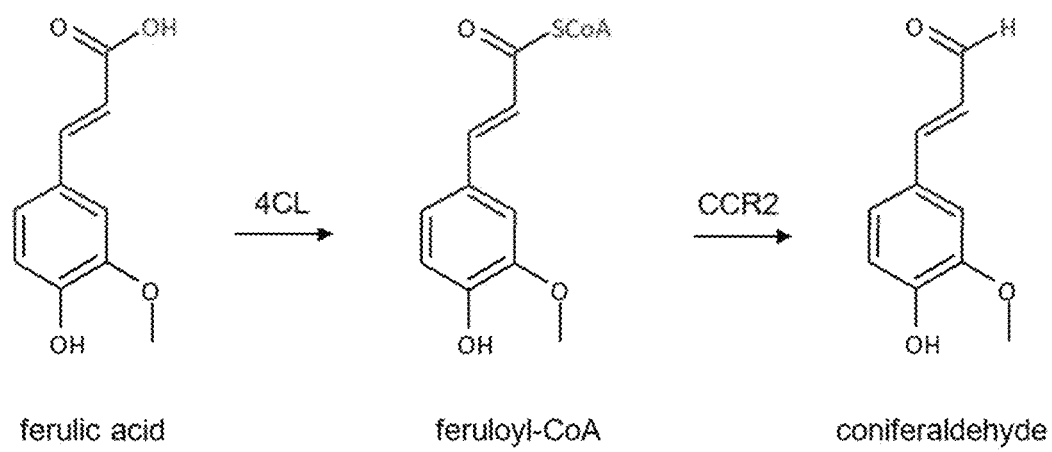

FIG. 12. Principle of the yeast feeding assay to test the activity of the recombinantly produced mutant CCR2 protein, as expressed in the ccr212 lines.

Yeast cultures were engineered to express 4CL and the WT (SEQ ID NO:3) or mutated *P. alba* CCR2 protein (SEQ ID NO:4). After feeding the yeast cultures with ferulic acid, the activity of the respective CCR2 protein was judged based on the production of coniferaldehyde (the product of CCR2).

Figure 13A:
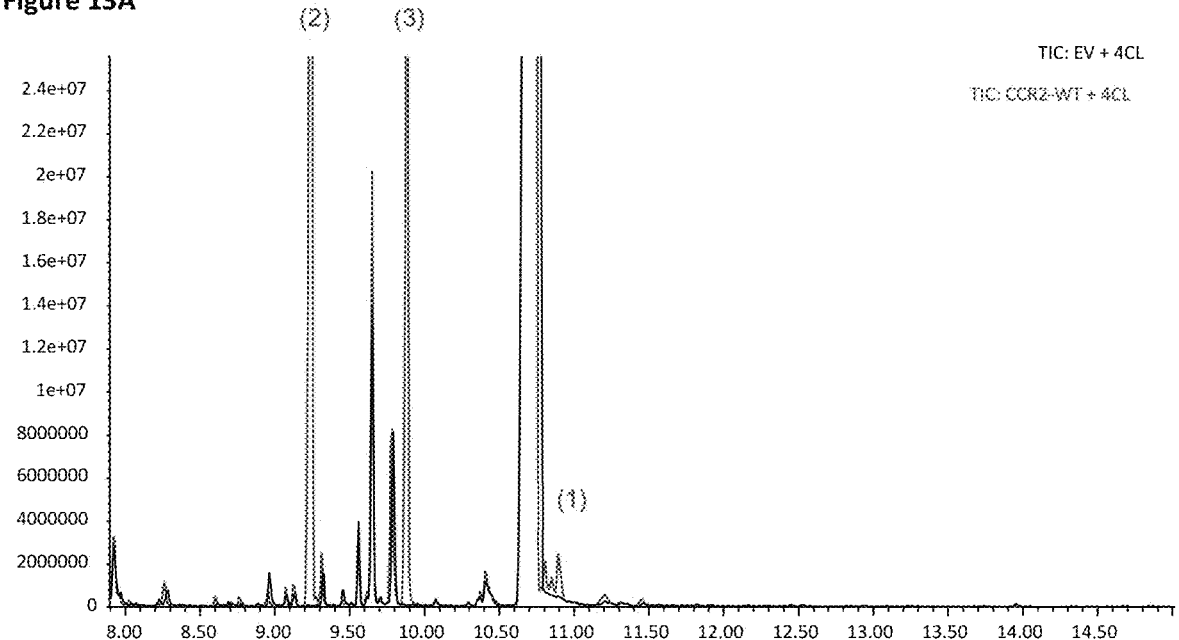
Figure 13B:
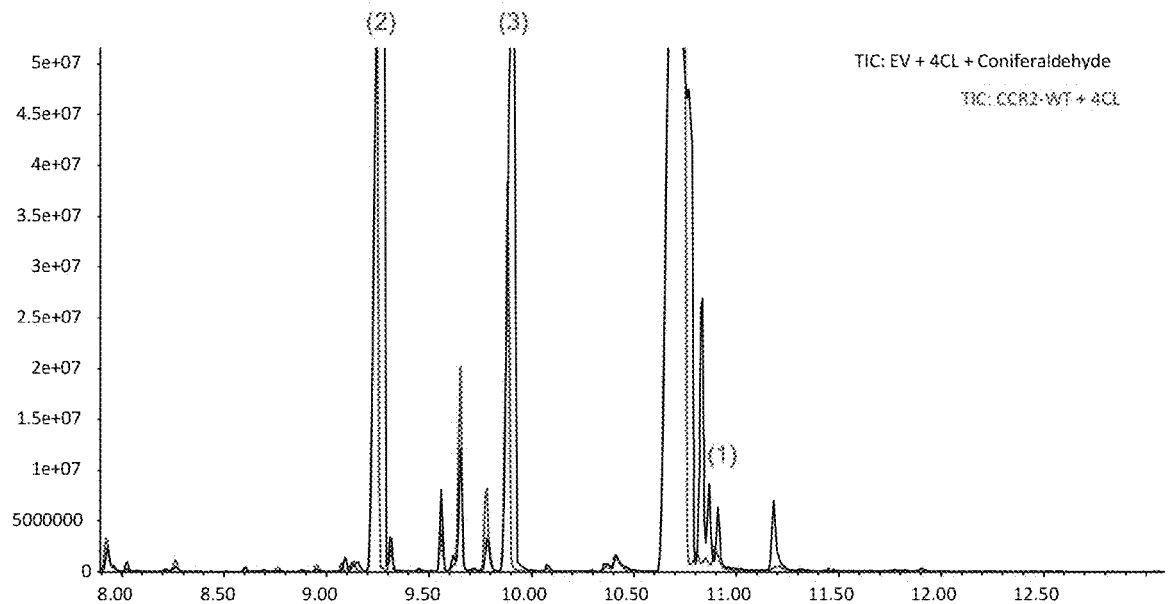
Figure 13C:
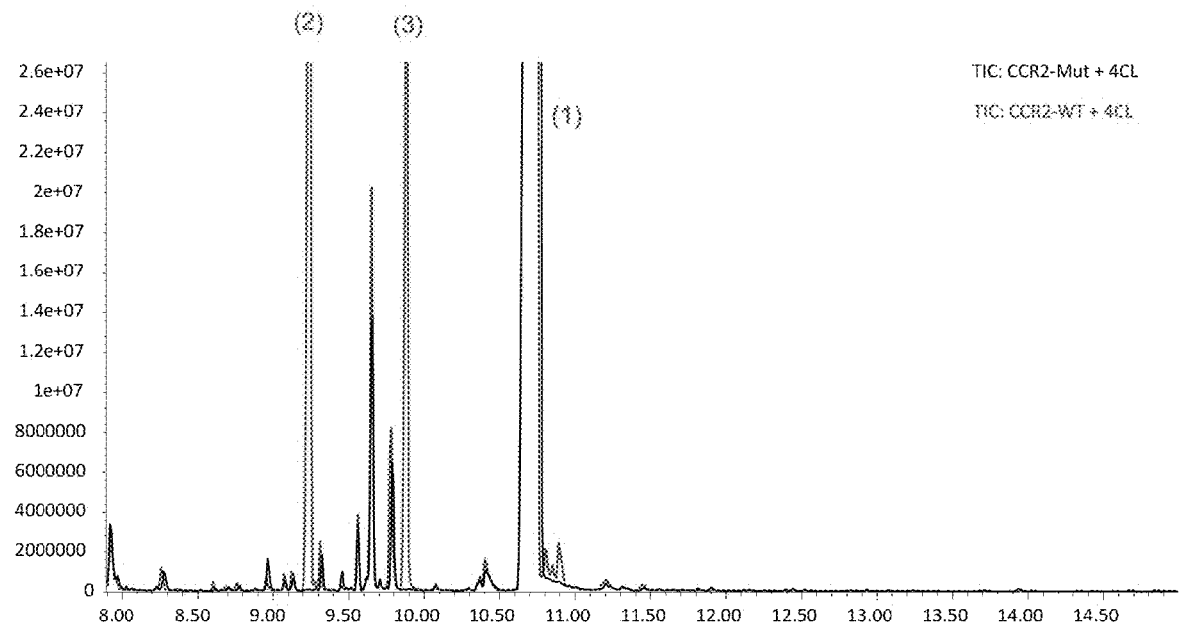

FIGS. 13A-13C. Yeast feeding assays to determine the activity of the mutant *P. alba* CCR2 protein present in ccr212.

(FIG. 13A) GC-MS chromatograms of the extracted compounds present in 4CL-engineered yeast (black) and 4CL- and WT *P. alba* CCR2-engineered yeast (grey) both fed with ferulic acid. (FIG. 13B) GC-MS chromatograms of the extracted compounds present in 4CL-engineered yeast fed with coniferaldehyde (black) and 4CL- and WT *P. alba* CCR2-engineered yeast (grey) both fed with ferulic acid. (FIG. 13C) GC-MS chromatograms of the extracted compounds present in 4CL- and mutated *P. alba* CCR2-engineered yeast (black) and 4CL- and WT *P. alba* CCR2-engineered yeast (grey) both fed with ferulic acid. Peak (1) represents coniferaldehyde, peak (2) and (3) are additional markers for the presence of coniferaldehyde. TIC, total ion current; EV, empty vector.

DETAILED DESCRIPTION TO THE INVENTION

The present invention will be described with respect to particular embodiments and with reference to certain drawings but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying drawings. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $4^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

Definitions

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

As used herein interchangeably, "nucleic acid" or "nucleic acid molecule" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g. peptide nucleic acids). "Gene" as used here includes both the promoter region of the gene as well as the coding sequence. It refers both to the genomic sequence (including possible introns) as well as to the cDNA derived from the spliced messenger, operably linked to a promoter sequence. An "allele" is a variant from a gene, which may result in a different phenotypic trait of said gene.

The term "wild-type" refers to a gene or gene product isolated from a naturally occurring source. A wild-type gene or gene product is that which is most frequently observed in a population or species and is thus arbitrarily designed the "normal" or "wild-type" form of the gene or gene product. In contrast, the term "modified", "mutant", "mutated" or "variant" refers to a gene or gene product that displays modifications in sequence, post-translational modifications and/or functional properties (i.e. altered characteristics) when compared to the wild-type gene or gene product of the same species. It is noted that naturally occurring mutants can be isolated; these are identified by the fact that they have altered characteristics when compared to the wild-type gene or gene product.

The term "abnormal" when used in the context of organisms, plants, tissues, cells or enzymatic activities, refers to those organisms, plants, tissues, cells or enzymatic activities thereof that differ in at least one observable or detectable characteristic (e.g., phenotype, processing, function, quantitative level etc.) from those organisms, plants, tissues, cells, or enzymatic activities that display the "normal" (expected) respective characteristic or level. Characteristics or levels which are normal or expected for one organism, species, or protein type, might be abnormal for a different species, organism or protein type.

"Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. By "encoding" or "encoded," with respect to a specified nucleic acid, is meant comprising the information for transcription into an RNA and in some embodiments, translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. A "chimeric gene" or "chimeric construct" is a recombinant nucleic acid sequence in which a promoter or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence. The regulatory nucleic acid sequence of the chimeric gene is not operatively linked to the associated nucleic acid sequence as found in nature.

The term "expression" as used herein refers to the biosynthesis of a gene product, including the transcription and/or translation of said gene product. For example, for the purposes of the present invention, expression of a polynucleotide encoding a (mutant) CCR polypeptide, via the production of an RNA molecule that translates a (mutant) CCR polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Further, "expression" of a gene can refer to the transcription of the gene into a non-protein coding transcript.

The terms "protein", "polypeptide", "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes posttranslational modifications of the polypeptide, such as glycosylation, phosphorylation and acetylation. Based on the amino acid sequence and the modifications, the atomic or molecular mass or weight of a polypeptide is expressed in (kilo)dalton (kDa). By "recombinant polypeptide" is meant a polypeptide made using recombinant techniques, i.e., through the expression of a recombinant or synthetic polynucleotide, preferably in a heterologous expression system or host. By "isolated" is meant material that is substantially or essentially free from components that normally accompany it in its native state. For example, an "isolated polypeptide" refers to a polypeptide which has been purified from the molecules which flank it in a naturally-occurring state, e.g., a CCR protein which has been removed from the plant compounds or medium molecules of the production host that are adjacent to the protein. An isolated protein can be generated by amino acid chemical synthesis or can be generated by recombinant production, or even be isolated from its natural environment, i.e. for plant CCR proteins isolated from plant tissue.

The term "transgenic", "transgene" or "recombinant", as used herein, means with regard to, for example, a nucleic acid sequence, an expression cassette, chimeric gene construct or a vector comprising the nucleic acid sequence or an organism transformed with the nucleic acid sequences, expression cassettes or vectors according to the invention. A transgenic plant for the purposes of the invention is thus understood as meaning, as above, that the nucleic acids used in the method of the invention are not present in, or originating from, the genome of said plant, or are present in the genome of said plant but not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, heterologous expression of the nucleic acids takes place. Preferred transgenic plants are mentioned herein. The term "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct or vector of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1 102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP1198985, Aldemita and Hodges (Planta 199: 612-617, 1996); Chan et al. (Plant Mol Biol 22 (3): 491-506, 1993), Hiei et al. (Plant J 6 (2): 271-282, 1994). In the case of corn transformation, the preferred method is as described in either Ishida et al. (Nat. Biotechnol 14(6): 745-50, 1996) or Frame et al. (Plant Physiol 129(1): 13-22, 2002). Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). *Agrobacterium*-mediated transformation of *P. tremula*×*P. alba* 717-1 B4 is for instance performed according to Leple et al. (1992).

The nucleic acid molecule or the construct to be expressed is preferably cloned into a vector, which is suitable for transforming *Agrobacterium tumefaciens*, for example pBin19 (Bevan et al (1984) Nucl. Acids Res. 12-8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hofgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

The genetically modified plant cells can be regenerated via all methods with which the skilled worker is familiar. Suitable methods can be found in the abovementioned publications by S. D. Kung and R. Wu, Potrykus or Hofgen and Willmitzer, or Leplé et al. (1992). Generally, after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art. The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest. The choice of suitable control plants is a routine part of an experimental setup and may include corresponding wild type plants, or may as well include corresponding plants without the gene of interest, i.e. plants with a knock-out of ccr, or may as well include plants following the same treatment (e.g. transformation), but lacking the effect (e.g. using an empty vector without mutant CCR gene). The control plant is typically of the same plant species, even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Detailed Description

The need for stably altered expression levels or knockouts/downs of CCR2 in poplar plants was clear from earlier observations that RNAi of CCR2 in poplar was not capable of achieving a stable ccr phenotype, such as a uniform red coloration of the xylem. So, ccr2 knock-out poplar plants were generated using the CRISPR/Cas9 gene editing system, by using one gRNA to specifically target the third exon of both CCR2 alleles in hybrid P. tremula×P. alba poplar.

Figure 1:
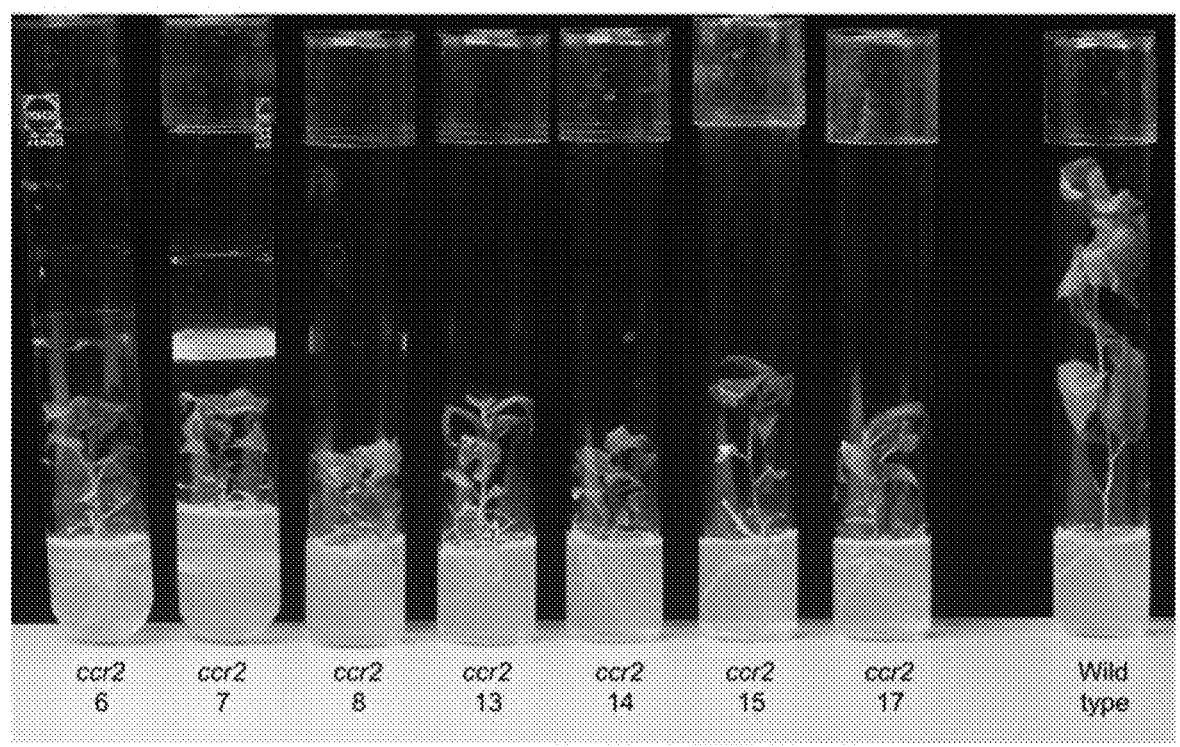
FIG. 1. Phenotype of in vitro grown ccr2 poplars carrying biallelic frameshift mutations.

However, ccr2 poplars with biallelic frameshift mutations were severely dwarfed and could barely survive out of the humid conditions of in vitro culture (FIG. 1; FIG. 2), which is a known issue in several lignin traits. Unexpectedly, one modified ccr2 line did not show such a growth defect, the ccr2 12, which formed the basis of this invention, since this line contained a frameshift mutation in one allele, while having a deletion of 3 base pairs in the other allele resulting into a 2 amino acid change in its wild-type protein sequence of poplar, the mutation being present in a very conserved region or motif of the protein. As a result, the mutant CCR protein of the ccr212 line is characterized by a mutation including a deletion and a substitution of the amino acids corresponding to position 114 and 115 of wild type CCR2 (involving an Isoleucine and Alanine in P. tremula and P. alba, as depicted in SEQ ID NO: 2 and 3, resp.), wherein said substitution is different from said amino acids, and in ccr2 12 concerns a substitution to a Threonine, resulting in mutant CCR2 protein with a sequence corresponding to SEQ ID NO:4 and/or 5 (mutant proteins for P. alba and P. tremula CCR2, resp.), respectively. Surprisingly, the ccr2 12 plants carrying one ccr2 knock-out (ko) allele and one ccr2 mutant allele did not show a dwarfed phenotype. A red coloration of the xylem was observed in ccr2 12, indicative of reductions in CCR activity, and typical of reduced lignin amounts and increased saccharification efficiency. Mono-allelic ko poplar plants did not show this typical CCR deficiency phenotype though, allowing to conclude that the mutant CCR2 allele, rather than partial CCR activity caused by just one ko allele, is causative for this lignin trait not suffering from yield losses.

Besides such mutant CCR2 proteins, the invention further reveals a screening method to identify mutant lignin biosynthesis proteins capable of restoring plant growth, for instance of lignin-modification-induced dwarfed plants, hence a screening method to produce plants with reduced lignin amounts and normal growth. Said screening method may comprise steps of providing plants with at least one knock-out allele of a lignin biosynthesis gene, and induce a second mutant allele of said lignin biosynthesis gene, such as a mutation that differs in n×3 nucleotides, further select said mutant sequence as an allelic variant. Said method also allows to identify how to modify the encoded lignin biosynthesis protein by small amino acid deletions/changes, resulting in lower lignin content and without impact on biomass. Said screening method is interesting to identify specific mutant alleles that do not result in a knock-out, but a stable knock-down effect. Specifically related to this invention, said lignin biosynthesis gene is CCR, and/or said introduction of a second mutation is obtained by gene editing.

In a first aspect, the invention relates to a nucleic acid molecule encoding a mutant plant CCR protein that has a mutation in the conserved domain of CCR proteins as depicted in SEQ ID NO:1 (corresponding to the conserved domain sequence of P. alba CCR2), wherein said mutation is present in amino acid position 98, 99, and/or 100 of said domain as depicted in SEQ ID NO:1. The mutation may further be characterized in that it concerns a deletion of at least one of the residues corresponding to position 98, 99, and/or 100 of SEQ ID NO:1. Another embodiment relates to a nucleic acid molecule encoding a mutant plant CCR protein that is mutated in a conserved domain of CCR with a sequence of at least 50% amino acid identity to the domain of SEQ ID NO:1, wherein said mutation is present in the corresponding amino acid aligned to position 98, 99, and/or 100 of said domain depicted in SEQ ID NO:1 (see FIG. 6 for an example of an alignment to identify positions 98, 99 and 100). The mutation may further be characterized in that it concerns a deletion of at least one of the residues corresponding to position 98, 99, and/or 100 of a sequence of at least 50% amino acid identity to the domain of SEQ ID NO:1. Said conserved domain of CCR proteins is defined herein as a conserved domain of a plant CCR protein comprising the hallmark residues for CCR identity and activity present in said protein sequence (as depicted in FIG. 6). Said hallmark residues include the CCR signature 'NWYCYGK', as well as the NADP binding site residues and active site residues as depicted and annotated in the alignment of CCR protein sequences shown in FIG. 6, representing a population of different CCR proteins of a number of plant species. In fact, said conserved domain of CCR proteins as shown for P. alba CCR2 in SEQ ID NO:1 represents the most conserved region of the full protein (lacking a more divergent C-terminal part of about 100 amino acids), and includes the functionally conserved FR_SDR_e domain present in plant CCR proteins, which is responsible for its function in plants.

Indeed, the enzyme CINNAMOYL-COA REDUCTASE (EC 1.2.1.44), systematically named cinnamaldehyde:NADP+oxidoreductase (CoA-cinnamoylating) but commonly referred to by the acronym CCR, is an enzyme that catalyzes the reduction of a substituted cinnamoyl-CoA to its corresponding cinnamaldehyde, utilizing NADPH and H+ and releasing free CoA and NADP+ in the process. Common biologically relevant cinnamoyl-CoA substrates for CCR include p-coumaroyl-CoA and feruloyl-CoA, which are converted into p-coumaraldehyde and coniferaldehyde, respectively, though most CCRs show activity toward a variety of other substituted cinnamoyl-CoA's as well. Catalyzing the first committed step in monolignol biosynthesis, this enzyme plays a critical role in lignin formation, a process important in plants both for structural development and defense response.

The evolutionary relation between different sequences is confined in the terminology of "homology", which describes a divergent evolutionary relationship between genes and proteins based on their sequence similarity/identity, and which descent from a common ancestral DNA sequence. "Orthologues" and "paralogues" encompass evolutionary concepts used to describe the ancestral relationships of genes. Paralogues are genes within the same species that have originated through duplication of an ancestral gene; whereas "orthologues" are genes from different organisms that have originated through speciation, and are also derived from a common ancestral gene. So a "homologue" of a protein encompasses peptides, oligopeptides, polypeptides, proteins and enzymes having amino acid substitutions, deletions and/or insertions relative to the unmodified or wild-type protein in question. "Orthologues" are defined also of having similar biological and functional activity. A functional plant orthologue (or a functional plant orthologous gene) of CCR genes is a plant orthological gene of CCR which encodes a protein with the same enzymatic properties of CCR. Functional orthologues of CCR genes can be isolated from the (publicly) available sequence databases. The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids. The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. A gap, i.e., a position in an alignment where a residue is present in one sequence but not in the other is regarded as a position with non-identical residues. The alignment of the two sequences is performed by the Needleman and Wunsch algorithm (Needleman and Wunsch (1970) *J Mol Biol.* 48: 443-453). The computer-assisted sequence alignment above, can be conveniently performed using standard software program such as GAP which is part of the Wisconsin Package Version 10.1 (Genetics Computer Group, Madison, Wisconsin, USA) using the default scoring matrix with a gap creation penalty of 50 and a gap extension penalty of 3. Sequences are indicated as "essentially similar" or "homologous" when such amino acid sequences have a sequence identity of at least about 70%, particularly at least about 75%, particularly at least about 80%, more particularly at least about 85%, quite particularly about 90%, especially about 95%, more especially about 100%, quite especially are identical. Alternatively the skilled person can isolate homologous plant CCR genes through methods of genetic hybridization. Such methods are well known to the skilled (plant) molecular biologist.

The functional relation between CCR genes between plants as described herein relates to their contribution to lignification. For ease of reference and avoidance of doubt a representative of the CCR protein (protein encoded by the full length coding sequence) is represented by *Arabidopsis thaliana* CCR1 NP_173047 (NCBI Genbank accession), and as derived from the CCR gene encoded by AT1G15950 (TAIR accession, www.arabidopsis.org). In poplar, the CCR2 protein is represented here, with *Populus trichocarpa* CCR2 as shown in the alignment of FIG. 6 (SEQ ID NO:22), and for hybrid *P. tremula×P. alba* the genomic sequence as provided by the Aspen database (Xue et al., 2015; Zhou et al., 2015; http://aspendb.uga.edu/) reveals both CCR2 alleles encoding CCR2 proteins with only difference in 1 amino acid (SEQ ID NO: 6 and 7, resp., encoding CCR2 proteins of SEQ ID NO: 2 and 3, resp.). As disclosed by Sonawane et al. (2013; see also FIG. 6), CCR protein sequences are characterized by the presence of several motifs: a CCR signature (NWYCYGK), as well as conserved NADP active site residues and active site residues, all together present within a conserved domain of CCR proteins present within a flavonoid reductase (FR) extended (e) Short-Chain Dehydrogenase/Reductase and Related Enzymes (SDR) (FR_SDR_e) domain. FIG. 6 (adapted from Sonawane et al., 2013) illustrates the alignment of a number of homologous CCR sequences from different plant species, and the conserved region herein, referred to herein as the most N-terminal part of the conserved FR_SDR_e domain, and is about 190 amino acids, as depicted in SEQ ID NO: 1 for the *Populus alba* CCR2 protein, and corresponds to the region comprising amino acid 16 to 208 from the *P. alba* CCR2 protein sequence as depicted in SEQ ID NO:3.

>SEQ ID NO:1: conserved domain from *Populus alba* CCR2 (comprising the CCR signature and NADP and active site residues of the FR_SDR_e domain as indicated in corresponding domain sequences in FIG. 6) (193 aa; as of aa16 to aa 208 from SEQ ID NO:3)

```
CVTGAGGFIASWMVKLLLDKGYTVRGTARNPADPKNSHLRELEGAQERLT

LCKADLLDYESLKEAIQGCDGVFHTASPVTDDPEEMVEPAVNGTKNVIIA

AAEAKVRRVVFTSSIGAVYMDPNKGPDVVIDESCWSDLEFCKNTKNWYCY

GKAVAEQAAWDMAKEKGVDLVVVNPVLVLGPLLQPTVNASIVH
```

The annotation of the FR-SDR_e domain (Marchler-Bauer et al., 2017) is derived from the action of flavonol reductases in the NADP-dependent reduction of flavonoids, ketone-containing plant secondary metabolites, which have the characteristic active site triad of the SDRs (though not the upstream active site Asn) and a NADP-binding motif that is very similar to the typical extended SDR motif. In addition to the Rossmann fold (alpha/beta folding pattern with a central beta-sheet) core region typical of all SDRs, extended SDRs have a less conserved C-terminal extension of approximately 100 amino acids (not included in SEQ ID NO:1). Extended SDRs are a diverse collection of proteins, and include isomerases, epimerases, oxidoreductases, and lyases; they typically have a TGXXGXXG (SEQ ID NO:60) cofactor binding motif. SDRs are a functionally diverse family of oxidoreductases that have a single domain with a structurally conserved Rossmann fold, an NAD(P)(H)-binding region, and a structurally diverse C-terminal region (the C-terminal region is not included in SEQ ID NO:1).

Sequence identity between different SDR enzymes is typically in the 15-30% range; they catalyze a wide range of activities including the metabolism of steroids, cofactors, carbohydrates, lipids, aromatic compounds, and amino acids, and act in redox sensing. Classical SDRs have an TGXXX[AG]XG (SEQ ID NO:61 and 62) cofactor binding motif and a YXXXK (SEQ ID NO:63) active site motif, with the Tyr residue of the active site motif serving as a critical catalytic residue (Tyr-151, human 15-hydroxyprostaglandin dehydrogenase numbering). In addition to the Tyr and Lys, there is often an upstream Ser and/or an Asn, contributing to the active site; while substrate binding is in the C-terminal region, which determines specificity. The standard reaction mechanism is a 4-pro-S hydride transfer and proton relay involving the conserved Tyr and Lys, a water molecule stabilized by Asn, and nicotinamide.

The positions that are mutated in the mutant CCR protein as described herein are indicated in bold grey label within SEQ ID NO:1, at positions 98, 99 and/or 100, and correspond to positions 113, 114 and/or 115 in CCR2 protein sequences of P. alba (SEQ ID NO:3). A mutation of said Isoleucine(s) (I) and/or Alanine (A) may comprise a deletion, substitution or insertion.

The term "mutant plant CCR protein", as described herein, refers to a plant CCR protein that is different in a number of amino acids as compared to its wild type CCR protein sequence (wherein the wild type refers to the most frequently observed sequence for said species). For P. alba CCR2 mutant proteins, in one embodiment, those amino acids corresponding to position 113, 114 and/or 115 of SEQ ID NO:3, are mutated, resulting in a mutated P. alba CCR2. Said mutations may be insertions, deletion and substitutions. In a specific embodiment, the mutant P. alba CCR2 protein is depicted in SEQ ID NO:4, and specifically comprises a substitution of IA at positions 114 and 115 to one Threonine.

To identify a mutant CCR protein as described herein, the skilled artisan could make an alignment of the mutant CCR protein sequence with the wild type CCR protein sequence originating from the same species, and/or include additional (orthologous) CCR proteins (as shown in FIG. 6). This alignment allows to identify whether a mutant CCR protein is indeed mutated at those positions corresponding to position 113, 114 and/or 115 of CCR2 (as depicted in SEQ ID NO:2 or 3), which are present in a very conserved motif of residues in wild type CCR proteins (see FIG. 6).

In one embodiment, the mutant CCR protein is mutated in a conserved domain of at least 50% amino acid identity to SEQ ID NO:1, which typically refers to the conserved domain of another plant CCR protein or of another plant CCR protein from another pant species, or orthologous CCR, which upon alignment with SEQ ID NO:1 corresponds to said conserved domain, and therefore will be at least 50% identical in its amino acid sequence. In the present application, the reference to 'a sequence with at least 50% identity to SEQ ID NO:1', refers to the aligned SEQ ID NO:1 protein sequence with the mutated sequence, wherein the 50% amino acid identity is calculated as stated above herein, but may exclude the residues 98-100 for the calculation. So the present application refers to nucleic acid molecules encoding a mutant plant CCR protein mutated in position 98, 99, and/or 100 of a sequence with at least 50% identity to SEQ ID NO:1, wherein said 50% is calculated on the alignment of all residues of SEQ ID NO:1 excluding residues 98-100. So in said mutant CCR protein, those conserved residues corresponding to position 98, 99 and/or 100 of SEQ ID NO:1, may be different from the residues at those corresponding positions in SEQ ID NO:1 without contributing to the 50% difference/identity. In alternative embodiments, the nucleic acid molecule of the invention may encode a mutant plant CCR protein that is mutated in the conserved domain of said protein with at least 60% amino acid identity to SEQ ID NO:1, or with at least 70% amino acid identity to SEQ ID NO:1, or at least 75% amino acid identity to SEQ ID NO:1, or at least 80% amino acid identity to SEQ ID NO:1, or at least 85% amino acid identity to SEQ ID NO:1, or at least 90% amino acid identity to SEQ ID NO:1, or at least 95% amino acid identity to SEQ ID NO:1, or at least 97% amino acid identity to SEQ ID NO:1, or at least 99% amino acid identity to SEQ ID NO:1, characterized in that the mutation comprises a deletion of at least one amino acid of position 98 to 100 of said conserved domain. Or wherein said mutation comprises a deletion of one of those 98, 99, or 100 position, or wherein said mutation comprises a deletion and a substitution of one of those residues corresponding to position 98, 99, or 100 upon alignment of those conserved domain protein sequences of said CCR proteins.

So the % amino acid identity is based on the comparison of the residues 1-97 and 100 to 193 of SEQ ID NO:1. As shown in FIG. 6, for a non-limiting number of different plant species CCR proteins, the conserved region corresponding to SEQ ID NO:1 is conserved among other CCR orthologues to at least 50% amino acid identity. Therefore, typically, the mutant CCR protein is a mutant as compared to its native wild type form, to reveal whether it is a mutant CCR protein as defined herein, in the motive at positions 98-100.

Mutation can be a substitution, insertion or deletion of amino acid(s). Specifically, the mutation type is however limited to a mutation that does not result in a full inactivation of the protein (or knock-out of the gene). To produce a mutant CCR protein, recombinant, heterologous, or synthetic protein production is envisaged, as well as targeted mutation of endogenous genes. When mutant plant CCR proteins are in scope to be produced within a plant, a plant can be made suitable for producing said mutant CCR protein in several ways. Plants may be transformed to introduce a vector or expression cassette to recombinantly express the nucleic acid molecule encoding the mutant CCR protein within the plant cells. Alternatively, the endogenous gene encoding the CCR polypeptide may be disrupted or mutated by any method known in the art. For example, the gene is mutated using different technologies, such as, transposon tagging, or alternatively by mutagenizing plants using random or targeted mutagenesis and screening for plants that have a CCR mutation (or the corresponding phenotype of the invention). Additional methods for changing the endogenous CCR genes in the plant are also known in the art and can be similarly applied to the instant invention. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al, (1998) Virology 243:472-481; Okubara, et al, (1994) Genetics 137:867-874 and Quesada, et al, (2000) Genetics 154:421-436, each of which is herein incorporated by reference. In addition, a fast and automatable method for screening for chemically induced mutations, TILLING (Targeting Induced Local Lesions in Genomes), using denaturing HPLC or selective endonuclease digestion of selected PCR products is also applicable to the instant invention (see, McCallum, et al, (2000) Nat. Biotechnol 18:455-457). Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant CCR polypeptide suitable for mutagenesis with the goal to eliminate, reduce or change CCR activity have been described. Such mutants can be isolated according to well-known procedures. Another approach is to apply genome editing (also called gene editing), also referred to herein as 'gene editing means', and refers to a group of technologies that allow to change an organism's, such as a plant or plant cell, its DNA. These technologies allow genetic material to be added, removed, or altered at particular locations in the genome. Several approaches to genome editing have been developed. Significant advances have been made in the last few years towards development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/ CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157; 20050064474; and 20060188987, and WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPs genomic locus. Current methods for targeted insertion of exogenous DNA typically involve co-transformation of plant tissue with a donor DNA polynucleotide containing at least one transgene and a site specific nuclease (e.g., ZFN) which is designed to bind and cleave a specific genomic locus of an actively transcribed coding sequence. This causes the donor DNA polynucleotide to stably insert within the cleaved genomic locus resulting in targeted gene addition at a specified genomic locus comprising an actively transcribed coding sequence.

The CRISPR (Clustered Regularly Interspaced Short Palindromic Repeats)/Cas (CRISPR Associated) nuclease system acts as follows. Briefly, a "CRISPR DNA binding domain" is a short stranded RNA molecule that acting in concert with the CAS enzyme can selectively recognize, bind, and cleave genomic DNA. The CRISPR/Cas system can be engineered to create a double-stranded break (DSB) at a desired target in a genome, and repair of the DSB can be influenced by the use of repair inhibitors to cause an increase in error prone repair. See, e.g., Jinek et al (2012) Science 337, p. 816-821, Jinek et al, (2013), eLife 2:e00471, and David Segal, (2013) eLife 2:e00563). In DNA-free gene editing methods, use is made of Ribonucleoprotein (RNP) particles to edit the genes of interest. Such RNPs comprise for instance a gRNA and a Cas9 protein, and may be delivered into the plant cell using biolistic protoplast transformation (for instance as disclosed in WO2017/070032A1 and WO2016/155482A). Zinc finger, CRISPR and TALE binding domains can be "engineered" to bind to a predetermined nucleotide sequence, for example via engineering (altering one or more amino acids) of the recognition helix region of a naturally occurring zinc finger. Similarly, TALEs can be "engineered" to bind to a predetermined nucleotide sequence, for example by engineering of the amino acids involved in DNA binding (the repeat variable diresidue or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534, 261; see also WO 98/53058; WO 98/53059; WO 98/53060; WO 02/016536 and WO 03/016496 and U.S. Publication Nos. 20110301073, 20110239315 and 20119145940.

Any method known in the art to eliminate or alter a plant CCR gene can be used to generate a plant having a non-functional and/or mutant plant CCR protein. In accordance with the present invention, the expression of the endogenous plant CCR gene is eliminated (e.g. when a knock-out allele is desired) if there are no transcripts or proteins detectable. The activity of a functional CCR protein is "eliminated" or "lacking" according to the invention when it is not detectable by at least one conventionally renowned assay method.

In accordance with the present invention, the expression of the endogenous plant CCR gene is reduced (e.g. if a mutant allele is desired) if the transcript or protein level of the CCR is statistically lower than the transcript or protein level of the same CCR in a plant that has not been genetically modified (transformed) or mutagenized or edited to eliminate/reduce the expression of that CCR. In particular embodiments of the invention, the transcript or protein level of the endogenous CCR in a modified plant according to the invention is less than 90%, less than 80%, less than 70%, less than 60%, more preferably less than 50%, less than 40%, less than 30%, less than 20%, less than 10%, or less than 5% of the protein level of the same CCR in a control plant, which is a plant that is not a mutant or that has not been genetically modified or transformed to reduce the expression of that CCR. The expression level of the endogenous CCR may be measured directly, for example, by assaying for the level of endogenous CCR expressed in the cell or plant, or indirectly, for example, by measuring the endogenous or wild type CCR activity in the cell or plant. However, the latter will not allow to distinguish between endogenous CCR protein activity and activity related to the introduction of a mutant CCR protein. Methods for assessing CCR activity are known in the art and include measuring levels of CCR, or of its enzymatic reaction products made within a cell, which can be recovered and assayed from cell extracts.

In other embodiments, the activity of a functional endogenous CCR protein may be reduced or eliminated by disrupting (for a knock-out allele) or mutating the gene (or genes) encoding CCR. In one embodiment, the endogenous CCR protein is encoded by one or more, or by two or more endogenous CCR genes. Similarly, in another embodiment, in particular plants the endogenous CCR protein is encoded by three or more endogenous CCR genes. In another embodiment, the disruption or knock-out comprises insertion of one or more transposons, where the one or more transposons are inserted into the endogenous CCR gene. In yet another embodiment, the disruption or mutation comprises one or more point mutations in the endogenous CCR gene. The disruption or mutation can be a homozygous disruption or mutation in the CCR gene. In another embodiment, the disruption comprises a frameshift to introduce an early stop codon in said CCR gene. Alternatively, the disruption or mutation is a hetero- or hemizygous disruption or mutation in the CCR gene. In certain embodiments, when more than one CCR gene is involved, there is more than one disruption or knock-out, or more than one mutation, which can include homozygous, heterozygous or a combination of homozygous and heterozygous disruptions or mutations.

Detection of expression products is performed either qualitatively (by detecting presence or absence of one or more products of interest) or quantitatively (by monitoring the level of expression of one or more products of interest). In one embodiment, the expression product is an RNA expression product, a protein, or a metabolic or enzymatic product of the protein activity. Thus, many methods may be used to reduce or eliminate or alter the activity of a CCR protein. More than one method may be used to reduce the activity of a single plant CCR gene. In addition, combinations of methods may be employed to reduce or eliminate or alter the activity of two or more different CCR gene combinations. For instance, one method may include genetic engineering such as gene editing means or transformation, while another method in combination therewith may be sexual crossing or breeding of different plant lines. In a further embodiment, the same methods may be used to reduce or eliminate the activity of another lignin biosynthesis protein in a plant. Moreover, said plant wherein at least one allele is disrupted for its lignin biosynthesis encoding activity may be sufficient to identify novel alleles for lignin traits, i.e. reduce lignin amounts in said plant without yield penalty.

In a specific embodiment, a nucleic acid molecule is envisaged, encoding a mutant plant CCR protein, wherein said nucleic acid molecule is mutated (for instance but not limited to a mutation at nx3 nucleotides), to obtain a CCR mutant protein with lower or altered enzymatic activity. More specifically, said nucleic acid molecule encodes a mutant CCR protein with an enzymatic activity, as determined in a biochemical assay or with a quantitative read-out (for instance of a product made by the enzymatic activity within a cell), which is lower than wild type protein activity, but higher than the knock-out or non-functional CCR, preferably higher than 50% of the wild-type protein activity. In some embodiments, said mutant CCR protein is envisaged to have CCR enzymatic activity that is in a range of 50% to 10% of wild type CCR protein activity, wherein wild type CCR protein activity is also determined in a biochemical or cellular activity assay, and wherein the wild type CCR protein is the corresponding non-mutated CCR protein family member of the same plant species, produced in the same way or in the same expression system as the mutant CCR protein. Alternatively, the mutant CCR protein activity is in a range of 90% to 5% of the wild type CCR protein activity, or in the range of 80% to 10%, or in the range of 70% to 20%, or in the range of 60% to 30%, or in the range of 55% to 40% of wild type CCR protein activity. Preferably, the mutant CCR protein activity is in the range of 60% to 15%, 50% to 10%, 40% to 10%, 40% to 15%, or 30% to 20% relative to the wild type or control CCR enzymatic activity.

In one embodiment of the invention, the nucleic acid molecule of the invention encodes a mutant CCR protein that is mutated at locations corresponding to position 98, 99 and/or 100 of SEQ ID NO:1, or a sequence with 50% amino acid identity of SEQ ID NO:1, wherein said mutation leads to the effect of obtaining a mutant CCR protein that is capable of retaining normal growth in otherwise ccr deficient plants, hence containing a lignin trait. With a lignin trait, it is referred to herein as a trait for reduce lignin amounts, altered lignin composition, altered saccharification efficiency, or related metabolic phenotypes. In a specific embodiment, said mutant CCR protein corresponds to the mutant CCR protein of SEQ ID NO:4 or 5. The amino acids at positions 98, 99 and 100 of SEQ ID NO:1 depict an Isoleucine, an Isoleucine and Alanine, respectively in poplar. The mutant CCR proteins as depicted in SEQ ID NO:4 or 5 show that the Isoleucine at position 99 and the conserved Alanine at position 100 was substituted by just one amino acid, a threonine, in the mutant CCR poplar protein. By those mutations in poplar CCR, a novel plant phenotype was obtained, which demonstrates that the position and/or the type of mutation is inducing an elegant but drastic effect on the protein its activity. The importance of this mutant allele and encoded protein thereof became even more clear when hybrid poplar plants with a single ko allele were generated that were lacking the lignin trait, indicating that simply lowering the CCR protein level to less than 51% is not sufficient to overcome the dwarfism in hybrid poplar. Moreover, another hybrid line with one ko allele and the second allele mutated such that the IIA motif of positions 98-100 was replaced to an IA motif also retained its normal growth, but seems to lack the lignin trait, at least in young trees. This may indicate that already 1 deletion of position 99 or 100 is sufficient to obtain the phenotype described for ccr2 12. So, in one embodiment, the nucleic acid molecule is disclosed that has 1 deletion of the residue corresponding to amino acid 98, 99, or 100 in SEQ ID NO:1, or a sequence with 50% amino acid identity thereof. Another embodiment refers to the mutant wherein the residue at position 100, being alanine in SEQ ID NO:1, is deleted. A further embodiment relates to the nucleic acid wherein the encoded protein is mutated in the sense that at least one of 98, 99, and/or 100 is deleted, and at least one of 98, 99, and/or 100 is substituted. More specifically, wherein the substitution concerns a polar residue, more specifically wherein the substitution concerns residue 99 or 100 and results in a polar amino acid residue. When modelling the mutations at those sites in the CCR protein structure, it became clear that those mutation(s) do not directly influence NADP or substrate binding, and are most likely part of the α4 helix according to the structure of Pan et al. (2014). In fact, the mutations itself do not reveal the mechanism of action to come to the new phenotype, which may indicate that alternative mutations in this conserved region may or may not result in a similar phenotype, depending on the resulting structure and/or activity of the mutant CCR protein upon introduction of said alternative mutations.

The deletion of Isoleucine or Alanine, which is relatively conserved among the plant CCR homologues (e.g. as shown in FIG. 6), as well as the substitution of the Isoleucine or the highly conserved small Alanine residue, in a particular embodiment to a polar amino acid residue (Threonine in SEQ ID NO:4 and 5), represent conserved residue mutations of which one may imagine not only to impact protein activity in poplar CCR2 proteins and in poplar plants, but also in homologous and orthologous CCR proteins as well as in other plant species (for example but not limited to the plant CCR proteins shown in FIG. 6). In fact, while the Isoleucine corresponding to position 98 is Isoleucine, Leucine or Valine, indicating structurally very similar residues, position 99 is slightly more variable among CCR homologues, and also found to be identified as a D, R, N, S, M, or V amino acid. However, by comparing a mutant protein to the native CCR protein sequence of the species of interest to express the mutant CCR protein in, one will get an indication whether the mutation may have a similar effect as presented herein. Finally, the alanine at position 100 of SEQ ID NO:1 seems to be extremely conserved in the motif of IIAAA in this region of CCR, indicating that this may be the most critical, although small, amino acid in this motif. The fact that his alanine is not present in the ccr2 12 encoded mutant CCR protein (see FIG. 4A), hints towards the identification of the root cause of the observed phenotype and related lignin trait. This pinpointing exercise brings along the advantage that plants with endogenous ccr knock-out or other deficiencies leading to lignin traits resulting in dwarfism, could probably retain normal plant growth upon introduction of such a mutant CCR protein of the invention. Said deletion of alanine at position 100 of SEQ ID NO:1, or a substitution of 99, or 100 to another amino acid residue, which is more particular a polar residue, i.e. a threonine, serine, cysteine, tyrosine, asparagine or glutamine residue, that are defined herein as amino acids with polar side chains, will result in a plant of the invention as presented herein.

In a specific embodiment, the mutation of the CCR amino acid corresponding to position 98 or 99 in SEQ ID NO:1 is sufficient for obtaining a mutant CCR protein of the invention, i.e. with the capacity to restore normal growth in a ccr deficient plant. Said mutation of 98 or 99 may include a substitution or a deletion or an insertion of an amino acid. In an alternative embodiment, the mutation of the CCR amino acid corresponding to position 99, and/or 100 in SEQ ID NO:1 is sufficient for obtaining a mutant CCR protein of the invention, i.e. with the capacity to restore normal growth in a ccr deficient plant. In another embodiment, both mutation of the CCR amino acid corresponding to position 99 and 100 in SEQ ID NO:1 are required for obtaining the most pronounced effect such as retaining normal plant growth in a ccr deficient plant. In another specific embodiment, the mutation of the CCR amino acid corresponding to position 100 only in SEQ ID NO:1 is sufficient for obtaining a mutant CCR protein of the invention, i.e. with the capacity to restore normal growth in a ccr deficient plant. In a further embodiment, position 100 is deleted in the CCR protein comprising the sequence as depicted in SEQ ID NO:1 or a sequence with 50% amino acid identity thereof. In another specific embodiment, position 100 is deleted and position 99 is deleted. In another embodiment, position 100, 99, and 98 is deleted. In another embodiment, position 100 and 98 is deleted. In another embodiment, position 100 is deleted and position 98 or 99 is substituted to a different amino acid residue. In another specific embodiment, position 100 is substituted to another amino acid than alanine, and optionally position 99 is substituted to a different amino acid as compared to the wild type CCR protein. Finally, the position 100 may be substituted and position 98 or 99 may be deleted.

Another aspect of the invention relates to the mutant plant CCR protein encoded by the nucleic acid molecule of the invention, or expressed from the vector of the invention. Said mutant CCR protein is defined herein as a mutant CCR as compared to the wild type CCR protein of the same species of origin. The mutation as defined herein concerns the amino acid positions corresponding to the positions 98, 99 and/or 100 upon aligning SEQ ID NO:1 with the conserved domain of the mutant CCR protein of interest. Alternatively, the mutation as defined herein concerns the amino acid positions corresponding to amino acid 113, 114 and/or 115 of SEQ ID NO: 2 or 3, i.e. the mutation concerns a change (insertion, deletion or substitution) of the amino acids that align with the Isoleucine(s) and/or alanine at those positions in the *P. alba* or *P. tremula* CCR2 amino acid sequences. In an alternative embodiment the mutant plant CCR protein of the invention is mutated in a conserved domain corresponding to SEQ ID NO:1 or a conserved domain with at least 50% amino acid identity to SEQ ID NO:1; wherein the mutant plant CCR protein displays an enzymatic activity within a range that is lower than wild type CCR activity, or lower than mono-allelic wild-type plant CCR activity, but higher than the knock-out or non-functional CCR protein, i.e. a range of at least 80-10% of wild type CCR activity, at least 70-15% of wild type CCR activity, at least 60-20% of wild type CCR activity, at least 50-30% of wild type CCR activity, or at least 50-10% of wild type CCR activity.

In another aspect of the invention, a method to produce and/or identify a plant mutant CCR protein capable of restoring growth in a plant with low lignin amounts is envisaged, comprising the steps of: producing plant mutant CCR proteins; determining the CCR enzymatic activity of said mutant CCR proteins using a biochemical assay as compared to ccr2 12-derived mutant and wild type CCR protein activity in said assay; identifying a plant mutant CCR protein wherein the activity is in the range corresponding to the activity of the ccr2 12-derived mutant CCR protein, and lower than wild type CCR protein activity. In a specific embodiment, said mutant CCR protein capable of restoring plant growth in a plant with a lignin trait comprises an enzymatic activity in the range of 90% to 5% of the wild type CCR protein activity, or in the range of 80% to 10%, or in the range of 70% to 20%, or in the range of 60% to 30%, or in the range of 55% to 40% of wild type CCR protein activity. Preferably, the mutant CCR protein activity is in the range of 60% to 15%, 50% to 10%, 40% to 10%, 40% to 15%, or 30% to 20% relative to the wild type or control CCR enzymatic activity.

In fact, the enzymatic activity is basically determined by and dependent on the protein structure. The position and nature of a mutation in the protein will hence decide whether a relatively small or no impact on enzymatic activity is observed for a mutant as compared to a wild type, or whether such a small change of even one amino acid may induce drastic shifts in activity. For instance, Pan et al. (2014) and Prasad et al. (2011) disclosed several CCR mutations, which demonstrate by studying the structure of CCR proteins, that such differences in affecting structure and/or activity of CCR proteins are expected.

Alternatively, a method to produce and/or identify a protein with CCR activity capable of restoring growth in a plant with low lignin amounts is envisaged, comprising the steps of: producing said plant protein; determining the CCR enzymatic activity of said protein using a biochemical assay, and compare to ccr2 12-derived mutant and wild type CCR protein activity in said assay; identifying said protein activity of said protein that is in the range corresponding to the activity of the ccr2 12-derived mutant CCR protein, and lower than wild type CCR protein activity. In a specific embodiment, said identified CCR protein with activity capable of restoring plant growth in a plant with a lignin trait comprises an enzymatic activity in the range of 90% to 5% of the wild type CCR protein activity, or in the range of 80% to 10%, or in the range of 70% to 20%, or in the range of 60% to 30%, or in the range of 55% to 40% of wild type CCR protein activity. Preferably, the mutant CCR protein activity is in the range of 60% to 15%, 50% to 10%, 40% to 10%, 40% to 15%, or 30% to 20% relative to the wild type or control CCR enzymatic activity.

In a particular embodiment, said CCR protein is a wild type protein with altered activity, and is usable for complementation of plants with lignin traits to rescue lignin modification-induced dwarfism.

In another embodiment, a method to produce a plant with a lignin trait (i.e. altered lignin amount and/or composition, and/or saccharification efficiency), and developing as a healthy normal plant is envisaged, comprising the step of introducing a reduced lignin biosynthesis activity in said plant. Specifically, said reduced activity is defined as the enzymatic activity lower than wild type CCR activity in a normal plant, and within the range of at least 10% to maximally 80% of wild type activity. In another embodiment, said reduced activity is in the range of at least 20% to 70% of wild type activity, or in the range of at least 30% to 60% of wild type activity, or 40% to 50% of wild type activity. In a particular embodiment, said reduced activity is obtained for the plant via reducing lignin biosynthesis gene expression in said plant, or via insertion of a mutation and/or disruption in at least 1 allele of said lignin biosynthesis gene of said plant. In the latter case, the reduced activity and phenotype is obtained due to haplo-insufficiency of said allele. In fact, in one embodiment, said allele may be used to complement a knock-out of said lignin biosynthesis gene in the same or another species. In a specific embodiment, said lignin biosynthesis gene is CCR, and said reduced activity is in the range of the ccr212-derived mutant CCR protein activity.

Another aspect relates to a screening method to identify mutant plant CCR proteins capable of restoring growth in a dwarf plant, up to normal growth as compared to wild type, comprising the steps of: introducing a mutation in a plant that has at least one knock-out allele in a lignin biosynthesis gene, preferably in a ccr allele, so as to induce at least one mutation in a second ccr allele of said plant, and screen for plants with normal growth phenotype, i.e. comparable growth as wild type or control plants, and identify the nature of the mutation in said plant second mutant ccr allele. Said identification methods are known by a skilled person and for instance, but not limited to, include PCR on plant genomic DNA, sequencing of plant DNA, or other means. In a particular embodiment, said induction of a mutation in the (second) ccr allele of said plant is performed using gene editing technology. In certain embodiments, said knock-out allele may concern any lignin biosynthesis gene.

Alternatively, a screening method for identifying mutant CCR proteins or for producing plants comprising mutant CCR proteins of the invention is envisaged, comprising the steps of: introducing a mutant CCR construct (using a vector or other means described herein) in a plant with abnormal development or growth (due to lignin trait-induced dwarfism), for instance a plant lacking functional CCR activity (i.e. a plant with disrupted CCR genes); and incubate the tissue or plants and isolate a plant or shoot regenerated from said incubated plant or plant cells, to finally screen for plants with normal growth (but with a lignin trait as compared to controls); and optionally identify the CCR sequence and/or the enzymatic activity of said mutant CCR protein.

Further evidence supporting the potential of the identified ccr2 12 mutant allele i.e. the novel mutant protein encoded by this allele, relates to the level of the CCR enzymatic activity of said mutant CCR2 protein (as depicted in SEQ ID NOs:4 and 5). When CCR activity is lower than wild type, advantageous effects on saccharification for plants comprising said activity are provided, while the activity should also be high enough to avoid a yield penalty when expressed in ccr deficient plants. CCR activity may be determined, for instance but not limited to, its measurement using recombinant CCR protein in an in vitro biochemical assay. Enzyme activity assays for example make use of the substrate feruloyl-CoA, wherein enzymatic conversions are followed by targeted UHPLC-MS analysis of the substrate (feruloyl-CoA), and product (coniferaldehyde) (also see Goffner et al. (1994); Kawasaki et al. (2006)). Similarly, Chao et al. (2017) described a biochemical assay used for CCR activity measurement for which several substrates were tested in the presence of NADPH. Feruloyl-CoA, p-coumaroyl-CoA, caffeoyl-CoA, and sinapoyl-CoA. The assay involves a reduction reaction of substrates of hydroxycinnamoyl-Coenzyme A esters in the presence of NADPH, which is consistent with the reaction of CCR in the biosynthesis pathway. Determination of kinetic parameters is performed spectrophotometrically at 366 nm (Luderitz and Griseback, 1981) to calculate CCR activity using molar absorption coefficients provided by Stöekigt and Zen (1975). Those types of assays allow determination of the activity of the ccr2 12 allele encoded mutant CCR protein as to show a reduced profile in comparison to wild type CCR2 allele encoded CCR2 protein.

From these CCR activity data relating to said mutant CCR proteins, the skilled person is able to easily decide whether a CCR protein falls within the range of activity, or scope of the invention, i.e. within the range of the CCR mutant protein activity that provides for the advantage of lower lignin amounts and higher saccharification when expressed in a ccr-deficient plant, without negatively affecting plant growth or biomass.

So in a specific embodiment, a nucleic acid molecule is envisaged encoding a mutant plant CCR protein, which has a mutation in the CCR conserved domain depicted in SEQ ID NO: 1 or in a plant orthologous CCR conserved domain with at least 50% amino acid identity to SEQ ID NO: 1, further characterized in that said mutant CCR protein further has an enzymatic activity in the range of the ccr212-encoded mutant CCR protein, and lower than wild type CCR activity levels, preferably within a range of 0-50% of wild type activity, as measured in a biochemical assay, or a cellular assay.

Another aspect of the invention relates to an expression vector comprising the nucleic acid of the invention, for expression in a plant cell. The nucleic acid molecule of the invention as such, or in the form of a chimeric gene, to be expressed are preferably present on an expression cassette, and cloned into a vector, which is suitable for transforming *Agrobacterium tumefaciens*, for example pBin19 (Bevan et al (1984) Nucl. Acids Res. 12-8711). The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid. Preferably the vectors comprising the nucleic acid of the invention or the chimeric gene (or genes) of the invention comprise a selectable marker or reporter gene. A "selectable marker", "selectable marker gene" or "reporter gene" includes any gene that confers a phenotype on a cell in which it is expressed to facilitate the identification and/or selection of cells that are transfected or transformed with a chimeric gene construct or vector comprising a chimeric gene construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta™; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example p-glucuronidase, GUS or p-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the plant and the selection method. It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die). Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible.

Another aspect of the invention relates to a plant lacking functional wild type CCR protein, further comprising the nucleic acid molecule or vector of the invention to encode the mutant plant CCR protein of the invention, or comprising the mutant CCR protein of the invention, further characterized in that the plant its size and growth is at least comparable to normal wild type growth. With 'lacking functional wild type CCR protein' as described herein is meant that said plant has no or very little, below 5%, endogenous CCR protein activity involved in lignin synthesis, as compared to the wild type CCR protein activity. Such a plant lacking functional wild CCR protein activity, can be obtained via knock-out of CCR, or via a naturally occurring mutation, or via effective RNAi of CCR in said plant, or via another mutagenesis method (such as insertion mutants). In a preferred embodiment, said plant is stable in lacking this endogenous CCR protein activity. The plant as described herein, lacking said functional wild type CCR protein and further comprising the nucleic acid molecule or vector encoding the mutant plant CCR protein of the invention, will result in a phenotype typical for ccr deficient plants (red xylem coloration, lower lignin amounts, higher saccharification efficiency), and surprisingly retain normal plant growth. The yield drag that is typically observed in complete ccr knock-out plants or plants with other lignin traits, is in fact complemented in this plant of the invention by introducing said mutant plant CCR protein, which is capable of restoring growth defects to a level that the plants can grow normal even though they are not producing normal amounts of lignin. In fact, such mutant plant CCR protein expressed in said plant will contribute to a CCR activity level that is different from wild type CCR protein activity and different to a full ccr knock-out, but balanced (probably with an altered and/or lowered activity up to 50%) to allow the advantageous phenotype and effects present in said plant.

In another embodiment, said plant described herein has at least one knock-out ccr allele, and further comprises the nucleic acid molecule or vector of the invention encoding the mutant plant CCR protein, or comprising the mutant plant CCR protein of the invention, with plant growth being comparable to control or wild type plant growth. It is envisaged here that such plant with at least one knock-out ccr allele, may further have another ccr allele that is not encoding a wild type CCR protein, but encodes by itself the mutant CCR protein. It is also envisaged here that such plant with at least one knock-out ccr allele, is not capable of wild type CCR protein activity anymore, i.e. all ccr alleles may be knocked-out, or additional ccr alleles may affect the level of CCR activity as compared to wild type CCR activity. Said plant with at least one knock-out ccr, but rather with all its ccr alleles knocked-out, will require the introduction (e.g. via plant transformation) of a nucleic acid molecule or vector of the invention, encoding a mutant plant CCR protein, capable of restoring plant growth to a normal level, while retaining the lignin trait typical of ccr deficiency. Additionally, said plant with at least one ccr knock-out allele may also contain other mutant alleles of ccr, resulting in a mutant CCR protein expressed from said mutant alleles of CCR in said plant with reduced or altered CCR activity when compared to the wild-type CCR protein.

Lignin-modified plants, i.e. plants with different amounts or compositions of lignin, that show the highest improvement in saccharification efficiency typically suffer from undesired phenotypes, including biomass and seed yield penalties, called lignin modification-induced dwarfism (Chen and Dixon, 2007; Shadle et al., 2007; Bonawitz and Chapple, 2013; Van Acker et al., 2013, 2014; Vanholme et al., 2013b). Said dwarfed phenotype of lignin-modified plants may be caused by the loss of vessel cell wall integrity, which, in turn, results in the inability of the plant to efficiently transport nutrients and water from the roots to the aerial parts. As a consequence, a collapse of the weakened vessel cells occurs under the negative pressure generated by transpiration, called the irregular xylem (irx) phenotype (Bonawitz and Chapple, 2013). Such irregular vessels have been reported for different plant species (Arabidopsis [*Arabidopsis thaliana*], poplar [*Populus tremula×Populus alba*], and tobacco [*Nicotiana tabacum*]) perturbed in the expression of the lignin biosynthesis genes PHENYLALANINE AMMONIA-LYASE (PAL), CINNAMATE 4-HYDROXY-LASE (C4H), 4-COUMARATE: COENZYME A LIGASE (4CL), HYDROXYCINNAMOYL-COENZYME A SHIKIMATE/QUINATE HYDROXYCINNAMOYL TRANSFERASE (HCT), p-COUMARATE 3-HYDROXYLASE (C3H), CAFFEOYL SHIKIMATE ESTERASE (CSE), CAFFEOYL-COENZYME A O-METHYLTRANSFERASE (CCoAOMT), and CINNAMOYLCOENZYME A REDUCTASE (CCR). In addition, a series of dwarfed cellulose and hemicellulose biosynthesis mutants also exhibit the irx phenotype, revealing another type of traits that may be restored by introducing a mutant CCR protein within said perturbed plant.

Therefore, those gene deficiencies, among others (e.g. also cinnamyl alcohol dehydrogenase (CAD)), are non-limiting examples of alternative traits with the potential to lead to dwarfed plants that are envisaged in the invention. Finally, in *B. napus*, genes were identified to be involved in lignin biosynthesis that also contribute to lodging (resistance) (e.g. glycosyl hydrolase, CYT1, an ERF transcription factor SHINE1,and a LIM transcription factor DAR6), which further suggests that a plant with lignin traits resulting in dwarfism, may benefit to acquire better resistance to lodging in certain plant species by introducing a mutant or weak allele of said defective lignin trait, or alternatively, by the mutant CCR protein of the invention. Finally, lodging traits are often used to reduce plant height, but this obviously could be accompanied by detrimental traits, such as yield loss and susceptibility to disease (Wei et al., 2017). Another embodiment relates to a plant with reduced lignin amounts or altered lignin composition as compared to a control or wild type plant, further comprising the nucleic acid molecule or vector of the invention, or mutant CCR protein of the invention, so that said plant is characterized in that plant growth is comparable to a control or wild type plant. Another embodiment relates to a plant with increased saccharification efficiency and/or reduced or altered lignin amounts or composition as compared to a control or wild type plant, further comprising the nucleic acid molecule or vector of the invention, or mutant CCR protein of the invention, so that said plant is characterized in that plant growth is comparable to a control or wild type plant. In fact, said plants envisage a plant lacking endogenous CCR protein activity, inducing dwarfism, which is subsequently complemented (in its growth phenotype) by introducing the mutant CCR protein of the invention, to come to said plant with comparable growth and size as a wild type or control plant, but still maintaining the lignin trait. Another embodiment envisages said plants which have other lignin biosynthesis defects different than ccr deficiencies, inducing dwarfism, wherein said plant is then further characterized in that it comprises the mutant plant CCR protein of the invention, optionally encoded by the introduced nucleic acid or vector of the invention, to restore the growth defect of said dwarfed plant to normal levels, while the lignin phenotype or trait is retained in said plant.

The term "plant growth" refers to the growth rate and corresponding size of a plant in certain conditions/treatments, e.g. with an altered lignin trait or ccr deficiency, compared to the corresponding wild-type plant. An increased growth rate may be reflected inter alia by or confers an increased biomass production of the whole plant, or an increased biomass production of the aerial parts of a plant, or by an increased biomass production of the underground parts of a plant, or by an increased biomass production of parts of a plant, like stems, leaves, blossoms, fruits, and/or seeds. A prolonged growth comprises survival and/or continued growth of the plant, at the moment when the non-transformed wild type organism shows visual symptoms of deficiency and/or death. Such yield-related traits of a plant comprise, without limitation, the increase of the intrinsic yield capacity of a plant, improved nutrient use efficiency, and/or increased stress tolerance, in particular increased abiotic stress tolerance. Intrinsic yield capacity of a plant can be, for example, manifested by improving the specific (intrinsic) seed yield (e.g. in terms of increased seed/grain size, increased ear number, increased seed number per ear, improvement of seed filling, improvement of seed composition, embryo and/or endosperm improvements, or the like); modification and improvement of inherent growth and development mechanisms of a plant (such as plant height, plant growth rate, pod number, pod position on the plant, number of internodes, incidence of pod shatter, efficiency of nodulation and nitrogen fixation, efficiency of carbon assimilation, improvement of seedling vigour/early vigour, enhanced efficiency of germination (under stressed or non-stressed conditions), improvement in plant architecture, cell cycle modifications, photosynthesis modifications, various signaling pathway modifications, modification of transcriptional regulation, modification of translational regulation, modification of enzyme activities, and the like); and/or the like. The term "plant yield" as used herein generally refers to a measurable product from a plant, particularly a crop. Yield and yield increase (in comparison to a non-transformed starting plant or mutant plant or wild-type plant) can be measured in a number of ways, and it is understood that a skilled person will be able to apply the correct meaning in view of the particular embodiments, the particular crop concerned and the specific purpose or application concerned. In accordance with the invention, changes in different phenotypic traits, such as lignin, may reduce, equalize or improve yield as compared to wild type. Preferably, yield is equal or improved. For example, and without limitation, parameters such as floral organ development, root initiation, root biomass, seed number, seed weight, harvest index, leaf formation, phototropism, apical dominance, and fruit development, are suitable measurements of changed yield. "Crop yield" is defined herein as the number of bushels of relevant agricultural product (such as grain, forage, or seed) harvested per acre. Crop yield is impacted by abiotic stresses, such as drought, heat, salinity, and cold stress, and by the size (biomass) of the plant. The yield of a plant can depend on the specific plant/crop of interest as well as its intended application (such as food production, feed production, processed food production, biofuel, biogas or alcohol production, or the like) of interest in each particular case. Thus, in one embodiment, yield can be calculated as harvest index (expressed as a ratio of the weight of the respective harvestable parts divided by the total biomass), harvestable parts weight per area (acre, square meter, or the like); and the like. The harvest index is the ratio of yield biomass to the total cumulative biomass at harvest. Harvest index is relatively stable under many environmental conditions, and so a robust correlation between plant size and grain yield is possible. Measurements of plant size in early development, under standardized conditions in a growth chamber or greenhouse, are standard practices to measure potential yield advantages conferred by the presence of a transgene or altered trait. Accordingly, the yield of a plant can be altered by one or more of the yield-related phenotypes or traits. For example, yield refers to biomass yield, e.g. to dry weight biomass yield and/or fresh-weight biomass yield. Biomass yield refers to the aerial or underground parts of a plant, depending on the specific circumstances (test conditions, specific crop of interest, application of interest, and the like). In one embodiment, biomass yield refers to the aerial and underground parts. Biomass yield may be calculated as fresh-weight, dry weight or a moisture adjusted basis. Biomass yield may be calculated on a per plant basis or in relation to a specific area (e.g. biomass yield per acre/square meter/or the like).

The plant as described herein, refers to a plant that is particularly useful and includes in particular monocotyledonous and dicotyledonous plants including fodder or forage legumes, ornamental plants, more particularly said plant is a crop, or a cereal, or a woody plant or tree. In a specific embodiment, the invention relates to a woody plant which is a poplar, pine, or *eucalyptus* species. Alternatively, the plant ad described herein in particular refers to shrubs selected from the list comprising *Acacia* spp., *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp, *Artocarpus* spp., *Asparagus officinalis*, *Avena* spp. (e.g. *Avena sativa*, *Avena fatua*, *Avena byzantina*, *Avena fatua* var. *sativa*, *Avena hybrida*), *Averrhoa carambola*, *Bambusa* sp., *Benincasa hispida*, *Bertholletia excelsea*, *Beta vulgaris*, *Brassica* spp. (e.g. *Brassica napus*, *Brassica rapa* ssp. [canola, oilseed rape, turnip rape]), *B. luminifera*, *Cadaba farinosa*, *Camellia* spp., *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Ceratodon purpureus*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g. *Elaeis guineensis*, *Elaeis oleifera*), *Eleusine coracana*, *Eragrostis tef*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g. *Glycine max*, *Soja hispida* or *Soja* max), *Gossypium hirsutum*, *Helianthus* spp. (e.g. *Helianthus annuus*), *Hemerocallis fulva*, *Hevea brasiliensis*, *Hibiscus* spp., *Hordeum* spp. (e.g. *Hordeum vulgare*), *Ipomoea batatas*, *Indigofera tinctoria*, *Jatropha curcas*, *Juglans* spp., *Lactuca sativa*, *Lathyrus* spp., *Lens culinaris*, *Leucaena* spp., *Linum usitatissimum*, *Litchi chinensis*, *Lotus* spp., *Luffa acutangula*, *Lupinus* spp., *Luzula sylvatica*, *Lycopersicon* spp. (e.g. *Lycopersicon esculentum*, *Lycopersicon lycopersicum*, *Lycopersicon pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g. *Oryza sativa*, *Oryza latifolia*), *Panicum miliaceum*, *Panicum virgatum*, *Passiflora edulis*, *Pastinaca sativa*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Picea abies*, *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g. *Solanum tuberosum*, *Solanum integrifolium* or *Solanum lycopersicum*), *Sorghum bicolor*, *Spinacia* spp., *Syzygium* spp., *Tagetes* spp., *Tamarindus indica*, *Theobroma cacao*, *Trifolium* spp., *Tripsacum dactyloides*, *Triticosecale rimpaui*, *Triticum* spp. (e.g. *Triticum aestivum*, *Triticum durum*, *Triticum turgidum*, *Triticum hybernum*, *Triticum macha*, *Triticum sativum*, *Triticum monococcum* or *Triticum vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others.

For certain embodiments, said plant as described herein, relates to a seed or plant cell derived from said plant.

In one embodiment, one ccr allele is knocked-out in said plant, while the other is mutated similar as in poplar ccr2 12. More specifically, the *P. alba* allele is mutated in hybrid *P. tremula*×*P. alba* poplar, or alternatively the *P. tremula* allele is mutated. In one embodiment, it is sufficient that the poplar plant is deficient or reduced in its CCR2 activity, and introduction of a mutant CCR2 nucleic acid sequence allows to produce the mutant CCR2 protein within said plant, to obtain the effect of the invention. Moreover, another embodiment relates to plants other than poplar, such as woody plants (pine, *eucalyptus*, rubber tree, . . . ) or crops (maize, wheat, soybean, . . . ) that are deficient in endogenous CCR activity, for instance through knock-out of ccr, and further comprise a mutant CCR protein of the invention, or a mutant CCR protein that comprises a region of at least 50% amino acid identity to SEQ ID NO:1, to obtain the advantageous phenotype of the plant of the invention. Such mutant CCR protein will not be identical to the endogenous CCR protein amino acid sequence of said plant, but will contain mutations with a similar effect as in ccr212 plants, and/or that provide for a weak allele, with a CCR activity in the range of the activity of the mutant protein produced in ccr212.

A knock-out of CCR alleles may be introduced via the introduction of a frameshift mutation, resulting in an early stop codon. CRISPR/Cas technology allows such targeted mutations using gRNAs. In the poplar hybrids *P. tremula×P. alba*, for instance, the CCR2 alleles differ in 3 bp nucleotides but only 1 amino acid, and the difference in nucleotide sequence thereby allows to target bi-allelic mutations. To screen for additional mutant CCR protein sequences that result in the same effect as the CCR mutant protein of the invention, i.e. CCR-phenotype of lower lignin and increased saccharification, while retaining normal plant growth, a knock-out CRISPR/Cas screen can be designed using a number of different gRNAs, followed by transformation and cultivation on soil, to eventually measure and compare primary plant growth and biomass measurements, in addition to xylem coloration analysis, lignin quantification and saccharification.

The true commercial potential and value for the biorefining purposes of said mutant CCR proteins expressed in said plants with lower lignin phenotypes and normal growth is fully revealed through the characterization of 2 meter-tall poplars. In such tall plants, the degree of lignin reduction and biomass properties are more clear (see examples). In addition to cell wall analysis and saccharification assays, the total xylem CCR2 activity as well as a profiling of the metabolites in such plants confirm the advantages and impact of reduced CCR2 activity. As described herein, CCR activity may be determined using recombinantly produced CCR protein in an in vitro biochemical assay, or by in cell feeding assays, and/or may be investigated in the xylem to reveal or identify whether the CCR activity that is necessary to avoid yield penalties is present in those plants. In that respect, feruloyl-CoA is incubated as a substrate of CCR with purified xylem protein extracts and the abundance of coniferaldehyde (product) and ferulic acid (derivative of feruloyl-CoA, which typically accumulates in case of CCR-deficiency) is specifically measured. Alternatively, metabolite profiling is envisaged in the CCR knock-out plants producing a mutant CCR protein, to provide evidence for huge shifts in the metabolite pool, as was previously described in Vanholme et al. (2012) and De Meester et al. (2018). For example, ferulic-, vanillic-, sinapic- and syringic acid (derivates) accumulate, while the abundance of oligolignols (or monolignol coupling products) is reduced.

It is to be understood that although particular embodiments, specific configurations as well as materials and/or molecules, have been discussed herein for engineered cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1. Knock-Out of CCR2 in Poplar Using the CRISPR/Cas9 System

We modified the lignin content in poplar (*Populus tremula×Populus alba*) by stably knocking out CINNAMOYL-COA REDUCTASE2 (CCR2) using the CRISPR/Cas9 system. To mutate CCR2 in *Populus tremula×P. alba* via CRISPR/Cas9, a gRNA was designed targeting the third exon of both CCR2 alleles (Table 1). This gRNA was cloned into the p201N-Cas9 vector baring a kanamycin-selectable marker gene. After *Agrobacterium*-mediated transformation, eight independent shoots could be generated that survived on kanamycin selective medium. Sequencing the PR-amplified region targeted by the gRNA confirmed that seven shoots carried biallelic frameshift modifications in the CCR2 gene (Table 1). Of the in total 14 CCR2 alleles present in these shoots, seven had a 1-bp insertion, three had a 1-bp deletion, while the other 4 alleles had deletions between 7 and 27 bp. Of the eight regenerated shoots, seven ccr2 poplar lines were severely dwarfed and could barely survive out of the humid conditions of in vitro culture (FIG. 1). The CCR2 alleles of these lines contained either biallelic frameshift mutations (ccr2 6, 7, 8, 14, 15 and 17) or a combination of a monoallelic frameshift mutation and a big deletion (ccr213) (Table 1). All these frameshift mutations introduced premature stop codons in the CCR2 sequences.

Interestingly, ccr2 12 contained a frameshift mutation (1 bp insertion) in the *Populus tremula* allele, while having a deletion of 3 bp in the *Populus alba* allele (Table 1). The 3 bp deletion occurred over 2 codons, resulting in an amino acid change corresponding to a substitution of an Isoleucine and an Alanine for a Threonine in the protein sequence (Table 1, FIG. 4 A).

TABLE 1

Sequence information of the CCR2 locus of ccr2 poplars.

| Line | Target sequence (GN19NGG) | Indel | SEQ ID NO |
|---|---|---|---|
| ccr2 lines (with biallelic frameshift mutations) | | | |
| ccr2 6 | GCAGTGAACGGGACCAAAAATGTGATCATTTGCGGCGG | +1 | 42 |
|  | GCAGTGAACGGGACCAAAAATGTGATCA.--------- | -14 | 43 |
| ccr2 7 | GCAGTGAACGGGACCAAAAATGTGATC-.TTGCGGCGG | -1 | 44 |
|  | GCAGTGAACGGGACCAAAAATGTGAT--------GCGG | -7 | 45 |
| ccr2 8 | GCAGTGAACGGGACCAAAAATGTGATCAATTGCGGCGG | +1 | 46 |
|  | GCAGTGAACGGGACCAAAAATGTGATCAATTGCGGCGG | +1 | 47 |
| ccr2 13 | GCAGTGAACGGGACCAAAAATGTGATCAATTGCGGCGG | +1 | 48 |
|  | GCAGTGAACGGGACCAAAAAT-------.--------- | -27 | 49 |
| ccr2 14 | GCAGTGAACGGGACCAAAAATGTGATCAATTGCGGCGG | +1 | 50 |
|  | GCAGTGAACGGGACCAAAAATGTGATC-.TTGCGGCGG | -1 | 51 |
| ccr2 15 | GCAGTGAACGGGACCAAAAATGTGATCAATTGCGGCGG | +1 | 52 |
|  | GCAGTGAACGGGACCAAAAATGTGATC-.TTGCGGCGG | -1 | 53 |
| ccr2 17 | GCAGTGAACGGGACCAAAAATGTGATCACTTGCGGCGG | +1 | 54 |
|  | GCAGTGAACGGGACCAAAAA--------.TTGCGGCGG | -8 | 55 |
| ccr2 line (with a monoallelic frameshift mutation in 1 allele and an indel of 3 bp in the other allele) | | | |
| ccr2 12 | GCAGTGAACGGGACCAAAAATGTGATCAATTGCGGCGG | +1 | 56 |
|  | GCAGTGAACGGGACCAAAAATGTGATCA.---CGGCGG | -3 | 57 |
| Wild type | GCAGTGAACGGGACCAAAAATGTGATCA.TTGCGGCGG | 0 | 58 |
|  | GCAGTGAACGGGACCAAAAATGTGATCA.TTGCGGCGG | 0 | 59 |

Target sequences of the CRISPR/Cas9 construct of wild type and transgenic lines. Both alleles and the indel patterns are shown. The gRNA (underlined in Table 1; and in SEQ ID NOs 6 and 7) and protospacer adjacent motif (PAM; bold text) sequences are highlighted for the wild type.

Example 2. Ccr2 Poplars Containing Biallelic Frameshift Mutations have a Reduced Lignin Content, Collapsed Vessels and a Dwarfed Phenotype The 7 shoots that carried the biallelic frameshift mutations (ccr2 6, ccr2 7, ccr2 8, ccr2 13, ccr2 14, ccr2 15, ccr2 17) along with their wild-type controls, were micropropagated and grown on MS medium for four months. When compared to wild type, the stems and leaves of ccr2 mutants were significantly smaller (FIG. 1). However, ccr2 stems were visually thicker and their leaves were darker green when compared to the wild type (FIG. 1). When transferred to soil, only 2 out of 7 ccr2 poplars recovered, while almost all wild-type plants survived. The five ccr2 poplars that did not survive the transfer died within 2 weeks as a consequence of molding, leaf-shedding and/or necrosis of the stem. In contrast to wild-type plants, which could grow in normal greenhouse conditions, the surviving ccr2 mutants had to be kept under a dome to create very humid conditions to keep them from dying. After four months in their respective conditions, wild types had stems of about 2 m tall with big leaves, while the surviving ccr2 mutants had stems of about 5 cm tall with small leaves (FIG. 2). Since ccr2 mutants carrying the biallelic frameshift mutations could not/barely survive in the greenhouse, all further analyses were performed on plants that were grown for four months on MS medium (after propagation). To examine the structure of the vessels and study the lignification pattern, cross sections of the stem were treated with ethanol, toluidine blue, Mäule and Wiesner staining or visualized via autofluorescence (FIG. 3). Toluidine blue is a polychromatic dye and can be used to differentially stain polysaccharides (purple) and lignin (blue). Mäule and Wiesner staining and autofluorescence specifically image the lignin. More specifically, the Mäule reagent stains G lignin brown and S lignin red, while the Wiesner reagent stains cinnamaldehydes present in the lignin pink (Pradhan Mitra and Loque, 2014). After removal of the bark, the typical red coloration of the xylem was observed in ccr2 mutants. The ethanol-treated stem sections revealed that this red coloration was associated with the cell wall of xylem cells in ccr2 mutants. Although this coloration interfered with the lignin stainings, both Wiesner and Mäule stained stems showed an overall reduction in lignin deposition in the ccr2 lines when compared to wild type.

As seen in the toluidine blue staining and lignin autofluorescence, the wild-type xylem tissue contained large, open vessels and was heavily lignified. In the ccr2 mutants (containing biallelic frameshift mutations), the vessels were irregularly shaped and collapsed. Finally, in the toluidine blue-stained sections, no cellular structures were visible in wild-type vessels and fibers. By contrast, circle-shaped blue structures appeared within the xylem cells of ccr2 after toluidine-blue staining, which could indicate the presence of phenolic deposits or residual cell content.

Next, the lignin amount and composition of ccr2 mutants (containing biallelic frameshift mutations) was determined (Table 2). After growing for four months on MS medium, wild-type plants reached heights of about 15 cm, while ccr2 mutants had heights between 2-6 cm, making a simple comparison between these genotypes difficult; ccr2 might have characteristics of 'young wood' (because of their reduced height, which might be an indication of a delay in development) or 'old wood' (because ccr2 stems were thicker as compared to those of the wild type). To correct for this, the basal ('old wood') and apical ('young wood') wild-type stem segment were analyzed separately, while ccr2 stems were analyzed in full. Similar as for microscopy, stems were harvested after being grown for four months on MS medium. After debarking, the stems were air-dried. Next, soluble compounds were removed by applying a sequential extraction to produce extract-free cell wall residue (CWR) (Van Acker et al., 2013). No significant differences were found between the basal and apical part of the wild-type stem in % CWR, lignin amount and composition (Table 2). However, ccr2 mutants had, on average, 14% less CWR than the wild type. The AcBr lignin amount, which was determined spectrophotometrically, was reduced with 26% in ccr2 when compared to wild type. Next, the lignin composition was analyzed via thioacidolysis, which allows quantification of the H, G, S and other minor units that are linked by β-O-4 interunit bonds in the lignin polymer. ccr2 lignin released substantially less monomers (H+G+S) than the lignin from wild-type samples. This indicates that the lignin of the ccr2 mutant has fewer β-O-4 interunit bonds and thus is enriched in carbon-carbon (mainly β-5, β-β) interunit bonds. The H monomers were barely detectable in the wild type and comprised only about 1.4-1.5% of the total identified thioacidolysis-released units. By contrast, the ccr2 mutant showed a relative increase in thioacidolysis-released H units by more than threefold. Further, the S/G ratio was decreased for the ccr2 mutant when compared to that of the wild type. Incorporation of ferulic acid (FA), which is a known minor constituent of lignin, is indicated in thioacidolysis by the presence of three markers: two are linked via conventional β-O-4-structures (the β-O-4-FA-I and β-O-4-FA-II units), while the third, derived from the bis-β-O-4-coupling of FA, results in a truncated side chain (Ralph et al., 2008). In agreement with previously reported results for plants deficient in CCR, the relative abundance of β-O-4-linked FA-units I and II was increased in the ccr2 mutant poplars when compared to the levels in the wild type (Leple et al., 2007; Mir Derikvand et al., 2008; Ralph et al., 2008; Van Acker et al., 2014).

TABLE 2

Cell wall characteristics of ccr2 mutants carrying biallelic frameshift mutations.

| | | Lignin content and composition | | | |
|---|---|---|---|---|---|
| Line | CWR (% dry weight) | AcBr lignin (% CWR) | H + G + S | % H | % G |
| Wild type (apical part) | 92.1 ± 1.1$^b$ | 19.0 ± 1.0$^a$ | 9.01 ± 0.54$^a$ | 1.4 ± 0.4$^a$ | 72.9 ± 5.7$^a$ |
| Wild type (basal part) | 89.4 ± 1.9$^b$ | 19.0 ± 0.8$^a$ | 6.89 ± 2.68$^a$ | 1.5 ± 1.3$^a$ | 67.6 ± 5.9$^a$ |
| ccr2 | 77.8 ± 2.2$^b$ | 14.0 ± 1.6$^b$ | 2.80 ± 1.95$^b$ | 5.1 ± 3.0$^b$ | 74.7 ± 4.0$^a$ |

TABLE 2-continued

Cell wall characteristics of ccr2 mutants carrying biallelic frameshift mutations.

| | Lignin content and composition | | | | |
|---|---|---|---|---|---|
| Line | % S | S/G | % β-O-4-FA-I | % β-O-4-FA-II | % bis-β-O-4-FA |
| Wild type (apical part) | 25.5 ± 5.6$^a$ | 0.36 ± 0.10$^a$ | 0.00 ± 0.00$^a$ | 0.00 ± 0.00$^a$ | 0.17 ± 0.04$^a$ |
| Wild type (basal part) | 30.6 ± 7.1$^a$ | 0.46 ± 0.13$^a$ | 0.00 ± 0.00$^a$ | 0.00 ± 0.00$^a$ | 0.21 ± 0.08$^a$ |
| ccr2 | 16.5 ± 3.5$^a$ | 0.22 ± 0.06$^b$ | 2.84 ± 1.52$^b$ | 0.60 ± 0.40$^b$ | 0.23 ± 0.39$^a$ |

The cell wall residue (CWR) (expressed as % of the dry weight) was determined gravimetrically after a sequential extraction. Lignin content was determined with the AcBr assay and expressed as % of the CWR. Lignin composition was determined with thioacidolysis. The sum of H, G, and S units is expressed in μmol g-1 AcBr lignin. The relative proportions of the different lignin units were calculated based on the total thioacidolysis yield (including the minor nonconventional lignin units). S/G was calculated based on the absolute values for S and G (expressed in μmol g-1 AcBr lignin). All values are given as average ± standard deviation. Significance groups represent significant differences at the 0.05 significance level (Dunnett-Hsu adjusted t-test; n = 5 for each group).

In conclusion, the ccr2 lines that carried biallelic frameshift mutations had a 26% reduction in acetyl bromide lignin content and displayed the red xylem phenotype, but also suffered from collapsed vessels and severe yield penalties.

Example 3. Poplar Ccr2 12 has a Red Coloration of the Xylem and No Obvious Growth Defects In contrast to the dwarfed biallelic ccr2 mutants, one ccr2 line carried a frameshift mutation in one CCR2 allele, while in the other CCR2 allele a mutation of −3 bp occurred that resulted in a modification of two amino acids, ccr212 (Table 1, FIG. 4), which resulted in a reduced lignin amount (judged by its red xylem phenotype), without displaying obvious yield penalties when grown in tissue culture, or in soil.

As mentioned before, the used gRNA targets the third exon of both CCR2 alleles present in the genome of poplar. All eight examined plants carried mutations in both CCR2 alleles (Table 1). In ccr212, the 1 bp insertion in one allele resulted into a premature stop codon, and—most likely—a full knock-out of this CCR2 allele. However, the 3 bp deletion in the other allele resulted into 1 amino acid substitution and 1 amino acid deletion in the corresponding protein, while the other amino acids remained unaltered (FIG. 4A). Surprisingly, when grown in in vitro conditions, no differences in height between ccr2 12 and the wild type were observed (FIG. 4B). After propagation and transfer to soil, none of the eleven ccr2 12 plants displayed obvious yield penalties, indicating that the allele carrying the 3 bp deletion is still coding for a protein having (reduced/altered) CCR2 activity. When the trees were harvested after reaching heights of approximately 1.20 m, the typical red coloration of the xylem was observed (FIG. 4C). From the remaining 15 cm basal part of the stem, new shoots developed. After twenty weeks of growth, no significant differences in plant height were observed between the wild type and ccr2 12 (FIG. 4D-E). Moreover, stem mass (fresh weight), dry weight, height, and diameter were equal between the wild-type and the ccr2 12 poplars (Table 3).

TABLE 3

Biomass measurements of ccr2 12 poplars.

| Line | Mass with bark (g) | Mass debarked (g) | Dry weight (g) | Height (cm) | Diameter (mm) |
|---|---|---|---|---|---|
| Wild type | 87.6 ± 7.2 | 57.4 ± 4.5 | 18.85 ± 1.69 | 207.40 ± 4.29 | 11.35 ± 0.29 |
| ccr2 12 | 87.0 ± 5.9 | 57.0 ± 3.9 | 17.61 ± 0.51 | 198.18 ± 1.29 | 11.03 ± 0.09 |

Measurements were performed on poplars grown for 20 weeks in the greenhouse (average height ~2 m). Stem diameter was determined 10 cm above soil level. Fresh weight of the stem (without the leaves) was determined with and without bark. After drying the stems for 2 weeks, the dry weight was determined. No significant differences in height, diameter, fresh and dry weight were found between the wild type and ccr2 12 lines at the 0.05 significance level (two-tailed Student's t-test). The data represent averages of 10 biological replicates for WT, and 11 biological replicates for ccr2 12 ± standard error.

Example 4. Ccr2 12 has an Altered Lignin Amount and Composition

To evaluate the lignocellulosic biomass composition of ccr2 12, the lignin content and composition, together with the cellulose amount, of dried stem material was determined (Table 4). First, soluble compounds were removed from the stems by applying a sequential extraction to produce cell wall residue (CWR). The ccr2 12 poplars had an equal amount of CWR as the WT. Second, the fraction of lignin in these prepared CWRs was determined via the Klason and the acetyl bromide method. The total lignin amount of ccr2 12 was decreased by 10% when compared to the WT. Third, the lignin composition was analyzed via 2D HSQC NMR. Using this technique, we found shifts in the relative amounts of both aromatic lignin units and inter-unit linkage types when ccr2 12 was compared to the WT. More specifically, in ccr2 12, the relative amount of S units was decreased, while that of G units was increased when compared to the WT. Moreover, while the relative frequency of H units remained unaltered, that of p-hydroxybenzoates was increased in ccr2 12 when compared to the WT. Furthermore, ccr2 12 lignin had an increased frequency of -aryl ether linkages, while having a decreased frequency of resinol linkages. Fourth, cellulose content was analyzed via the spectrophotometric Updegraff assay, which showed that the crystalline cellulose content of ccr2 12 did not differ significantly from that of the WT.

TABLE 4

Cell wall composition of wild-type and ccr2 12 plants.

| | Wild type mean ± stdev | ccr2 12 mean ± stdev |
|---|---|---|
| CWR (% dry weight) | 84.2 ± 13.8 | 88.6 ± 0.6 |
| Klason lignin amount (% CWR) | 31.1 ± 1.5 | 27.8 ± 0.9** |
| Acid-insoluble Klason lignin (% CWR) | 29.4 ± 1.5 | 26.0 ± 0.9** |
| Acid-soluble Klason lignin (% CWR) | 1.7 ± 0.1 | 1.8 ± 0.1** |
| Acetyl bromide lignin amount (% CWR) | 17.1 ± 1.3 | 15.4 ± 0.7** |
| Aromatic units (%) | | |
| % S | 61.7 ± 0.7 | 57.6 ± 1.6* |
| % G | 38.0 ± 0.6 | 42.3 ± 1.5* |
| % H | 0.3 ± 0.1 | 0.1 ± 0.1 |
| % pBA | 6.9 ± 0.4 | 12.4 ± 0.7** |
| Inter-unit linkages (%) | | |
| β-aryl ether | 82.4 ± 1.8 | 87.8 ± 1.1* |
| Phenyl coumaran | 3.1 ± 1.0 | 3.9 ± 1.5 |
| Resinol | 14.4 ± 1.5 | 8.2 ± 1.1** |
| Cellulose (% CWR) | 39.6 ± 4.2 | 39.5 ± 4.1 |

Cell wall residue (CWR) was determined as the fraction of material obtained after washes relative to the original dry weight (WT, n = 10; ccr2 12, n = 11). Lignin content was determined by the Klason and acetyl bromide method and expressed as a percentage of CWR (WT, n = 10; ccr2 12, n = 11). Lignin composition was determined in enzyme lignin by 2D HSQC NMR (WT and ccr2 12, n = 3). Crystalline cellulose content was determined by the Updegraff method and expressed as a percentage of CWR (WT, n = 10; ccr2 12, n = ).
**P < 0.01,
*P < 0.05, two-tailed Student's t-test;
stdev, standard deviation.

Example 5. The Ccr2 12 Line has Up to 50% Increase in Saccharification Efficiency as Compared to Wild Type Phenotypic analysis revealed that the lignin content of the ccr212 line is reduced as compared to wild type plants (FIG. 4C). Cell wall analysis confirmed that the lignin content of ccr212 was reduced by 10% when compared to that of the WT (Table 4). Because the lignin amount has a negative effect on the saccharification efficiency, the saccharification potential of ccr212 (grown until reaching heights of 1.20 m and of 2 m) after either acid, alkaline or no pre-treatment was further investigated.

For 1.2 m tall plants, the glucose release expressed as % cell wall residue (% CWR) was measured after 2 h and 48 h, without or with (acid or alkali) pre-treatment, and in case of the ccr2 12 mutants, the percentage of increased glucose yield was at least 30% higher in comparison to the wild type for the alkali pre-treatment, and at least 50% higher in comparison to the wild type for the acid pre-treatment (FIG. 5).

For 2 m tall plants, the glucose yield expressed as % CWR of ccr2 12 was much higher than that of the WT. At the endpoint of the saccharification assay, the glucose yield of ccr2 12 after no, acid and alkaline pretreatment was increased by 35%, 53% and 35%, respectively, when compared to the WT (FIG. 7).

So, with these consistent results, we can conclude that the ccr2 12 line has improved saccharification efficiency, resulting in a valuable lignin trait, and this without any yield drags.

Example 6. Ccr212 Poplars have a Reduced Lignin Amount as a Consequence of the Amino Acid Change Occurring in the Respective *P. alba* CCR2 Allele, and not Due to Haplo-Insufficiency In ccr2 12, the *P. tremula* CCR2 allele contains a frameshift mutation resulting into the introduction of an early stop-codon fully knocking-out this allele. In case of haplo-insufficiency, the ccr2 12 lines have a reduced amount of lignin (largely) as a consequence of the frameshift mutation present in the *P. tremula* CCR2 allele. However, the *P. alba* CCR2 allele of ccr2 12 contains a mutation leading to a small amino acid change potentially influencing the activity of its respective CCR2 protein. Therefore, in case of haplo-sufficiency of the WT *P. alba* CCR2 allele, the reduced amount of lignin in ccr212 is the consequence of the reduced activity caused by the amino acid change in the *P. alba* CCR2 protein.

To test for the haplo-(in)sufficient status of the CCR2 alleles, monoallelic CCR2 knock-out lines were generated. More specifically, a gRNA was designed specifically targeting the fourth exon of either the *P. tremula* or the *P. alba* CCR2 allele. The gRNA was cloned into the p201N-Cas9 vector harboring a kanamycin-selectable marker gene. After *Agrobacterium*-mediated transformation, several independent shoots could be regenerated that survived on kanamycin selective medium. Sequencing the PCR-amplified region targeted by the gRNA confirmed that most shoots were mono-allelically mutated (Table 6), while some had biallelic mutations. Similar to the ccr2 biallelic knock-out poplars generated with the gRNA targeting the third exon of the CCR2 gene (FIGS. 1 and 2, and Table 1), the ccr2 biallelic knock-out poplars generated with the gRNA targeting the fourth exon of the CCR2 gene were also severely dwarfed (Table 7 and FIG. 8).

TABLE 6

Sequence information of the CCR2 locus of monoallelic CCR2 knock-out lines.

| Line | Target sequence (20NGG) *Populus alba* allele | Indel | SEQ ID NO: |
|---|---|---|---|
| P. alba WT | CAGAATTGGTATTGCTATGGAAAGGCGG | 0 | 68 |
| P. tremula WT | CAGAATTGGTATTGCTATGGAAAGGCTG | 0 | 69 |
| A1_1 | CAGAATTGGTATTGCTATGG-----CGGTGGCAGAACAAGCTGCGTGGGATATGGCTAAGGAGAAAG | -5 | 70 |
| | CAGAATTGGTATTGCTATGGAAAGGCTGTGGCAGAACAAGCTGCATGGGATATGGCTAAGGAGAAAG | 0 | 69 |
| A5-2 | CAGAATTGGTATTGC-------AGGCGGTGGCAGAACAAGCTGCGTGGGATATGGCTAAGGAGAAAG | -7 | 71 |
| | CAGAATTGGTATTGCTATGGAAAGGCTGTGGCAGAACAAGCTGCATGGGATATGGCTAAGGAGAAAG | 0 | 69 |
| A6_2 | CAGAATTGGTATTGC-------AGGCGGTGGCAGAACAAGCTGCGTGGGATATGGCTAAGGAGAAAG | -7 | 72 |
| | CAGAATTGGTATTGCTATGGAAAGGCTGTGGCAGAACAAGCTGCATGGGATATGGCTAAGGAGAAAG | 0 | 69 |
| A10_1 | CAGAATTGGTATTGCTATGGAA-GGCGGTGGCAGAACAAGCTGCGTGGGATATGGCTAAGGAGAAAG | -1 | 73 |

TABLE 6-continued

Sequence information of the CCR2 locus of monoallelic CCR2 knock-out lines.

| Line | | Indel | SEQ ID NO: |
|---|---|---|---|
| | CAGAATTGGTATTGCTATGGAAA GGCTGTGGCAGAACAAGCTGCAT GGGATATGGCTAAGGAGAAAG | 0 | 69 |
| A13_1 | CAGAATTGGTATTGCT----AAA GGCGGTGGCAGAACAAGCTGCGT GGGATATGGCTAAGGAGAAAG | -4 | 74 |
| | CAGAATTGGTATTGCTATGGAAA GGCTGTGGCAGAACAAGCTGCAT GGGATATGGCTAAGGAGAAAG | 0 | 69 |
| A14_1 | CAGAATTGGTATTGCTATGGA-- ------GAAAGCACAAGCTGCGT GGGATATGGCTAAGGAGAAAG | -8 | 75 |
| | CAGAATTGGTATTGCTATGGAAA GGCTGTGGCAGAACAAGCTGCAT GGGATATGGCTAAGGAGAAAG | 0 | 69 |
| A26_1 | CAGAATTGGTATTGCTATGGAAA AGGCGGTGGCAGAACAAGCTGCG TGGGATATGGCTAAGGAGAAAG | 1 | 76 |
| | CAGAATTGGTATTGCTATGGAAA .GGCTGTGGCAGAACAAGCTGCA TGGGATATGGCTAAGGAGAAAG | 0 | 69 |

| Line | Target sequence (20NGG) Populus tremula allele | Indel | SEQ ID NO: |
|---|---|---|---|
| P. alba WT | GGC<u>AGAACAAGCTGCGTGGGATATGG</u> CTAAGGAGAAAGGGGTGGAC CTAGTGGTGGTTAACCCAGTGCT G | 0 | 77 |
| P. tremula WT | GGC<u>AGAACAAGCTGCATGGGATATGG</u> CTAAGGAGAAAGGGGTGGAC CTAGTGGTGGTTAACCCAGTGCT G | 0 | 78 |
| T3_2 | GGCAGAACAAGCTGCATGGGATA TGGCTAAGGAGAAAGGGGTGGAC CTAGTGGTGGTTAACCCAGTGCT G | 0 | 77 |
| | GGCAGAACAAGCTGC----GATA TGGCTAAGGAGAAAGGGGTGGAC CTAGTGGTGGTTAACCCAGTGCT G | -4 | 79 |
| T4_1 | GGCAGAACAAGCTGCGTGGGA.T ATGGCTAAGGAGAAAGGGGTGGA CCTAGTGGTGGTTAACCCAGTGC TG | 0 | 77 |
| | GGCAGAACAAGCTGCATGGGAAT ATGGCTAAGGAGAAAGGGGTGGA CCTAGTGGTGGTTAACCCAGTGC TG | 1 | 80 |
| T5_1 | AGAACAAGCTGCGTGGGATATGG CTAAGGAGAAAGGGGTGGACCTA GTGGTGGTTAACCCAGTGCTGGT G | 0 | 77 |
| | GGCAGAACAAGCTGCAT-----A TGGCTAAGGAGAAAGGGGTGGAC CTAGTGGTGGTTAACCCAGTGCT G | -5 | 81 |
| T11_1 | AGAACAAGCTGCGTGGGATATGG CTAAGGAGAAAGGGGTGGACCTA GTGGTGGTTAACCCAGTGCTGGT G | 0 | 77 |
| | GGCAGAACAAGCTGCA------- ----------------------- ---------------------T G | -52 | 82 |
| T16_1 | AGAACAAGCTGCGTGGGATATGG CTAAGGAGAAAGGGGTGGACCTA GTGGTGGTTAACCCAGTGCTGGT G | 0 | 77 |
| | GGCAGAACAAGCTGCAT--GATA TGGCTAAGGAGAAAGGGGTGGAC CTAGTGGTGGTTAACCCAGTGCT G | -2 | 83 |
| T20_1 | GGCAGAACAAGCTGCGTGGGA.T ATGGCTAAGGAGAAAGGGGTGGA CCTAGTGGTGGTTAACCCAGTGC TG | 0 | 77 |
| | GGCAGAACAAGCTGCATGGGAAT ATGGCTAAGGAGAAAGGGGTGGA CCTAGTGGTGGTTAACCCAGTGC TG | 1 | 84 |
| T20_2 | GGCAGAACAAGCTGCGTGGGA.T ATGGCTAAGGAGAAAGGGGTGGA CCTAGTGGTGGTTAACCCAGTGC TG | 0 | 77 |
| | GGCAGAACAAGCTGCATGGGAAT ATGGCTAAGGAGAAAGGGGTGGA CCTAGTGGTGGTTAACCCAGTGC TG | 1 | 85 |

Target sequences of the CRISPR/Cas9 construct of wild type and transgenic lines. Both alleles and the indel patterns are shown. The gRNA is underlined.

TABLE 7

Sequence information of the CCR2 locus of biallelic CCR2 knock-out lines.

| Line | Target sequence (20NGG) Populus alba and Populus tremula KO | Indel | SEQ ID NO: |
|---|---|---|---|
| P. alba WT | GGCGGTGGC<u>AGAACAAGCTGCGTGGGATATGG</u> | — | 86 |
| P. tremula WT | GGCTGTGGC<u>AGAACAAGCTGCATGGGATATGG</u> CTAAGGAGAAAGGGGTGGACCTA GTGGTGGTTAAC | — | 87 |
| T2_1 | GGCGGTGGCAGAACAAGCTGC-- ----.ATATGGCTAAGGAGAAAGG GGTGGACCTAGTGGTGGTTAAC | -5 | 88 |

TABLE 7-continued

Sequence information of the CCR2 locus of
biallelic CCR2 knock-out lines.

| Line | Target sequence (20NGG) Populus alba and Populus tremula KO | Indel | SEQ ID NO: |
|---|---|---|---|
| | GGCTGTGGCAGAACAAGCTGCAT GGGAATATGGCTAAGGAGAAAGG GGTGGACCTAGTGGTGGTTAAC | 1 | 89 |

Target sequences of the CRISPR/Cas9 construct of wild type and transgenic lines. Both alleles and the indel patterns are shown. The gRNA is underlined.

Subsequently, after growing for several weeks in tissue culture, the WT, monoallelic CCR2 knock-outs and ccr2 12 poplars were grown in the greenhouse for 11 weeks. After this growth period, the monoallelic CCR2 knock-out plants and ccr212 were equal to the WT in stem height, diameter, fresh and dry weight (Table 8, FIG. 9). After debarking the harvested stems, the red coloration of the xylem was only present in ccr212 mutants, while being absent in the WT and the monoallelic CCR2 knock-out plants (FIG. 10). The latter already suggests that the lignin amount in the monoallelic CCR2 knock-out plants will be similar to that of the WT.

TABLE 8

Biomass analysis of WT, monoallelic CCR2 knock-out plants and ccr2 12.

| Line | Height (cm) | Fresh weight (g) | Dry weight (g) | Diameter (mm) |
|---|---|---|---|---|
| Wild type | 59.3 ± 2.7 a | 4.9 ± 0.5 a | 1.2 ± 0.2 a | 6.0 ± 0.0 a |
| P. tremula CCR2 KO | 53.9 ± 12.7 a | 3.5 ± 2.4 a | 0.9 ± 0.6 a | 5.0 ± 1.2 a |
| P. alba CCR2 KO | 62.7 ± 7.9 a | 5.5 ± 1.8 a | 1.3 ± 0.5 a | 6.2 ± 0.9 a |
| ccr2 12 | 53.0 ± 4.2 a | 4.0 ± 1.3 a | 0.9 ± 0.3 a | 5.5 ± 0.6 a |

Plants were grown for 11 weeks in the greenhouse. At the time of harvest, the height, fresh weight and diameter of the stem were measured. After drying the stems for 5 days, the dry weight was determined. Different letters represent significant differences at the 0.05 significance level (Scheffe adjusted Student's t test). The data represent averages of 7 biological replicates ± standard deviation.

To validate this, the lignin content of dried stem material was determined. First, soluble compounds were removed from the stems by applying a sequential extraction to produce cell wall residue (CWR). All examined lines had an equal amount of CWR (Table 9). Second, the fraction of lignin in these prepared CWRs was determined via the acetyl bromide method. In line with the xylem coloration phenotype (FIG. 10), the acetyl bromide lignin amount (% CWR) in the monoallelic CCR2 knock-out plants is equal to the WT, while that of the ccr2 12 lines is reduced by ~15% when compared to the WT.

TABLE 9

Determination of the lignin amount in WT, monoallelic CCR2 knock-out plants, ccr2 12 and ccr2 116.

| Line | CWR (% dry weight) | Acetyl bromide lignin amount (ACWR) |
|---|---|---|
| Wild type | 70.63 ± 4.31 a | 16.51 ± 1.19 a |
| P. tremula CCR2 KO | 73.67 ± 2.51 a | 16.43 ± 1.05 a |
| P. alba CCR2 KO | 75.15 ± 2.28 a | 16.13 ± 0.64 a |
| ccr2 12 | 74.44 ± 7.48 a | 13.97 ± 0.82 b |

Cell wall residue (CWR) was determined as the fraction of material obtained after washes relative to the original dry weight. Lignin content was determined by the acetyl bromide method and expressed as a percentage of CWR. Different letters represent significant differences at the 0.05 significance level (Scheffe adjusted Student's t test). For all lines, n = 7.

Taken together, the fact that the mono-allelic CCR2 ko alleles (ko/wt) do not result in a similar lignin phenotype as the ccr2 12 mutant lines (ko/mutant) supports the conclusion that the ccr2 12 lignin trait accompanied by its normal plant growth is caused by the presence of the mutation in the P. alba CCR2 allele, and is not the result of haplo-insufficiency of the P. alba CCR2 allele.

Example 7. Gene Editing in Poplar CCR2 Conserved Motif Further Delineates the Target Residues for Interesting Lignin Traits In ccr2 12, the P. alba CCR2 protein sequence differs in only two amino acids from the WT protein sequence. More specifically, an isoleucine and alanine residue are replaced by one threonine residue (FIG. 4A). As a consequence, the ccr212 poplars have a reduced amount of lignin and a large increase in saccharification efficiency when compared to the WT (Table 4, FIG. 7). In addition, the ligin-trait-induced dwarfism or yield penalty is not present in these mutants, which is of great benefit for its commercial value.

Using the same vector (and thus the same gRNA targeting the same region) to generate ccr2 12, a similar ccr2 line was generated, called ccr2 116. In this line, the P. alba CCR2 allele contains a frameshift mutation (4 bp deletion) resulting into a full knock-out of this allele (Table 10). However, the P. tremula CCR2 allele of ccr2 116 contains a deletion of 3 bp resulting into the deletion of one isoleucine residue (FIG. 11). Interestingly, the latter is the same isoleucine residue that is also mutated in ccr2 12, albeit in a different CCR2 allele. Although also ccr2 116 does not suffer from a yield penalty, at this early growth stage where ccr212 showed the typical CCR deficient red coloration of the xylem, this is not the case for ccr2 116, suggesting that the lignin amount is not reduced in ccr2116 (FIG. 11B). To validate this, the lignin amount in the one available sample of ccr2 116 was determined via the acetylbromide method. The lignin amount per % CWR of ccr2 116 was determined to be 17.5%, which lies within one standard deviation of the 16.51% average of the wild type (Table 9). These results suggests that the amino acid changes occuring in the P. alba CCR2 allele of ccr2 12, which comprises the deletion of a very conserved alanine that is not altered in ccr2 116, alters the structural motif to lead to an altered CCR2 activity (and thus lowering the lignin amount in the respective trees), while still acting sufficiently wild-type-like to maintain its growth and normal plant structure development.

TABLE 10

Sequence information of the CCR2 locus of ccr2 116

| Line | Target sequence (20NGG) biolistics | indel | SEQ ID NO: |
|---|---|---|---|
| P. alba WT | GAAATGGTGGAGCCAGCAGTGAACGG GACCAAAAATGTGATCATTGCGG | 0 | 90 |
| P. tremula WT | GAAATGGTGGAGCCAGCAGTGAACGG GACCAAAAATGTGATCATTGCGG | 0 | 90 |
| ccr2 116 | GAAATGGTGGAGCCAGCAGTGAACGG GACCAAAAATGTGA----TGCGGCGG CTGAGGCCAAAGTCCG | -4 | 91 |

TABLE 10-continued

Sequence information of the CCR2 locus of ccr2 116

| Line | Target sequence (20NGG) biolistics | indel | SEQ ID NO: |
|---|---|---|---|
| | GAAATGGTGGAGCCAGCAGTGAACGG GACCAAAAATGTGAT---TGCGGCGG CTGAGGCCAAAGTCCG | -3 | 92 |

Target sequences of the CRISPR/Cas9 construct of wild type and transgenic lines. Both alleles and the indel patterns are shown. The gRNA is underlined.

Example 8. Recombinant Wild-Type and Mutant CCR2 Protein Activity in Yeast

Based on the lignin amount in ccr212 (see Example 4) and the monoallelic ccr2 knock-out lines (Example 6), it is provided that the mutant P. alba CCR2 in ccr2 12 lines encodes an enzyme with an altered or lower CCR activity as compared to the WT P. alba CCR2 encoded enzyme. To validate this, yeast feeding assays were performed in which the activity of the WT and the mutant P. alba CCR2 protein was further investigated. As the substrate of CCR2, feruloyl-CoA, was not available for feeding the yeast cultures, we had to additionally engineer the yeast cultures to express 4-Coumarate:CoA Ligase (4CL), which can convert ferulic acid to the desired feruloyl-CoA substrate (FIG. 12). Subsequently, CCR2 converts this feruloyl-CoA towards its product coniferaldehyde (FIG. 12).

The activity of the respective CCR2 proteins was judged based on the production of coniferaldehyde. Initially, it was investigated which peaks were diagnostic for the production of coniferaldehyde in yeast cultures. To this end, we analyzed the compounds acquired by feeding both 4CL-expressing and 4CL- and WT P. alba CCR2-expressing yeast cultures with ferulic acid. In the chromatograms of the 4CL-expressing yeast cultures, no coniferaldehyde(-related) peaks could be found (FIG. 13A). However, in the chromatograms originating the 4CL- and WT P. alba CCR2-expressing yeast cultures, a peak identified as coniferaldehyde could be observed (FIG. 13A: (1)). Additionally, two other peaks were found (FIG. 13A: (2) and (3)). As these two peaks were also present in the chromatograms originating from 4CL-expressing yeast fed with coniferaldehyde (FIG. 13B), we can conclude that the coniferaldehyde is metabolized by the yeast cells into these two peaks. Therefore, peak (2) and (3) can be additionally used as diagnostic markers for the presence of coniferaldehyde.

Next, we compared the activity of the WT and mutated P. alba CCR2 protein in subsequent yeast feeding assays. To this end, yeast cultures expressing 4CL and the WT or mutated P. alba CCR2 gene were fed with ferulic acid. In the chromatogram of the compounds originating from the yeast culture expressing the WT P. alba CCR2 protein, the coniferaldehyde and two marker peaks were detected (FIG. 13C: (1), (2) and (3)). In the chromatogram originating from the yeast culture expressing the mutated P. alba CCR2 protein, the coniferaldehyde and two marker peaks were absent (FIG. 13C). Based on this analysis, we concluded that no detectable enzymatic activity was present for the mutant P. alba CCR2 protein, as present in the yeast cells. The heterologously expressed mutant protein may be unstable. However, the observed phenotypes, and the observation in the mono-allelic ko poplar lines demonstrates that the CCR2 mutant protein expressed in planta will have an altered or reduced activity as compared to that of the WT P. alba CCR2 protein, but not a null activity, since this would lead to dwarfism as in the double ko mutants. Potentially, its plant-specific environment involving other interacting proteins allows this subtle alteration.

Discussion

Effect of CCR2 Deficiency in Ccr2 Poplars Carrying Biallelic Frameshift Mutations In poplar, the CCR gene family contains 9 members (Shi et al., 2010). However, only CCR2 is highly expressed in differentiating xylem cells, where it presumably is involved in lignification (Lacombe et al., 1997; Shi et al., 2010). The ccr2 poplars carrying biallelic frameshift mutations generated via CRISPR/Cas9 were severely dwarfed (FIG. 2) and although they could be maintained in tissue culture and survived in vitro propagation, most of them died after transfer to soil. Downregulation of CCR2 using sense and antisense constructs also resulted in stunted plants in 5% of the regenerants (Leple et al., 2007). The latter were probably the plants with the highest reduction in CCR2 expression and could be maintained for up to 7 months in tissue culture, but died upon in vitro propagation and acclimation steps. Therefore, for further analysis of the CCR2 downregulated poplars, trees were chosen that did not show growth defects in the greenhouse. A selection of lines was also planted in field trials. However, the growth of these field-grown CCR2 downregulated poplars was affected, suggesting instability of the CCR2 downregulation (Leple et al., 2007; Van Acker et al., 2014).

In ccr2 poplars with biallelic frameshift mutations, the xylem had a uniformly distributed red coloration and contained collapsed vessels. In both greenhouse- and field-grown CCR2-downregulated poplars, the red xylem phenotype often appeared patchy, as a consequence of the unequal levels of gene silencing in red and white areas (Van Acker et al., 2014). Only the red areas of the stem of CCR2 downregulated poplars had decreased lignin amounts and also contained irregular vessels (Leple et al., 2007; Van Acker et al., 2014). Upon vegetative propagation of these lines, a large variability in the red phenotype was observed among the different propagated plants. This exemplifies one of the advantages of CRISPR/Cas9 over the older sense and antisense approaches to silence genes; CCR activity in ccr2 poplars is stably down in all cells.

The acetyl bromide soluble lignin as a percentage of CWR in the ccr2 poplars carrying biallelic frameshift mutations was decreased with 26% when compared to the wild type. However, we believe this decrease in lignin amount is an underestimation probably as a consequence of increased amounts of UV-absorbing substances that are also detected in this spectrophotometry-based method to quantify lignin, just like was observed for CCR2 downregulated poplars (Van Acker et al., 2014). Here, the total acetyl bromide soluble lignin (per % CWR) was not (in 3 lines) or only modestly (in 1 line, up to 12%) decreased. By contrast, the total Klason lignin content (per % CWR) was significantly reduced by 5-24% in these CCR2 downregulated lines. Unfortunately, due to technical limitations, Klason lignin determinations of the ccr2 poplars were not feasible. The ccr2 poplars carrying biallelic frameshift mutations contained more condensed bounds and had a lower S to G ratio when compared to the wild type. These characteristics are indicative for a delay in the lignification program and are also, to a lesser extent, observed in the red areas of the stem of CCR2 downregulated poplars (Laskar et al., 2006; Leple et al., 2007; Van Acker et al., 2013; De Meester et al., 2018). Next, ccr2 poplars incorporated elevated amounts of ferulic acid into their lignins. Similarly, increased levels of ferulic acid were also observed in the lignins of the CCR2 downregulated poplars, where they could have contributed to the improved processing observed for these wood samples (Leple et al., 2007; Van Acker et al., 2014). Finally, the ccr2 poplars had an increased amount of thioacidolysis-released H-units. This increase was not observed in CCR2 downregulated poplars, but was also seen in ccr1 *Arabidopsis*. In the latter, the transcription of other CCR genes was increased possibly redirecting the flux partially to the formation of H-units, like was suggested for alfalfa as well (Lee et al., 2011; Van Acker et al., 2013). Also in ccr2 poplars, CCR gene family members might take over the function of the mutated CCR2 gene. However, this redundancy was insufficient to produce sufficient amounts of lignin to avoid vascular collapse and to produce a viable plant.

Engineering Low-Lignin without Compromising Biomass Through Fine-Tuning of CCR Activity In this finding, we identified an alternative way to stably lower the amount of total plant lignification by altering and/or reducing (and not knock-out) the activity of the CCR2 gene through mutation of the corresponding coding sequence using CRISPR/Cas9. As CRISPR/Cas9-edited plants have a reasonable chance to be allowed for cultivation without regulation, this approach is highly desirable (Waltz, 2018). Moreover, the mutation present in ccr2 12 provides for an excellent example of an elegant strategy to balance the CCR activity reduction/alteration resulting in a lignin trait without yield issue. Through engineering of a frameshift mutation in one allele, while having 1 amino acid substitution and 1 amino acid deletion in the other allele, the total plant CCR2 activity was significantly reduced, also evidenced from the red coloration of the xylem, without leading to obvious yield penalties. Biomass analysis confirmed that these lines do not suffer from any kind of growth perturbations (up to 2 meters of growth). And finally, saccharification efficiency has been shown to increase significantly, using a pre-treatment, making this very promising towards its relevance as a trait for the bio-refinery.

Methods

Plant Material and Vector Construction

To introduce biallelic mutations in CCR2, a list of 30 protospacers with the N19GG motif specific for the poplar *P. tremula×P. alba* CCR2 alleles was extracted from the Aspen database (Xue et al., 2015; Zhou et al., 2015; http://aspendb.uga.edu/). Next, the possible protospacers were analyzed based on their position in the CCR2 alleles and the possible off-targets via the Aspen database (Xue et al., 2015; Zhou et al., 2015). Additionally, the following requirements were considered: (i) GC-content, and (ii) absence of a TTTTT sequence. Based on these parameters, the most suitable protospacer was chosen: GAAAAATGTGATCATTGCGGCGG (SEQ ID NO:64), in which the first nucleotide was changed into a G (previous a C) to fulfil the needs of the MtU6 promoter. Cloning of the guide RNA (gRNA) in the p201N-Cas9 vector was done as previously described (Jacobs et al., 2015). The p201N Cas9 (Addgene plasmid #59175) and the pUC gRNA Shuttle (Addgene plasmid #47024) were a gift from Wayne Parrott (University of Georgia, Athens, Georgia). For the generation of the ccr2 6, 7, 8, 12, 13, 14, 15, and 17 lines, the resulting p201NCas9: gRNA_CCR2 vector was used. For the empty vector control, the p201N-Cas9 vector, without any inserts, was used for transformation. The expression clones were all transferred into *Agrobacterium tumefaciens* strain C58C1 660 PMP90 by electroporation and positive colonies were selected via PCR. *Agrobacterium*-mediated transformation of *P. tremula×P. alba* 717-1 B4 was performed according to Leple et al. (1992).

For the generation of the ccr2 116 line, biolistic bombardment was used. To this end, the p201NCas9:gRNA_CCR2 plasmid DNA was coated onto gold particles (0.6 μm diameter, Bio-Rad) following the Bio-Rad instruction manual with minor modifications. In summary, under continuous vortex and in the following order, 3 μg of plasmid DNA (1 μg/μL), 50 μL 2.5 M $CaCl_2$ and 1.7 μL 0.1 M spermidine were added to 50 μL aliquots of gold particles (3 mg). Vortexing was continued for 3 minutes, followed by 1-minute centrifugation at 1000 rpm in a microcentrifuge. The supernatant was removed and the beads were washed with 250 μL 100% ethanol before being resuspended in 50 μL 100% ethanol. The DNA-coated microparticles were bombarded into 17-day old poplar callus. Biolistic bombardment was performed using a PDS1000/He particle bombardment system (Bio-Rad) with a target distance of 6 cm from the stopping screen and a helium pressure of 1100 p.s.i. After bombardment, callus tissue was transferred to M3 regeneration medium without selective agents (Leplé et al. 1992) and rested for 24 h in the dark. Upon recovery, the tissue was transferred to M3K selection medium (500 mg/L Kanamycin) and placed at 37° C. for 48 h in the dark. Following the selective treatment, the tissue was transferred to M3 regeneration medium lacking selective agents. After 6-weeks of culture in the light, green micro clusters started to appear, which were manually separated from the mother callus and subcultured on M3 regeneration medium lacking selective agents, and allowed to develop shoots.

To introduce monoallelic mutations in CCR2, specific gRNAs (targeting either the *P. tremula* or the *P. alba* CCR2 allele) were selected based on the criteria described above. The best suitable protospacers chosen here were: GGAACAAGCTGCATGGGATA (SEQ ID NO: 66) to specifically target the *P. tremula* CCR2 allele and GTGGTATTGCTATGGAAAGG (SEQ ID NO: 67) to specifically target the *P. alba* CCR2 allele. Cloning of the gRNA in the p201N-Cas9 vector, subsequent transformation into *Agrobacterium tumefaciens* and poplar transformation were performed as described above.

Plant Growth and Harvest, and the Biomass Analysis

All transgenic plants and their wild-type control were propagated and (first) grown for four months on halfstrength Murashige and Skoog (½ MS) medium in long-day conditions (16-h light/8-h dark photoperiod, 21° C., 55% humidity).

In a first batch of ccr2-12 lines and WT control, seven ccr2 lines (ccr26, 7, 8, 13, 14, 15 and 17) with biallelic frameshift mutations and a similar growth behaviour were treated as one group as compared to WT controls. For microscopy, fresh stems were used. For cell wall analysis, the harvested stems were debarked and dried for three weeks at room temperature. After growing for four months on ½ MS, the plants were transferred to soil and grown for 20 weeks in the greenhouse. For the analysis of biomass parameters, WT (n=10) and ccr2 12 (n=11) plants were grown under a 16-h-light/8-h-dark photoperiod at ±21° C.

When the trees reached heights of approximately 1.20 m, the stem piece ranging from 15-25 cm relative to the bottom of the stem was harvested for saccharification assays. At this height, the red xylem phenotype was observed in the ccr2 12 lines. The remaining basal part of the stem developed new shoots and the trees were measured weekly until they reached a height of 2 meters, after which the diameter of the stems was determined. At the end of the growth period, the diameter of the stems was determined. Next, the stems (10 cm above soil level) were harvested followed by determination of their fresh and dry weights. For cell wall analysis and saccharification, the bottom 50 cm of the harvested stem was debarked, air-dried and ground in a ball mill.

In a second batch of ccr2 12 lines, monoallelic CCR2 knock-out (KO) plants and WT controls, the in vitro-grown plants were transferred to soil and grown for 11 weeks in the greenhouse. For the analysis of the biomass parameters, WT (n=7), *P. tremula* monoallelic CCR2 KO (n=7), *P. alba* monoallelic CCR2 KO (n=7) and ccr212 (n=7) plants were grown under a 16-h-light/8-h-dark photoperiod at ±21° C. The height of the trees was measured weekly until they reached a height of ±60 centimeters. At the end of the growth period, the diameter of the stems was determined. Next, the stems were harvested (5 cm above soil level) followed by determination of their fresh and dry weights. For acetyl bromide analysis, the harvested stem was debarked, air-dried and ground in a ball mill.

Light and Fluorescence Microscopy

For the ccr2 lines and their wild-type control, the bottom 4 cm was embedded in 7% (w/v) agarose and slices of 100 µm thick were made using a vibratome (Campden Instruments, Loughborough, United Kingdom). The sections were imaged in four different conditions: (i) after incubation for 1 h in 100% ethanol, (ii and iii) after incubation with Mäule and Wiesner reagents (as described in Sundin et al. (2014)), (iv) via autofluorescence. For (i), (ii) and (iii) images were acquired using a Zeiss Axioskop 2 microscope with EC Plan—Neofluar 20× (0.5 dry) objective. Lignin autofluorescence (iv) was imaged using the Zeiss LSM 780 microscope with a Plan-Apochromat 10× (0.45 M27) objective. The fluorescence signal for lignin was obtained using 350 nm for excitation and the emission wavelength ranging from 407 to 479 nm.

Cell Wall Characterization

To determine the lignin and cellulose amount, 120 mg of ground powder was used for preparing cell wall residue (CWR) as described previously by Van Acker et al. (2013). Lignin content was determined by the Klason protocol as described by De Meester et al. (2018) and the acetyl bromide protocol as described by Van Acker et al. (2013). For the lignin composition determination via NMR, 200 mg of ground material was analyzed as described in Oyarce et al. (2018). To determine the cellulose amount, the Updegraff method was used (Updegraff et al., 1969).

Saccharification Assays

To measure glucose release (as % cell wall residue (% CWR)), samples were saccharified using no pretreatment, acid pretreatment (0.4 M $H_2SO_4$), or alkaline pretreatment (62.5 mM NaOH). Saccharification was performed as described in Van Acker et al. (2016) on 10 mg of dried, ground stem material. Measurements were performed after 2 h and 48 h of saccharification of 3 month old wild type and ccr2 12 stems (appr. 1.2 m; FIG. 5). In a further experiment, 2 meter tall wild type and ccr212 stems (FIG. 7) were samples wherein the activity of the 10× diluted enzyme mix was 0.14 FPU/mL, and for the alkali pretreatment, the stem material was treated with 1 mL 0.25% (v/v) NaOH at 90° C. for 3 h while shaking at 750 rpm. In case of the acid pretreatment, the stem material was treated with 1 mL of 1 M HCl at 80° C. for 2 h while shaking at 750 rpm.

Yeast Feeding Assays

Yeast W303-1A was transformed via the method described in Gietz and Woods (2006). In total, three different strains were made containing: (1) pAG426GAL:R1-ccdb-R2 (empty vector control)+pAG426GAL:4CL, (2) pAG426GAL:4CL+pAG426GAL:WT_P. alba_CCR2, and (3) pAG426GAL:4CL+pAG426GAL:mutant_P. alba_CCR2. The pAG426GAL vector was acquired from Addgene (Plasmid #14155). The *Malus domestica* 4CL, WT *P. alba* CCR2 and mutant *P. alba* CCR2 gene sequences, codon optimized for yeast and flanked by AttL1 and AttL2 sites, were cloned into the pEN207 vector. For the synthesis of the expression vectors, the respective entry clones (pEN207-L1-4CL-L2, pEN207-L1-WT_P. alba_CCR2-L2 or pEN207-L1-mutant_P. alba_CCR2-L2) were cloned into the pAG426GAL:R1-ccdb-R2 destination vector using LR Clonase (Invitrogen).

For the induction of the yeast culture for gene expression, 5 ml of SD-Ura-Trp medium was inoculated with the respective strain and incubated overnight at 30° C. After centrifugation for 5' at 4000 rpm, the supernatant was discarded. The pellet was resuspended in 1 ml of sterile MQ water and centrifuged for 5' at 4000 rpm. After discarding the supernatant, the pellet was resuspended in 10 ml of SD Gal/Raf-Ura-Trp medium in a falcon tube, vortexed briefly and incubated overnight at 300 rpm.

For feeding the yeast, 500 µl of 20 mM ferulic acid or 500 µl of 20 mM coniferaldehyde was added to each falcon tube and incubated for 2 days at 30° C. and 300 rpm. Next, 1 ml of each yeast culture was harvested and extracted three times with 500 µL of ethyl acetate. The samples were evaporated, derivatized with 10 µL pyridine and 50 µL MSTFA and loaded onto the GC-MS.

```
Sequence listing:

>SEQ ID NO: 1: conserved domain from Populus alba
CCR2 (comprising the CCR signature and NADP and
active site residues of the FR_SDR_e domain as
indicated in corresponding domain sequences in
FIG. 6; position 99-100 in bold) (193 aa; as of
aa 16 to aa 208 from SEQ ID NO: 3)
CVTGAGGFIASWMVKLLLDKGYTVRGTARNPADPKNSHLRELEGAQERLT

LCKADLLDYESLKEAIQGCDGVFHTASPVTDDPEEMVEPAVNGTKNVIIA

AAEAKVRRVVFTSSIGAVYMDPNKGPDVVIDESCWSDLEFCKNTKNWYCY

GKAVAEQAAWDMAKEKGVDLVVVNPVLVLGPLLQPTVNASIVH

Wild type CCR2 proteins of P. tremula x P. alba
hybrids show only 1 AA difference (bold):
>SEQ ID NO: 2: Populus tremula CCR2 protein
sequence (338 aa)
MPVDASSLSGQGQTICVTGAGGFIASWMVKLLLDKGYTVRGTARNPADPK

NSHLRELEGAQERLTLCKADLLDYESLKEAIQGCDGVFHTASPVTDDPEE

MVEPAVNGTKNVIIAAAEAKVRRVVFTSSIGAVYMDPNKGPDVVIDESCW

SDLEFCKNTKNWYCYGKAVAEQAAWDMAKEKGVDLVVVNPVLVLGPLLQP

TVNASIVHILKYLTGSAKTYANSVQAYVHVRDVALAHILVFETPSASGRY

LCSESVLHRGEVVEILAKEFPEYPIPTKCSDEKNPRKQPYKFSNQKLRDL

GFEFTPVKQCLYETVKSLQERGHLPIPKQAAEESVKIQ

>SEQ ID NO: 3: Populus alba CCR2 protein sequence
(338 aa)
MPVDASSLSGQGQTICVTGAGGFIASWMVKLLLDKGYTVRGTARNPADPK

NSHLRELEGAQERLTLCKADLLDYESLKEAIQGCDGVFHTASPVTDDPEE

MVEPAVNGTKNVIIAAAEAKVRRVVFTSSIGAVYMDPNKGPDVVIDESCW
```

Sequence listing:

SDLEFCKNTKNWYCYGKAVAEQAAWDMAKEKGVDLVVVNPVLVLGPLLQP

TVNASIVHILKYLTGSAKTYANSVQAYVHVRDVALAHILVFETPSASGRY

LCSESVLHRGEVVEILAKFFPEYPIPTKCSDEKNPRKQPYKFSNQKLRDL

GFEFTPVKQCLYETVKSLQERGHLPIPKQAAEESLKIQ

Weak allelic mutant CCR2 protein (as present in
the P. alba allele in the ccr2 12)
>SEQ ID NO: 4: Populus alba CCR2 mutant protein
sequence (337 aa)
MPVDASSLSGQGQTICVTGAGGFIASWMVKLLLDKGYTVRGTARNPADPK

NSHLRELEGAQERLTLCKADLLDYESLKEAIQGCDGVFHTASPVTDDPEE

MVEPAVNGTKNVITAAEEAKVRRVVFTSSIGAVYMDPNKGPDVVIDESCWS

DLEFCKNTKNWYCYGKAVAEQAAWDMAKEKGVDLVVVNPVLVLGPLLQPT

VNASIVHILKYLTGSAKTYANSVQAYVHVRDVALAHILVFETPSASGRYL

CSESVLHRGEVVEILAKFFPEYPIPTKCSDEKNPRKQPYKFSNQKLRDLG

FEFTPVKQCLYETVKSLQERGHLPIPKQAAEESLKIQ

>SEQ ID NO: 5: Populus tremula CCR2 mutant protein
sequence (337 aa)
MPVDASSLSGQGQTICVTGAGGFIASWMVKLLLDKGYTVRGTARNPADPK

NSHLRELEGAQERLTLCKADLLDYESLKEAIQGCDGVFHTASPVTDDPEE

MVEPAVNGTKNVITAAEEAKVRRVVFTSSIGAVYMDPNKGPDVVIDESCWS

DLEFCKNTKNWYCYGKAVAEQAAWDMAKEKGVDLVVVNPVLVLGPLLQPT

VNASIVHILKYLTGSAKTYANSVQAYVHVRDVALAHILVFETPSASGRYL

CSESVLHRGEVVEILAKFFPEYPIPTKCSDEKNPRKQPYKFSNQKLRDLG

FEFTPVKQCLYETVKSLQERGHLPIPKQAAEESVKIQ

Wild type genomic CCR2 allelic sequences of P.
tremula × P. alba
>SEQ ID NO: 6: P. alba CCR2 genomic nucleotide
sequence [Potri.003G181400 sPta717alba_v2_gene_
model.fa] (2904 bps) (gRNA overlapping nucleotides
underlined)
GTAACATCCACTTTTTAAGCCAAGATAAGAAGAAAAGACATCTCCTCTCC

TCTTTCTCCCTGTCTGTTCTCCACTTTCCCAGTCACCAAACTCGTATACA

TATAATTACATTTGTCCAAATATAACAACATGCCGGTTGATGCTTCATCT

CTTTCAGGCCAAGGCCAAACTATCTGTGTCACCGGGGCTGGTGGTTTCAT

TGCTTCTTGGATGGTTAAACTTCTTTTAGATAAAGGTTACACTGTTAGAG

GAACTGCGAGGAACCCAGGTTAGTTTATGGTACTTAAGCACTTTTTTTTT

AAAAGATTGTGTTGTTTAATTAATTCAATGGTAGTAGTAATGTTTATGGG

TTGTTTTTCTGTTCTTATATATAAATATATACAGCTGATCCCAAGAATTC

TCATTTGAGGGAGCTTGAAGGAGCTCAAGAAAGATTAACTTTATGCAAAG

CTGATCTTCTTGATTATGAGTCTCTTAAAGAGGCTATTCAAGGGTGTGAT

GGTGTTTTCCACACTGCTTCTCCCGTCACAGATGATCCGGTATGCTTCCC

TTTTCCCTTTGTTTTCCAGTCATTAAAAGATTTGGATCTGAGAATACTAT

CAAGAAAATAAAATAAAATAAAAAACTCACACAGCTAATTTTAGCACAAA

TGTCACTAACTCACGGTAGGCTTGACCGTTCTGCACCAACAAATTCACTT

TGTAGTTGGTGGGTGGAGGGATCAGTTGGGGCCCACCCCACCTAAAACTT

TCGGCAGTGGAATTTCTAATTATAGACGGGTCACTCGAAATTAATAAAAA

TATTACACGGTAATTAATGGTGGTGGTTTTGATGAGATGCTTTTCTTGAC

AATAATTAAAGGAAGAAATGGTGGAGCCAGCAGTGAACGG<u>GACCAAAAAT</u>

<u>GTGATCATTG</u>CGGCGGCTGAGGCCAAAGTCCGACGAGTGGTGTTCACGTC

CTCAATTGGTGCTGTGTACATGGATCCCAATAAGGGCCCAGATGTTGTCA

TTGATGAATCTTGCTGGAGTGATCTTGAATTCTGCAAGAACACCAAGGTA

TCTAATTAATTAAATGCCAAGTTTTCCTTCTTGTGGACCAGTCATATTTC

CTAGCTAACACCTGAACCAATAAATGCTGTGCAATTGAGATGTCAAAGAA

CTTTCATGTATATTTCTTAGACATTTGGCAGGTATAGCTTGCCCGTTCTG

TGTTAAGTTGCCTTATTATAATTGAAATTCACTTAACAAAAAATTGAAC

GAGTCACATCTTTTCTAACCCGTTCTGGTAGCTTTCCATTGATTCGATT

CATACCTAACCTGAGAGTAATGGATTGAAATGAAATGGAATTGCAGAATT

GGTATTGCTATGGAAAGGCGGTGGCAGAACAAGCTGCGTGGGATATGGCT

AAGGAGAAAGGGGTGGACCTAGTGGTGGTTAACCCAGTGCTGGTGCTCGG

ACCATTGTTGCAGCCCACTGTCAATGCTAGCATCGTTCACATCCTCAAGT

ACCTCACCGGCTCAGCCAAGACATATGCTAACTCTGTTCAAGCTTATGTG

CATGTTAGGGATGTGGCACTAGCCCACATTTTAGTCTTTGAGACGCCTTC

CGCCTCCGGCCGTTACCTTTGCTCTGAGAGCGTTCTCCACCGTGGAGAGG

TGGTGGAAATCCTTGCAAAGTTCTTCCCCGAGTACCCCATCCCTACCAAG

TAAGTAATTATTATTTTGAAGAATTTCATGGAGTAATTACTCAATAAAAG

GGTAGTTGGCCGAGTAACAGGCGACACAAATGCATTAAACGTTAGGACAT

GCACTTATGATTAGTCACTCAAAAAAACTACCATCAAAATTGAAAGAAAA

CCTGGGAATGGCATTTTGAAAATGGCAAAACAAATAAATATGATCCTGCT

TTTGAATGACCCAAAGGATGAAATTGTGGTGTGCGGCGGTTGTTGTACCA

GCTTTGACTTGTATTAATCCGAACCAAAAATCAATGAACAATCCATTCTC

CTATGAGTCCTCACCAACCCCATTGTCTGGCAAGTCGGGACCAAAATGAG

TTTCTCTACCAACCCAAGTTATGATTGGACACTGCACAAAATTATTGGAA

GAGTATTGGGCCCGCCCTGCTCCTTCATCTCATACAATTATATGCTAAAT

TCATCTCTCTAAATGTGATTTGCTCAAGATTAGACAAGTGGAAGGAATAT

TCCTAGTTGGTTTGCTACTTGCTAGGTCATAAGAAACAGTTTTGTAATGT

ATTTGCAGGTGCTCAGATGAGAAGAACCCAAGAAAACAACCTTACAAGTT

CTCAAACCAGAAGCTAAGGGATCTGGGCTTGAATTCACACCAGTGAAGC

AGTGTCTGTATGAAACTGTTAAGAGCTTGCAGGAAGGGGTCACCTTCCA

ATCCCAAAACAAGCTGCAGAAGAGTCTCTGAAGATTCAATAAGGCCTCTT

GGAACTATTTATTAGGATACATTTCCATATCCCAAGTTTGGATCGCAAAT

GCTAGGGAAAAGAGCTTATTAAAGAATGTCAATGTGCAGGTGTTTTAGTA

TTTTACATGAAGAACTCTGATTATCCTTGTGTTTATATTAATTTTCTTCA

AGTGAGTGTCTTACACTTGTATTCGTGGCTGTCTAAGTTTATCCAATTTC

Sequence listing:

AATATCGAAGAGGAACAGTTCTATGTCTTACACAAGAGCATCAACTTTGA

CCACACAACTGGCATATGCTTTATTCAATTTAATTGGAGACCTTAACCTA

CATGATAGGTACGCAAATTTCAATCAAGGGAATCCACCAGATATGATGTT

GACGCCATGTATAATCAGAAGATGATTGTATGTTGGTGGAATAATCATCC

TTGTGATATTCAAGTAAGAAAACAAACTCAACAACTATTTAAATAAATAA

AAAA

>SEQ ID NO: 7: P. tremula CCR2 genomic nucleotide sequence [Potri.003G181400 sPta717tremula_v2_gene_model.fa] (2894 bps) (gRNA overlapping nucleotides underlined)

GTAACATCCACTTTTTAAGCCAAGATAAGAAGAAAAGACATCTCCTCTCC

TCTCTCTTTCTGTCTGTTCTCCACTTTCCCAGTCACCAAACTCGTAAACA

TATAATTACATTTATCCAAATATAACAACATGCCTGTTGATGCTTCATCA

CTTTCAGGCCAAGGCCAAACTATCTGTGTCACCGGGGCTGGTGGTTTCAT

TGCTTCTTGGATGGTTAAACTTCTTTTAGATAAAGGTTACACTGTTAGAG

GAACTGCGAGGAACCCAGGTTAGTTAATGGTACTTAAGCACTTTTTTTAA

AAGATTGTGTTGTTTAATTAATTCAATGGTAGTAGTAATGTTATGGGTTG

TTTTTCTGTTCTTATATATAAATATATACAGCTGATCCCAAGAATTCTCA

TTTGAGGGAGCTTGAAGGAGCTCAAGAAAGATTAACTTTATGCAAAGCTG

ATCTTCTTGATTATGAGTCTCTTAAAGAGGCTATTCAAGGGTGTGATGGT

GTTTTCCACACTGCTTCTCCTGTCACAGATGATCCGGTATGCTTCCTTTT

TCCCTTTGCTTTCCAGTCATTAAAAGATTTGGATCTGAGAATATCAAGAA

AAAAAATAATCAAAATAAACTCACACAGCTTATTTTAGCACACATGTCAC

TAACTCACGGTAGGCTTGACCGTTCTGCACCAACAAATTCACTTTGTAGT

TGGTGGGTGGAGGGATCAATTGGGGCCCACCCCACCTAAAACTTTCGGCA

GTGAAATTTCTAATTATAGACGGGTCACTCGAAATTAATAAAATATTACA

TGGTAATTAATGGTGGTGGTTTTGATGAGATGCTTTTGTTGACAATAATT

AAAGGAAGAAATGGTGGAGCCAGCAGTGAACGGGACCAAAAATGTGATCA

TTGCGGCGGCTGAGGCCAAAGTCCGACGAGTGGTGTTCACGTCCTCAATT

GGTGCTGTGTACATGGATCCCAATAAGGGCCCAGATGTTGTCATTGATGA

ATCTTGCTGGAGTGATCTTGAATTCTGCAAGAACACCAAGGTATCTAATT

AATTAAATGCCAAGTTTTCCTTCTTGTCGACTAGTCATATTTTCCAAGCT

AACACCTGAACCAATAAATGCTGTGCAATTGAGATGTCAAAGAATTTTCA

TACATATTTCTTAGACATTTGGTAGGTATAGCTAACCCGTTCTTTGTCAA

GTTGCCTTATTATAATTGAAAATTCACTTTAAAAAAAAATCAACGAGTTG

CATCTTATCTAACCCCGTTCTGGTAGCTGTCCATTGATTCGATTCATACC

TAACCTGAGAGTAATGGATTGAAATGAAATGGAATTGCAGAATTGGTATT

GCTATGGAAAGGCTGTGGCAGAACAAGCTGCATGGGATATGGCTAAGGAG

AAAGGGGTGGACCTAGTGGTGGTTAACCCAGTGCTGGTGCTCGGACCATT

GTTGCAGCCCACTGTCAATGCTAGCATCGTTCACATCCTCAAGTACCTCA

CCGGCTCAGCCAAGACATATGCTAACTCTGTTCAAGCTTATGTGCATGTT

AGGGATGTGGCACTAGCCCACATTTTAGTCTTTGAGACGCCTTCCGCCTC

CGGCCGTTACCTCTGCTCTGAGAGCGTTCTCCACCGTGGGAGAGGTGGTGG

AAATCCTTGCAAAGTTCTTCCCCGAGTACCCCATCCCTACCAAGTAAGTA

ACTATTATTTTGAAGAATTTCATGGAGTAATTACTCAATAAAAGGGTAGT

TGACCGAGTAACAGGCGACACAAATGCATTAAACGTTAGGACATGCACTT

ATGATTAGTCACTCAAAAAAACTACAATCAAAATTGAAAGAAAACCTGGG

AATGGCATTTTGAAAATGGCGAAACAAATAAATATGATCCCGCTTTTGAA

TGACCCAAAGGATGAAATTGTGGTGTGCGGCGGTTGTTGTACCAGCTTTG

ACTTGTATTAATCTGAACCAAAAATCATGAACAATCCATTCTCCTATGAG

TCCTCACCAACCCCATTGTCTGCCAAGTCGGGACCAAAATGAGTTTCTCT

ACCAACCCAAGTTATGATTGGACACTGCACAAAATTATTGGAAGAGTATT

GGGCCCGCCCTGCTCCTTCATCTCATACAATTATATGCTAAATTCATCTC

TCTAAATGTGATTTGCTCAAGATTAGACAAGTGGAAGGAATATTCCTAGT

TGGGTTGCTACTTGCTAGGTCATAAGAAACAGTTCTGTAATGTATTTGCA

GGTGCTCAGATGAGAAGAACCCAAGAAAACAACCTTACAAGTTCTCAAAC

CAGAAGCTAAGGGATCTGGGCTTCGAATTCACACCAGTGAAGCAGTGTCT

GTATGAAACTGTTAAGAGCTTGCAGGAAAGGGGTCACCTTCCAATCCCAA

AACAAGCTGCAGAAGAGTCTGTGAAGATTCAATAAGGCCTCTTGGAACTA

TTTATTAGGATACAGTTCCATACCCCAAGTTTGGATCGCAAATGCTAGGG

AAAAGAGCTTATTAAAGAATGTCAATGTGCAGGTGTTTTAGTATTTTACA

TGAAGAACTCTGATTATCCTTGTGCTTATATTAATTTTCTTCAAGTGAGT

GTCTTACACTTGTATTTGTGGTTGTCTAAGTTTATCCAATTTCAATATCA

AAGAGGAACAGTTCTATGTCTTACACAAGAGCATCAACATTGACCACACA

ACTGGCATATGCTTTATTCAATTTAATTGGAGACCTTAACCTACATGATA

GGTACGCAAATTTCAATCAAGGGAATCCACCAGATATGATGTTGACGCCA

TGTATAATCAGAAGATTGTATATTGGTGGAATAATCATCCTTGTGAT

ATTCAAGTAAGAAAACAAACTCAACAACTATTTAAATAAATAAA

As shown in the alignment of FIG. 6, the amino acid sequences of the CCR proteins from a number of plant species is provided here:

SEQ ID NO:8: amino acid sequence of CCR from *Isatis tinctoria* (ADC40029)
SEQ ID NO:9: amino acid sequence of CCR from *Arabidopsis thaliana* (NP_173047)
SEQ ID NO:10: amino acid sequence of CCR from *Brassica napus* (AEK27166)
SEQ ID NO:11: amino acid sequence of CCR from *Pinus taeda* (AAL47684)
SEQ ID NO:12: amino acid sequence of CCR from *Pinus massoniana* (ACE76870)
SEQ ID NO:13: amino acid sequence of CCR from *Picea abies* (CAK8610)
SEQ ID NO:14: amino acid sequence of CCR from *Leucaena leucocephala* (ABL01801.3)
SEQ ID NO:15: amino acid sequence of CCR from *Leucaena leucocephala* (EU195224)

SEQ ID NO:16: amino acid sequence of CCR from *Eucalyptus saligna* (AF297877_1)
SEQ ID NO:17: amino acid sequence of CCR from *Eucalyptus urophylla* (CBG37721)
SEQ ID NO:18: amino acid sequence of CCR from *Eucalyptus cordata* (AAT74875)
SEQ ID NO:19: amino acid sequence of CCR from *Eucalyptus gunnii* (CAA56103)
SEQ ID NO:20: amino acid sequence of CCR from *Eucalyptus globulus* (AAT74876)
SEQ ID NO:21: amino acid sequence of CCR from *Eucalyptus pilularis* (ACZ59064)
SEQ ID NO:22: amino acid sequence of CCR from *Populus trichocarpa* (CAC07424)
SEQ ID NO:23: amino acid sequence of CCR from *Populus tomentosa* (ACE95172)
SEQ ID NO:24: amino acid sequence of CCR from *Hevea brasiliensis* (ADU64758)
SEQ ID NO:25: amino acid sequence of CCR from *Gossypium hirsutum* (ACQ59094)
SEQ ID NO:26: amino acid sequence of CCR from *Hibiscus cannabinus* (ADK24219)
SEQ ID NO:27: amino acid sequence of CCR from *Betula luminifera* (ACJ38670)
SEQ ID NO:28: amino acid sequence of CCR from *Solanum lycopersicum* (AAY41879)
SEQ ID NO:29: amino acid sequence of CCR from *Solanum tuberosum* (AAN71761)
SEQ ID NO:30: amino acid sequence of CCR from *Codonopsis lanceolate* (BAE48787)
SEQ ID NO:31: amino acid sequence of CCR from *Vaccinium corymbosum* (AC114382)
SEQ ID NO:32: amino acid sequence of CCR from *Fragaria×ananassa* (AAP46143)
SEQ ID NO:33: amino acid sequence of CCR from *Hordeum vulgare* (AAN71760)
SEQ ID NO:34: amino acid sequence of CCR from *Triticum aestivum* (ABE01883)
SEQ ID NO:35: amino acid sequence of CCR from *Saccharum officinarum* (CAA13176)
SEQ ID NO:36: amino acid sequence of CCR from *Zea Mays* (ACG33996)
SEQ ID NO:37: amino acid sequence of CCR from *Panicum virgatum* (ACZ74584)
SEQ ID NO:38: amino acid sequence of CCR from *Cenchrus purpureus* (ADY39751)
SEQ ID NO:39: amino acid sequence of CCR from *Camellia oleifera* (ACQ41893)
SEQ ID NO:40: amino acid sequence of CCR from *Acacia auriculiformis×Acacia mangium* (ADQ53455)
SEQ ID NO:41: amino acid sequence of CCR from *Jatropha curcas* (ACS32301)

As shown in Table 1, several mutant ccr lines were obtained upon editing of hybrid poplar *P. alba×P. tremula*, using the gRNA sequence (underlined in Table 1 and in SEQ ID NO:6 and 7, which represent the genomic sequences of CCR2 from *P. alba* and *P. tremula*, resp.). The SEQ ID Nos (SEQ ID NO:42-57) corresponding to the nucleotide sequences of both mutant alleles of ccr2 as present in the poplar mutant ccr2 lines from Table 1 are indicated in Table 1, and replacing nucleotides 880-916 in SEQ ID NO:6, and/or replacing nucleotides 873-909 in SEQ ID NO:7, and/or the sequences of SEQ ID NO:58-59.

As shown in Table 6, several mono-allelic ko mutant ccr lines were obtained upon editing of hybrid poplar *P. alba×P. tremula*, using the gRNA sequence (underlined in Table 6 in SEQ ID NO:68 and 78). The SEQ 50 ID NOs (SEQ ID NO:70-76) corresponding to the nucleotide sequences of the *P. alba* ko mutant alleles of ccr2 as present in the poplar mutant ccr2lines from Table 6 are indicated, and replacing nucleotides 1349-1371 in SEQ ID NO:6). The SEQ ID NOs 79-85 corresponding to the nucleotide sequences of the *P. tremula* ko mutant alleles of ccr2 as present in the poplar mutant ccr2 lines from Table 6 are indicated, and replacing nucleotides 1370-1392 in SEQ ID NO:7.

As shown in Table 7, biallelic mutant ccr lines were obtained upon editing of hybrid poplar *P. alba×P. tremula*, using the gRNA sequence (underlined in Table 7). The SEQ ID NOs:88-89 corresponding to the nucleotide sequences of both mutant alleles of ccr2 as present in the poplar mutant ccr2 line T2_1 from Table 6 are indicated, and replacing nucleotides 1376-1398 in SEQ ID NO:6, and replacing nucleotides 1369-1391 in SEQ ID NO:7.

As shown in Table 10, the biallelic mutant ccr2 116 line was obtained upon editing of hybrid poplar *P. alba×P. tremula*, using the gRNA sequence (underlined in Table 10). The SEQ ID NOs:91-92 corresponding to the nucleotide sequences of both mutant alleles of ccr2 line 116 from Table 10 are indicated, and replacing nucleotides 865-932 in SEQ ID NO:6, and replacing nucleotides 859-925 in SEQ ID NO:7.

REFERENCES

Besseau S, Hoffmann L, Geoffroy P, Lapierre C, Pollet B, Legrand M (2007) Flavonoid accumulation in *Arabidopsis* repressed in lignin synthesis affects auxin transport and plant growth. Plant Cell 19: 148-162

Boerjan W, Ralph J, Baucher M (2003) Lignin biosynthesis. Annual Review of Plant Biology 54: 519-546

Bonawitz N D, Chapple C (2013) Can genetic engineering of lignin deposition be accomplished without an unacceptable yield penalty? Current Opinion in Biotechnology 24: 336-343

Brendel O, Iannetta P P M, Stewart D W (2000) A rapid and simple method to isolate pure alpha-cellulose. Phytochem Anal 11: 7-10

Carroll A, Somerville C (2009) Cellulosic biofuels. Annu Rev Plant Biol 60: 165-182

Chabannes M, Barakate A, Lapierre C, Marita J M, Ralph J, Pean M, Danoun S, Halpin C, Grima-Pettenati J, Boudet A M (2001) Strong decrease in lignin content without significant alteration of plant development is induced by simultaneous down-regulation of cinnamoyl CoA reductase (CCR) and cinnamyl alcohol dehydrogenase (CAD) in tobacco plants. Plant Journal 28: 257-270

Chao N, Li N, Qi Q, Li S, Lv T, Jiang X-N, Gai Y (2017) Characterization of the cinnamoyl-CoA reductase (CCR) gene family in *Populus tomentosa* reveal the enzymatic active sites and evolution of CCR. Planta 245: 61-75

Chen C, Meyermans H, Burggraeve B, De Rycke R M, Inoue K, De Vleesschauwer V, Steenackers M, Van Montagu M C, Engler G J, Boerjan W A (2000) Cell-specific and conditional expression of caffeoyl-coenzyme A-3-O-methyltransferase in poplar. Plant Physiology 123: 853-867

Chen F, Dixon R A (2007) Lignin modification improves fermentable sugar yields for biofuel production. Nature Biotechnology 25: 759-761

Cullis I F, Mansfield S D (2010) Optimized Delignification of Wood-Derived Lignocellulosics for Improved Enzymatic Hydrolysis. Biotechnology and Bioengineering 106: 884-893

Dauwe R, Morreel K, Goeminne G, Gielen B, Rohde A, Van Beeumen J, Ralph J, Boudet A-M, Kopka J, Rochange S F, et al (2007) Molecular phenotyping of lignin-modified tobacco reveals associated changes in cell-wall metabolism, primary metabolism, stress metabolism and photorespiration. Plant Journal 52: 263-285

De Meester B, de Vries L, Ozparpucu M, Gierlinger N, Corneillie S, Pallidis A, Goeminne G, Morreel K, De Bruyne M, De Rycke R, et al (2018) Vessel-Specific Reintroduction of CINNAMOYL-COA REDUCTASE1 (CCR1) in Dwarfed ccr1 Mutants Restores Vessel and Xylary Fiber Integrity and Increases Biomass. Plant Physiol 176: 611-633

Franke R, Humphreys J M, Hemm M R, Denault J W, Ruegger M O, Cusumano J C, Chapple C (2002) The *Arabidopsis* REF8 gene encodes the 3-hydroxylase of phenylpropanoid metabolism. Plant Journal 30: 33-45

Gao D, Haarmeyer C, Balan V, Whitehead T A, Dale B E, Chundawat S P S (2014) Lignin triggers irreversible cellulase loss during pretreated lignocellulosic biomass saccharification. Biotechnology for Biofuels 7: 175

Gelfand I, Sahajpal R, Zhang X, Izaurralde R C, Gross K L, Robertson G P (2013) Sustainable bioenergy production from marginal lands in the US Midwest. Nature 493: 514-517

Gietz and Woods (2006) Yeast transformation by the LiAc/SS Carrier DNA/PEG method. Methods Mol Biol. 313: 107-20

Gorzsás A, Stenlund H, Perrson P, Trygg J, Sundberg B (2011) Cell-specific chemotyping and multivariate imaging by combined FT-IR microspectroscopy and orthogonal projections to latent structures (OPLS) analysis reveals the chemical landscape of secondary xylem. The Plant Journal 66: 903-914

Goujon T, Ferret V, Mila I, Pollet B, Ruel K, Burlat V, Joseleau J P, Barriere Y, Lapierre C, Jouanin L (2003) Down-regulation of the AtCCR1 gene in *Arabidopsis thaliana*: effects on phenotype, lignins and cell wall degradability. Planta 217: 218-228

Huang J, Gu M, Lai Z, Fan B, Shi K, Zhou Y-H, Yu J-Q, Chen Z (2010) Functional analysis of the *Arabidopsis* PAL gene family in plant growth, development, and response to environmental stress. Plant Physiology 153: 1526-1538

Jackson L A, Shadle G L, Zhou R, Nakashima J, Chen F, Dixon R A (2008) Improving saccharification efficiency of alfalfa stems through modification of the terminal stages of monolignol biosynthesis. BioEnergy Research 1: 180-192

Jacobs T B, LaFayette P R, Schmitz R J, Parrott W A (2015) Targeted genome modifications in soybean with CRISPR/Cas9. BMC biotechnology 15: 16

Jacobs, T. B., Martin, G. B. (2016) High-throughput CRISPR Vector Construction and Characterization of DNA Modifications by Generation of Tomato Hairy Roots. J. Vis. Exp. (110)

Jones L, Ennos A R, Turner S R (2001) Cloning and characterization of irregular xylem4 (irx4): a severely lignin-deficient mutant of *Arabidopsis*. Plant Journal 26: 205-216

Lacombe E, Hawkins S, Van Doorsselaere J, Piquemal J, Goffner D, Poeydomenge O, Boudet A M, Grima-Pettenati J (1997) Cinnamoyl CoA reductase, the first committed enzyme of the lignin branch biosynthetic pathway: cloning, expression and phylogenetic relationships. Plant J 11: 429-441

Laskar D D, Jourdes M, Patten A M, Helms G L, Davin L B, Lewis N G (2006) The *Arabidopsis* cinnamoyl CoA reductase irx4 mutant has a delayed but coherent (normal) program of lignification. Plant Journal 48: 674-686

Lee Y, Chen F, Gallego-Giraldo L, Dixon R A, Voit E O (2011) Integrative analysis of transgenic alfalfa (*Medicago sativa* L.) suggests new metabolic control mechanisms for monolignol biosynthesis. PLoS Comput Biol 7: e1002047

Leplé J-C, Dauwe R, Morreel K, Storme V, Lapierre C, Pollet B, Naumann A, Gilles, Kang K-Y, Kim H, Ruel K, et al (2007) Downregulation of cinnamoyl coenzyme A reductase in poplar; multiple-level phenotyping reveals effects on cell wall polymer metabolism and structure. Plant Cell 19: 3669-3691

Leplé J C, Brasileiro A C M, Michel M F, Delmotte F, Jouanin L (1992) Transgenic poplars: expression of chimeric genes using four different constructs. Plant Cell Reports 11: 137-141

Lüderitz T, Grisebach H (1981) Enzymic synthesis of lignin precursors comparison of cinnamoyl-CoA reductase and cinnamyl alcohol: NADP+ dehydrogenase from spruce (*Picea abies* L.) and soybean (*Glycine max* L.). Eur J Biochem 119: 115-124.

Marchler-Bauer A et al. (2017) CDD/SPARCLE: functional classification of proteins via subfamily domain architectures.Nucleic Acids Res. 45(D1):D200-D203.

Marriott P E, Gómez L D, McQueen-Mason S J (2016) Unlocking the potential of lignocellulosic biomass through plant science. New Phytologist 209: 1366-1381

Petersen P D, Lau J, Ebert B, Yang F, Verhertbruggen Y, Kim J S, Varanasi P, Suttangkakul A, Auer M, Loque D, et al (2012) Engineering of plants with improved properties as biofuels feedstocks by vessel-specific complementation of xylan biosynthesis mutants. Biotechnol Biofuels 5: 84

Pan H, et al. (2014) Structural studies of Cinnamoyl-CoA Reductase and cinnamyl-alcohol dehydrogenase, key enzymes of monolignol biosynthesis. Plant Cell 26: 3709-3727

Piquemal J, Lapierre C, Myton K, O'Connell A, Schuch W, Grima-Pettenati J, Boudet A-M (1998) Down-regulation of cinnamoyl-CoA reductase induces significant changes of lignin profiles in transgenic tobacco plants. Plant J 13: 71-83

Pradhan Mitra P, Loque D (2014) Histochemical staining of *Arabidopsis thaliana* secondary cell wall elements. J Vis Exp Prasad N K et al. (2011) Structural and docking studies of *Leucaena* leucophala cinnamoyl CoA reductase J. Mol. Model 17: 533-541

Rinaldi R, Jastrzebski R, Clough M T, Ralph J, Kennema M, Bruijnincx P C A, Weckhuysen B M (2016) Paving the way for lignin valorisation: Recent advances in bioengineering, biorefining and catalysis. Angewandte Chemie International Edition 55: 8164-8215

Shadle G, Chen F, Reddy M S S, Jackson L, Nakashima J, Dixon R A (2007) Down-regulation of hydroxycinnamoyl CoA: Shikimate hydroxycinnamoyl transferase in transgenic alfalfa affects lignification, development and forage quality. Phytochemistry 68: 1521-1529

Shi R, Sun Y-H, Li Q, Heber S, Sederoff R, Chiang V L (2010) Towards a systems approach for lignin biosynthesis in *Populus trichocarpa*: transcript abundance and specificity of the monolignol biosynthetic genes. Plant & Cell Physiology 51: 144-163

Smith R A, Cass C L, Mazaheri M, Sekhon R S, Heckwolf M, Kaeppler H, De Leon N, Mansfield S D, Kaeppler S M, Sedbrook J C, et al (2017a) Suppression of CIN-NAMOYL-CoA REDUCTASE increases the level of monolignol ferulates incorporated into maize lignins. Biotechnology for Biofuels 10

Smith R A, Schuetz M, Karlen S D, Bird D, Tokunaga N, Sato Y, Mansfield S D, Ralph J, Samuels A L (2017b) Defining the Diverse Cell Populations Contributing to Lignification in *Arabidopsis* Stems. Plant Physiol 174: 1028-1036

Smith R A, Schuetz M, Roach M, Mansfield S D, Ellis B, Samuels L (2013) Neighboring parenchyma cells contribute to *Arabidopsis* xylem lignification, while lignification of interfascicular fibers is cell autonomous. Plant Cell 25: 3988-3999.

Sonawane P, Vishwakarma R K, Khan B M (2013) Biochemical characterization of recombinant cinnamoyl CoA reductase 1 (LI-CCRH1) from *Leucaena leucocephala*. Intntl J. Biol. Macromolec. 58:154-159

Stöekigt J, Zenk M (1975) Chemical syntheses and properties of hydroxycinnamoyl-coenzyme A derivatives. Zeitschrift fir Naturforschung C 30: 352-358

Stout J, Chapple C (2004) The phenylpropanoid pathway in *arabidopsis*: Lessons learned from mutants in sinapate ester biosynthesis. Recent Advances in Phytochemistry 38: 39-67

Sundin L, Vanholme R, Geerinck J, Goeminne G, Höfer R, Kim H, Ralph J, Boerjan W
(2014) Mutation of the inducible *ARABIDOPSIS THALIANA* CYTOCHROME P450 REDUCTASE2 alters lignin composition and improves saccharification. Plant Physiology 166: 1956-1971

Tamasloukht B, Lam M S J W Q, Martinez Y, Tozo K, Barbier O, Jourda C, Jauneau A, Borderies G, Balzergue S, Renou J P, et al (2011) Characterization of a cinnamoyl-CoA reductase 1 (CCR1) mutant in maize: effects on lignification, fibre development, and global gene expression. Journal of Experimental Botany 62: 3837-3848

Van Acker R, Leplé J-C, Aerts D, Storme V, Goeminne G, Ivens B, Légée F, Lapierre C, Piens K, Van Montagu M C E, et al (2014) Improved saccharification and ethanol yield from field-grown transgenic poplar deficient in cinnamoyl-CoA reductase. Proceedings of the National Academy of Sciences of the United States of America 111: 845-850

Van Acker R, Vanholme R, Storme V, Mortimer J C, Dupree P, Boerjan W (2013) Lignin biosynthesis perturbations affect secondary cell wall composition and saccharification yield in *Arabidopsis thaliana*. Biotechnology for Biofuels 6: 46

Van Acker R, Vanholme R, Piens K, Boerjan W (2016) Saccharification protocol for small-scale lignocellulosic biomass samples to test processing of cellulose into glucose. Bio Protoc 6: e1701

Vanholme B, Desmet T, Ronsse F, Rabaey K, Van Breusegem F, De Mey M, Soetaert W, Boerjan W (2013a) Towards a carbon-negative sustainable bio-based economy. Frontiers in Plant Science 4: 174

Vanholme R, Cesarino I, Rataj K, Xiao Y, Sundin L, Goeminne G, Kim H, Cross J, Morreel K, Araujo P, et al (2013b) Caffeoyl shikimate esterase (CSE) is an enzyme in the lignin biosynthetic pathway in *Arabidopsis*. Science 341: 1103-1106

Vanholme R, Demedts B, Morreel K, Ralph J, Boerjan W (2010) Lignin biosynthesis and structure. Plant Physiology 153: 895-905

Vanholme R, Morreel K, Darrah C, Oyarce P, Grabber J H, Ralph J, Boerjan W (2012) Metabolic engineering of novel lignin in biomass crops. New Phytologist 196: 978-1000

Vargas L, Cesarino I, Vanholme R, Voorend W, de Lyra Soriano Saleme M, Morreel K, Boerjan W (2016) Improving total saccharification yield of *Arabidopsis* plants by vessel-specific complementation of caffeoyl shikimate esterase (cse) mutants. Biotechnol Biofuels 9: 139

Voelker S L, Lachenbruch B, Meinzer F C, Jourdes M, Ki C, Patten A M, Davin L B, Lewis N G, Tuskan G A, Gunter L, et al (2010) Antisense down-regulation of 4CL expression alters lignification, tree growth, and saccharification potential of field-grown poplar. Plant Physiol 154: 874-886

Waltz E (2018) With a free pass, CRISPR-edited plants reach market in record time. Nat Biotechnol 36: 6-7

Wang Y, Chantreau M, Sibout R, Hawkins S (2013) Plant cell wall lignification and monolignol metabolism. Frontiers in Plant Science 4: 220

Wei et al (2017) Genetic and transcriptomic analyses of lignin- and lodging-related traits in *Brassica napus* Theor Appl Genet 130:1961-1973

Xue L-J, Alabady M S, Mohebbi M, Tsai C-J (2015) Exploiting genome variation to improve next-generation sequencing data analysis and genome editing efficiency in *Populus tremula*. Tree genetics & genomes 11: 82

Yang F, Mitra P, Ling Z, Prak L, Verhertbruggen Y, Kim J-S, Sun L, Zheng K, Tang K, Auer M, et al (2013) Engineering secondary cell wall deposition in plants. Plant Biotechnology Journal 11: 325-335

Zeng Y, Zhao S, Yang S, Ding S-Y (2014) Lignin plays a negative role in the biochemical process for producing lignocellulosic biofuels. Current Opinion in Biotechnology 27: 38-45

Zhong R, Morrison W H, Negrel J, Ye Z-H (1998) Dual methylation pathways in lignin biosynthesis. Plant Cell 10: 2033-2045

Zhou X, Jacobs T B, Xue L J, Harding S A, Tsai C J (2015) Exploiting SNPs for biallelic CRISPR mutations in the outcrossing woody perennial *Populus* reveals 4-coumarate:CoA ligase specificity and redundancy. New Phytologist 208: 298-301

The invention claimed is:

1. A nucleic acid molecule encoding a mutant plant cinnamoyl-coA reductase (CCR) protein,
   wherein the encoded mutant plant CCR protein is mutated in a conserved domain having the sequence of SEQ ID NO:1, or in a domain having at least 70% amino acid identity with the conserved domain, and
   wherein the mutation comprises a deletion of at least one amino acid at a position corresponding to one of position(s) 98 to 100 of the conserved domain or the domain having at least 70% amino acid identity with the conserved domain.

2. The nucleic acid molecule of claim 1, wherein the encoded mutant plant CCR protein has a deletion at the amino acid residue corresponding to position 100 of the conserved domain, or in a domain having at least 70% amino acid identity with the conserved domain.

3. The nucleic acid molecule of claim 1, wherein the encoded mutant plant CCR protein further comprises a substitution of at least one amino acid residue at a position corresponding to one of position 99 or 100 of the conserved domain, or the domain having at least 70% amino acid identity with the conserved domain.

4. The nucleic acid molecule of claim 3, wherein the substitution of the residue at a position corresponding to one of position 99 or 100 is a substitution for a polar amino acid residue.

5. The nucleic acid molecule of claim 1, wherein the nucleic acid molecule is comprised in an expression vector for expression in a plant cell.

6. The mutant plant CCR protein encoded by the nucleic acid molecule of claim 1.

7. The nucleic acid molecule of claim 1, wherein the nucleic acid molecule is comprised in a plant lacking a functional wild-type CCR protein and characterized in that plant growth is at least equal to a control plant comprising a wild-type CCR protein level.

8. The nucleic acid molecule of claim 1, wherein the nucleic acid molecule is comprised in a plant with at least one knocked-out ccr allele and characterized in that plant growth is at least equal to a control plant comprising a wild-type CCR protein level.

9. The nucleic acid molecule of claim 7, wherein lignin amounts are lower in the plant comprising the nucleic acid molecule as compared to the control plant.

10. The nucleic acid molecule of claim 7, wherein the saccharification efficiency in the plant comprising the nucleic acid molecule is higher as compared to the control plant.

11. The nucleic acid molecule of claim 7, wherein the plant comprising the nucleic acid molecule is a crop, a cereal plant, or a woody plant.

12. A method to produce a plant with restored growth and a lignin trait, the method comprising:
   a. introducing the nucleic acid molecule of claim 1 into a plant with abnormal growth or abnormal growth in its cells, and
   b. isolating and incubating a plant regenerated from said plant, and
   c. determining that the regenerated plant has restored growth.

13. The nucleic acid molecule of claim 8, wherein lignin amounts are lower in the plant comprising the nucleic acid molecule as compared to the control plant.

14. The nucleic acid molecule of claim 8, wherein the saccharification efficiency in the plant comprising the nucleic acid molecule is higher as compared to the control plant.

15. The nucleic acid molecule of claim 8, wherein the plant comprising the nucleic acid molecule is a crop, a cereal plant, or a woody plant.

* * * * *

SEQUENCE LISTING

<160> NUMBER OF SEQ ID NOS: 93

<210> SEQ ID NO 1
<211> LENGTH: 193
<212> TYPE: PRT
<213> ORGANISM: Populus alba

<400> SEQUENCE: 1

```
Cys Val Thr Gly Ala Gly Gly Phe Ile Ala Ser Trp Met Val Lys Leu
1               5                   10                  15

Leu Leu Asp Lys Gly Tyr Thr Val Arg Gly Thr Ala Arg Asn Pro Ala
            20                  25                  30

Asp Pro Lys Asn Ser His Leu Arg Glu Leu Glu Gly Ala Gln Glu Arg
            35                  40                  45

Leu Thr Leu Cys Lys Ala Asp Leu Leu Asp Tyr Glu Ser Leu Lys Glu
50                  55                  60

Ala Ile Gln Gly Cys Asp Gly Val Phe His Thr Ala Ser Pro Val Thr
65                  70                  75                  80

Asp Asp Pro Glu Glu Met Val Glu Pro Ala Val Asn Gly Thr Lys Asn
            85                  90                  95

Val Ile Ile Ala Ala Ala Glu Ala Lys Val Arg Arg Val Val Phe Thr
            100                 105                 110

Ser Ser Ile Gly Ala Val Tyr Met Asp Pro Asn Lys Gly Pro Asp Val
            115                 120                 125

Val Ile Asp Glu Ser Cys Trp Ser Asp Leu Glu Phe Cys Lys Asn Thr
            130                 135                 140

Lys Asn Trp Tyr Cys Tyr Gly Lys Ala Val Ala Glu Gln Ala Ala Trp
145                 150                 155                 160

Asp Met Ala Lys Glu Lys Gly Val Asp Leu Val Val Val Asn Pro Val
            165                 170                 175

Leu Val Leu Gly Pro Leu Leu Gln Pro Thr Val Asn Ala Ser Ile Val
            180                 185                 190

His
```

<210> SEQ ID NO 2
<211> LENGTH: 338
<212> TYPE: PRT
<213> ORGANISM: Populus tremula

<400> SEQUENCE: 2

```
Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
            35                  40                  45

Pro Lys Asn Ser His Leu Arg Glu Leu Glu Gly Ala Gln Glu Arg Leu
50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
            85                  90                  95

Asp Pro Glu Glu Met Val Glu Pro Ala Val Asn Gly Thr Lys Asn Val
            100                 105                 110

Ile Ile Ala Ala Ala Glu Ala Lys Val Arg Arg Val Val Phe Thr Ser
            115                 120                 125

Ser Ile Gly Ala Val Tyr Met Asp Pro Asn Lys Gly Pro Asp Val Val
            130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
            165                 170                 175
```

```
Met Ala Lys Glu Lys Gly Val Asp Leu Val Val Asn Pro Val Leu
            180                 185                 190

Val Leu Gly Pro Leu Leu Gln Pro Thr Val Asn Ala Ser Ile Val His
        195                 200                 205

Ile Leu Lys Tyr Leu Thr Gly Ser Ala Lys Thr Tyr Ala Asn Ser Val
    210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
            260                 265                 270

Tyr Pro Ile Pro Thr Lys Cys Ser Asp Glu Lys Asn Pro Arg Lys Gln
        275                 280                 285

Pro Tyr Lys Phe Ser Asn Gln Lys Leu Arg Asp Leu Gly Phe Glu Phe
    290                 295                 300

Thr Pro Val Lys Gln Cys Leu Tyr Glu Thr Val Lys Ser Leu Gln Glu
305                 310                 315                 320

Arg Gly His Leu Pro Ile Pro Lys Gln Ala Ala Glu Glu Ser Val Lys
                325                 330                 335

Ile Gln

<210> SEQ ID NO 3
<211> LENGTH: 338
<212> TYPE: PRT
<213> ORGANISM: Populus alba

<400> SEQUENCE: 3

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
        35                  40                  45

Pro Lys Asn Ser His Leu Arg Glu Leu Glu Gly Ala Gln Glu Arg Leu
    50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Ile Ala Ala Ala Glu Ala Lys Val Arg Arg Val Val Phe Thr Ser
        115                 120                 125

Ser Ile Gly Ala Val Tyr Met Asp Pro Asn Lys Gly Pro Asp Val Val
    130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
                165                 170                 175

Met Ala Lys Glu Lys Gly Val Asp Leu Val Val Val Asn Pro Val Leu
            180                 185                 190

Val Leu Gly Pro Leu Leu Gln Pro Thr Val Asn Ala Ser Ile Val His
        195                 200                 205
```

```
Ile Leu Lys Tyr Leu Thr Gly Ser Ala Lys Thr Tyr Ala Asn Ser Val
            210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
                260                 265                 270

Tyr Pro Ile Pro Thr Lys Cys Ser Asp Glu Lys Asn Pro Arg Lys Gln
            275                 280                 285

Pro Tyr Lys Phe Ser Asn Gln Lys Leu Arg Asp Leu Gly Phe Glu Phe
290                 295                 300

Thr Pro Val Lys Gln Cys Leu Tyr Glu Thr Val Lys Ser Leu Gln Glu
305                 310                 315                 320

Arg Gly His Leu Pro Ile Pro Lys Gln Ala Ala Glu Glu Ser Leu Lys
                325                 330                 335

Ile Gln

<210> SEQ ID NO 4
<211> LENGTH: 337
<212> TYPE: PRT
<213> ORGANISM: Populus alba

<400> SEQUENCE: 4

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
        35                  40                  45

Pro Lys Asn Ser His Leu Arg Glu Leu Glu Gly Ala Gln Glu Arg Leu
50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Thr Ala Ala Glu Ala Lys Val Arg Arg Val Val Phe Thr Ser Ser
        115                 120                 125

Ile Gly Ala Val Tyr Met Asp Pro Asn Lys Gly Pro Asp Val Val Ile
130                 135                 140

Asp Glu Ser Cys Trp Ser Asp Leu Glu Phe Cys Lys Asn Thr Lys Asn
145                 150                 155                 160

Trp Tyr Cys Tyr Gly Lys Ala Val Ala Glu Gln Ala Ala Trp Asp Met
                165                 170                 175

Ala Lys Glu Lys Gly Val Asp Leu Val Val Asn Pro Val Leu Val
            180                 185                 190

Leu Gly Pro Leu Leu Gln Pro Thr Val Asn Ala Ser Ile Val His Ile
        195                 200                 205

Leu Lys Tyr Leu Thr Gly Ser Ala Lys Thr Tyr Ala Asn Ser Val Gln
210                 215                 220

Ala Tyr Val His Val Arg Asp Val Ala Leu Ala His Ile Leu Val Phe
225                 230                 235                 240
```

-continued

Glu Thr Pro Ser Ala Ser Gly Arg Tyr Leu Cys Ser Glu Ser Val Leu
              245                 250                 255

His Arg Gly Glu Val Val Glu Ile Leu Ala Lys Phe Phe Pro Glu Tyr
        260                 265                 270

Pro Ile Pro Thr Lys Cys Ser Asp Glu Lys Asn Pro Arg Lys Gln Pro
            275                 280                 285

Tyr Lys Phe Ser Asn Gln Lys Leu Arg Asp Leu Gly Phe Glu Phe Thr
        290                 295                 300

Pro Val Lys Gln Cys Leu Tyr Glu Thr Val Lys Ser Leu Gln Glu Arg
305                 310                 315                 320

Gly His Leu Pro Ile Pro Lys Gln Ala Ala Glu Glu Ser Leu Lys Ile
                325                 330                 335

Gln

<210> SEQ ID NO 5
<211> LENGTH: 337
<212> TYPE: PRT
<213> ORGANISM: Populus tremula

<400> SEQUENCE: 5

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
        35                  40                  45

Pro Lys Asn Ser His Leu Arg Glu Leu Glu Gly Ala Gln Glu Arg Leu
    50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Thr Ala Ala Glu Ala Lys Val Arg Arg Val Val Phe Thr Ser Ser
        115                 120                 125

Ile Gly Ala Val Tyr Met Asp Pro Asn Lys Gly Pro Asp Val Val Ile
    130                 135                 140

Asp Glu Ser Cys Trp Ser Asp Leu Glu Phe Cys Lys Asn Thr Lys Asn
145                 150                 155                 160

Trp Tyr Cys Tyr Gly Lys Ala Val Ala Glu Gln Ala Ala Trp Asp Met
                165                 170                 175

Ala Lys Glu Lys Gly Val Asp Leu Val Val Val Asn Pro Val Leu Val
            180                 185                 190

Leu Gly Pro Leu Leu Gln Pro Thr Val Asn Ala Ser Ile Val His Ile
        195                 200                 205

Leu Lys Tyr Leu Thr Gly Ser Ala Lys Thr Tyr Ala Asn Ser Val Gln
    210                 215                 220

Ala Tyr Val His Val Arg Asp Val Ala Leu Ala His Ile Leu Val Phe
225                 230                 235                 240

Glu Thr Pro Ser Ala Ser Gly Arg Tyr Leu Cys Ser Glu Ser Val Leu
                245                 250                 255

His Arg Gly Glu Val Val Glu Ile Leu Ala Lys Phe Phe Pro Glu Tyr
            260                 265                 270

```
Pro Ile Pro Thr Lys Cys Ser Asp Glu Lys Asn Pro Arg Lys Gln Pro
            275                 280                 285

Tyr Lys Phe Ser Asn Gln Lys Leu Arg Asp Leu Gly Phe Glu Phe Thr
        290                 295                 300

Pro Val Lys Gln Cys Leu Tyr Glu Thr Val Lys Ser Leu Gln Glu Arg
305                 310                 315                 320

Gly His Leu Pro Ile Pro Lys Gln Ala Ala Glu Ser Val Lys Ile
                325                 330                 335

Gln

<210> SEQ ID NO 6
<211> LENGTH: 2904
<212> TYPE: DNA
<213> ORGANISM: Populus alba

<400> SEQUENCE: 6
```

| | | | | | |
|---|---|---|---|---|---|
| gtaacatcca | cttttaagc | caagataaga | agaaaagaca | tctcctctcc | tctttctccc | 60 |
| tgtctgttct | ccactttccc | agtcaccaaa | ctcgtataca | tataattaca | tttgtccaaa | 120 |
| tataacaaca | tgccggttga | tgcttcatct | ctttcaggcc | aaggccaaac | tatctgtgtc | 180 |
| accgggctg | gtggtttcat | tgcttcttgg | atggttaaac | ttcttttaga | taaaggttac | 240 |
| actgttagag | gaactgcgag | gaacccaggt | tagtttatgg | tacttaagca | ctttttttt | 300 |
| aaaagattgt | gttgtttaat | taattcaatg | gtagtagtaa | tgtttatggg | ttgttttct | 360 |
| gttcttatat | ataaatatat | acagctgatc | ccaagaattc | tcatttgagg | gagcttgaag | 420 |
| gagctcaaga | aagattaact | ttatgcaaag | ctgatcttct | tgattatgag | tctcttaaag | 480 |
| aggctattca | agggtgtgat | ggtgttttcc | acactgcttc | tcccgtcaca | gatgatccgg | 540 |
| tatgcttccc | ttttcccttt | gttttccagt | cattaaaaga | tttggatctg | agaatactat | 600 |
| caagaaaata | aaataaaata | aaaaactcac | acagctaatt | ttagcacaaa | tgtcactaac | 660 |
| tcacggtagg | cttgaccgtt | ctgcaccaac | aaattcactt | tgtagttggt | gggtggaggg | 720 |
| atcagttggg | gcccaccca | cctaaaactt | tcggcagtgg | aatttctaat | tatagacggg | 780 |
| tcactcgaaa | ttaataaaaa | tattacacgg | taattaatgg | tggtggtttt | gatgagatgc | 840 |
| ttttcttgac | aataattaaa | ggaagaaatg | gtggagccag | cagtgaacgg | gaccaaaaat | 900 |
| gtgatcattg | cggcggctga | ggccaaagtc | cgacgagtgg | tgttcacgtc | ctcaattggt | 960 |
| gctgtgtaca | tggatcccaa | taagggccca | gatgttgtca | ttgatgaatc | ttgctggagt | 1020 |
| gatcttgaat | tctgcaagaa | caccaaggta | tctaattaat | taaatgccaa | gtttccttc | 1080 |
| ttgtggacca | gtcatatttc | ctagctaaca | cctgaaccaa | taaatgctgt | gcaattgaga | 1140 |
| tgtcaaagaa | ctttcatgta | tatttcttag | acatttggca | ggtatagctt | gcccgttctg | 1200 |
| tgttaagttg | ccttattata | attgaaaatt | cacttaacaa | aaaattgaac | gagtcacatc | 1260 |
| ttttctaacc | ccgttctggt | agctttccat | tgattcgatt | catacctaac | ctgagagtaa | 1320 |
| tggattgaaa | tgaaatggaa | ttgcagaatt | ggtattgcta | tggaaaggcg | gtggcagaac | 1380 |
| aagctgcgtg | ggatatggct | aaggagaaag | gggtggacct | agtggtggtt | aacccagtgc | 1440 |
| tggtgctcgg | accattgttg | cagcccactg | tcaatgctag | catcgttcac | atcctcaagt | 1500 |
| acctcaccgg | ctcagccaag | acatatgcta | actctgttca | agcttatgtg | catgttaggg | 1560 |
| atgtggcact | agcccacatt | ttagtctttg | agacgccttc | cgcctccggc | cgttaccttt | 1620 |
| gctctgagag | cgttctccac | cgtggagagg | tggtggaaat | ccttgcaaag | ttcttccccg | 1680 |
| agtaccccat | ccctaccaag | taagtaatta | ttatttgaa | gaatttcatg | gagtaattac | 1740 |

-continued

| | |
|---|---|
| tcaataaaag ggtagttggc cgagtaacag gcgacacaaa tgcattaaac gttaggacat | 1800 |
| gcacttatga ttagtcactc aaaaaaacta ccatcaaaat tgaaagaaaa cctgggaatg | 1860 |
| gcattttgaa aatggcaaaa caaataaata tgatcctgct tttgaatgac ccaaaggatg | 1920 |
| aaattgtggt gtgcggcggt tgttgtacca gctttgactt gtattaatcc gaaccaaaaa | 1980 |
| tcaatgaaca atccattctc ctatgagtcc tcaccaaccc cattgtctgg caagtcggga | 2040 |
| ccaaaatgag tttctctacc aacccaagtt atgattggac actgcacaaa attattggaa | 2100 |
| gagtattggg cccgccctgc tccttcatct catacaatta tatgctaaat tcatctctct | 2160 |
| aaatgtgatt tgctcaagat tagacaagtg gaaggaatat tcctagttgg tttgctactt | 2220 |
| gctaggtcat aagaaacagt tttgtaatgt atttgcaggt gctcagatga gaagaaccca | 2280 |
| agaaaacaac cttacaagtt ctcaaaccag aagctaaggg atctgggctt cgaattcaca | 2340 |
| ccagtgaagc agtgtctgta tgaaactgtt aagagcttgc aggaaagggg tcaccttcca | 2400 |
| atcccaaaac aagctgcaga agagtctctg aagattcaat aaggcctctt ggaactattt | 2460 |
| attaggatac atttccatat cccaagtttg gatcgcaaat gctagggaaa agagcttatt | 2520 |
| aaagaatgtc aatgtgcagg tgttttagta ttttacatga agaactctga ttatccttgt | 2580 |
| gtttatatta attttcttca agtgagtgtc ttacacttgt attcgtggct gtctaagttt | 2640 |
| atccaatttc aatatcgaag aggaacagtt ctatgtctta cacaagagca tcaactttga | 2700 |
| ccacacaact ggcatatgct ttattcaatt taattggaga ccttaaccta catgataggt | 2760 |
| acgcaaattt caatcaaggg aatccaccag atatgatgtt gacgccatgt ataatcagaa | 2820 |
| gatgattgta tgttggtgga ataatcatcc ttgtgatatt caagtaagaa acaaactca | 2880 |
| acaactattt aaataaataa aaaa | 2904 |

<210> SEQ ID NO 7
<211> LENGTH: 2894
<212> TYPE: DNA
<213> ORGANISM: Populus tremula

<400> SEQUENCE: 7

| | |
|---|---|
| gtaacatcca cttttttaagc caagataaga agaaaagaca tctcctctcc tctctctttc | 60 |
| tgtctgttct ccactttccc agtcaccaaa ctcgtaaaca tataattaca tttatccaaa | 120 |
| tataacaaca tgcctgttga tgcttcatca ctttcaggcc aaggccaaac tatctgtgtc | 180 |
| accggggctg gtggtttcat tgcttcttgg atggttaaac ttcttttaga taaaggttac | 240 |
| actgttagag gaactgcgag gaacccaggt tagttaatgg tacttaagca cttttttttaa | 300 |
| aagattgtgt tgtttaatta attcaatggt agtagtaatg ttatgggttg ttttttctgtt | 360 |
| cttatatata aatatataca gctgatccca agaattctca tttgagggag cttgaaggag | 420 |
| ctcaagaaag attaacttta tgcaaagctg atcttcttga ttatgagtct cttaaagagg | 480 |
| ctattcaagg gtgtgatggt gttttccaca ctgcttctcc tgtcacagat gatccggtat | 540 |
| gcttcctttt tcccttttgct ttccagtcat taaaagattt ggatctgaga atatcaagaa | 600 |
| aaaaaataat caaataaaac tcacacagct tattttagca cacatgtcac taactcacgg | 660 |
| taggcttgac cgttctgcac caacaaattc actttgtagt tggtgggtgg agggatcaat | 720 |
| tggggcccac cccacctaaa actttcggca gtgaaatttc taattataga cgggtcactc | 780 |
| gaaattaata aaatattaca tggtaattaa tggtggtggt tttgatgaga tgcttttgtt | 840 |
| gacaataatt aaaggaagaa atggtggagc cagcagtgaa cgggaccaaa aatgtgatca | 900 |

```
ttgcggcggc tgaggccaaa gtccgacgag tggtgttcac gtcctcaatt ggtgctgtgt    960
acatggatcc caataagggc ccagatgttg tcattgatga atcttgctgg agtgatcttg   1020
aattctgcaa gaacaccaag gtatctaatt aattaaatgc caagttttcc ttcttgtcga   1080
ctagtcatat tttccaagct aacacctgaa ccaataaatg ctgtgcaatt gagatgtcaa   1140
agaattttca tacatatttc ttagacattt ggtaggtata gctaacccgt tctttgtcaa   1200
gttgccttat tataattgaa aattcacttt aaaaaaaaat caacgagttg catcttatct   1260
aaccccgttc tggtagctgt ccattgattc gattcatacc taacctgaga gtaatggatt   1320
gaaatgaaat ggaattgcag aattggtatt gctatggaaa ggctgtggca gaacaagctg   1380
catgggatat ggctaaggag aaagggqtgg acctagtggt ggttaaccca gtgctggtgc   1440
tcggaccatt gttgcagccc actgtcaatg ctagcatcgt tcacatcctc aagtacctca   1500
ccggctcagc caagacatat gctaactctg ttcaagctta tgtgcatgtt agggatgtgg   1560
cactagccca cattttagtc tttgagacgc cttccgcctc cggccgttac ctctgctctg   1620
agagcgttct ccaccgtgga gaggtggtgg aaatccttgc aaagttcttc cccgagtacc   1680
ccatccctac caagtaagta actattattt tgaagaattt catggagtaa ttactcaata   1740
aaagggtagt tgaccgagta acaggcgaca caaatgcatt aaacgttagg acatgcactt   1800
atgattagtc actcaaaaaa actacaatca aaattgaaag aaaacctggg aatggcattt   1860
tgaaaatggc gaaacaaata aatatgatcc cgcttttgaa tgacccaaag gatgaaattg   1920
tggtgtgcgg cggttgttgt accagctttg acttgtatta atctgaacca aaaatcatga   1980
acaatccatt ctcctatgag tcctcaccaa ccccattgtc tgccaagtcg ggaccaaaat   2040
gagtttctct accaacccaa gttatgattg gacactgcac aaaattattg gaagagtatt   2100
gggcccgccc tgctccttca tctcatacaa ttatatgcta aattcatctc tctaaatgtg   2160
atttgctcaa gattagacaa gtggaaggaa tattcctagt tgggttgcta cttgctaggt   2220
cataagaaac agttctgtaa tgtatttgca ggtgctcaga tgagaagaac ccaagaaaac   2280
aaccttacaa gttctcaaac cagaagctaa gggatctggg cttcgaattc acaccagtga   2340
agcagtgtct gtatgaaact gttaagagct tgcaggaaag gggtcacctt ccaatcccaa   2400
aacaagctgc agaagagtct gtgaagattc aataaggcct cttggaacta tttattagga   2460
tacagttcca tacccaagt ttggatcgca atgctaggg aaaagagctt attaaagaat   2520
gtcaatgtgc aggtgtttta gtattttaca tgaagaactc tgattatcct tgtgcttata   2580
ttaattttct tcaagtgagt gtcttacact tgtatttgtg gttgtctaag tttatccaat   2640
ttcaatatca aagaggaaca gttctatgtc ttacacaaga gcatcaacat tgaccacaca   2700
actggcatat gctttattca atttaattgg agaccttaac ctacatgata ggtacgcaaa   2760
tttcaatcaa gggaatccac cagatatgat gttgacgcca tgtataatca gaagatgatt   2820
gtatattggt ggaataatca tccttgtgat attcaagtaa gaaacaaac tcaacaacta   2880
tttaaataaa taaa                                                    2894
```

<210> SEQ ID NO 8
<211> LENGTH: 341
<212> TYPE: PRT
<213> ORGANISM: Isatis tinctoria

<400> SEQUENCE: 8

```
Met Pro Val Asp Glu Ser Ser Gln Ala Gly Lys Ile Val Cys Val Thr
1               5                   10                  15
```

Gly Ala Gly Gly Tyr Ile Ala Ser Trp Ile Val Lys Ser Leu Leu Glu
            20                  25                  30

Arg Gly Tyr Thr Val Lys Gly Thr Val Arg Asn Pro Asp Asp Pro Lys
        35                  40                  45

Asn Thr His Leu Arg Glu Leu Gln Gly Ala Lys Glu Arg Leu Ile Leu
    50                  55                  60

Cys Lys Ala Asp Leu Gln Asp Tyr Glu Ala Leu Lys Ala Ala Ile Asp
65                  70                  75                  80

Gly Cys Asp Gly Val Phe His Thr Ala Ser Pro Val Thr Asp Asp Pro
                85                  90                  95

Glu Gln Met Val Glu Pro Ala Val Asn Gly Ala Lys Phe Val Ile Asn
            100                 105                 110

Ala Ala Ala Glu Thr Lys Val Lys Arg Val Val Ile Thr Ser Ser Ile
        115                 120                 125

Gly Ala Ile Tyr Met Asp Pro Asn Arg Asp Pro Glu Val Val Val Asp
    130                 135                 140

Glu Ser Cys Trp Ser Asp Leu Glu Phe Cys Lys Asp Thr Lys Asn Trp
145                 150                 155                 160

Tyr Cys Tyr Gly Lys Met Val Ala Glu Gln Ala Ala Trp Glu Thr Ala
                165                 170                 175

Lys Glu Lys Gly Val Asp Leu Val Val Leu Asn Pro Val Leu Val Leu
            180                 185                 190

Gly Pro Pro Leu Gln Pro Thr Ile Asn Ala Ser Leu Phe His Val Leu
        195                 200                 205

Lys Tyr Leu Thr Gly Ser Ala Lys Thr Tyr Ala Asn Leu Thr Gln Val
    210                 215                 220

Tyr Val Asp Val Arg Asp Val Ala Leu Ala His Val Leu Val Tyr Glu
225                 230                 235                 240

Glu Pro Ser Ala Ser Gly Arg Tyr Leu Leu Ala Glu Ser Ala Leu His
                245                 250                 255

Arg Gly Glu Val Val Glu Ile Leu Ala Lys Leu Phe Pro Glu Tyr Pro
            260                 265                 270

Leu Pro Thr Lys Cys Lys Asp Glu Lys Asn Pro Arg Ala Lys Pro Tyr
        275                 280                 285

Lys Phe Thr Asn Gln Lys Ile Lys Asp Leu Gly Leu Glu Phe Thr Ser
    290                 295                 300

Ile Lys Gln Ser Leu Tyr Asp Thr Val Lys Ser Leu Gln Glu Lys Gly
305                 310                 315                 320

His Leu Pro Pro Pro Ser Thr Ser Gln Asp Ser Ser Gln Asn Gly
                325                 330                 335

Ile Lys Ile Glu Ser
            340

<210> SEQ ID NO 9
<211> LENGTH: 344
<212> TYPE: PRT
<213> ORGANISM: Arabidopsis thaliana

<400> SEQUENCE: 9

Met Pro Val Asp Val Ala Ser Pro Ala Gly Lys Thr Val Cys Val Thr
1               5                   10                  15

Gly Ala Gly Gly Tyr Ile Ala Ser Trp Ile Val Lys Ile Leu Leu Glu
            20                  25                  30

Arg Gly Tyr Thr Val Lys Gly Thr Val Arg Asn Pro Asp Asp Pro Lys
        35                  40                  45

-continued

```
Asn Thr His Leu Arg Glu Leu Glu Gly Gly Lys Glu Arg Leu Ile Leu
 50                  55                  60

Cys Lys Ala Asp Leu Gln Asp Tyr Glu Ala Leu Lys Ala Ala Ile Asp
 65                  70                  75                  80

Gly Cys Asp Gly Val Phe His Thr Ala Ser Pro Val Thr Asp Asp Pro
                 85                  90                  95

Glu Gln Met Val Glu Pro Ala Val Asn Gly Ala Lys Phe Val Ile Asn
            100                 105                 110

Ala Ala Ala Glu Ala Lys Val Lys Arg Val Val Ile Thr Ser Ser Ile
        115                 120                 125

Gly Ala Val Tyr Met Asp Pro Asn Arg Asp Pro Glu Ala Val Val Asp
    130                 135                 140

Glu Ser Cys Trp Ser Asp Leu Asp Phe Cys Lys Asn Thr Lys Asn Trp
145                 150                 155                 160

Tyr Cys Tyr Gly Lys Met Val Ala Glu Gln Ala Ala Trp Glu Thr Ala
                165                 170                 175

Lys Glu Lys Gly Val Asp Leu Val Val Leu Asn Pro Val Leu Val Leu
            180                 185                 190

Gly Pro Pro Leu Gln Pro Thr Ile Asn Ala Ser Leu Tyr His Val Leu
        195                 200                 205

Lys Tyr Leu Thr Gly Ser Ala Lys Thr Tyr Ala Asn Leu Thr Gln Ala
    210                 215                 220

Tyr Val Asp Val Arg Asp Val Ala Leu Ala His Val Leu Val Tyr Glu
225                 230                 235                 240

Ala Pro Ser Ala Ser Gly Arg Tyr Leu Leu Ala Glu Ser Ala Arg His
                245                 250                 255

Arg Gly Glu Val Val Glu Ile Leu Ala Lys Leu Phe Pro Glu Tyr Pro
            260                 265                 270

Leu Pro Thr Lys Cys Lys Asp Glu Lys Asn Pro Arg Ala Lys Pro Tyr
        275                 280                 285

Lys Phe Thr Asn Gln Lys Ile Lys Asp Leu Gly Leu Glu Phe Thr Ser
    290                 295                 300

Thr Lys Gln Ser Leu Tyr Asp Thr Val Lys Ser Leu Gln Glu Lys Gly
305                 310                 315                 320

His Leu Ala Pro Pro Pro Pro Pro Ser Ala Ser Gln Glu Ser Val
                325                 330                 335

Glu Asn Gly Ile Lys Ile Gly Ser
            340

<210> SEQ ID NO 10
<211> LENGTH: 332
<212> TYPE: PRT
<213> ORGANISM: Brassica napus

<400> SEQUENCE: 10

Met Pro Ala Asp Gly Lys Leu Val Cys Val Thr Gly Ala Gly Gly Tyr
 1                   5                  10                  15

Ile Ala Ser Trp Ile Val Lys Leu Leu Leu Glu Arg Gly Tyr Thr Val
                 20                  25                  30

Arg Gly Thr Val Arg Asn Pro Ala Asp Pro Lys Asn Asn His Leu Arg
             35                  40                  45

Glu Leu Asp Gly Ala Lys Glu Arg Leu Thr Leu His Ser Ala Asp Leu
         50                  55                  60

Leu Asp Tyr Glu Ala Leu Cys Ala Ala Ile Asp Gly Cys His Gly Val
```

```
                65                  70                  75                  80
        Phe His Thr Ala Ser Pro Met Thr Asp Asp Pro Glu Thr Met Leu Glu
                            85                  90                  95

Pro Ala Val Asn Gly Ala Lys Phe Val Ile Asp Ala Ala Lys Ala
                            100                 105                 110

Lys Val Lys Arg Val Val Phe Thr Ser Ser Ile Gly Ala Val Tyr Met
                            115                 120                 125

Asn Pro Asn Arg Asp Pro Gln Thr Ile Val Asn Glu Asp Cys Trp Ser
                130                 135                 140

Asp Leu Asp Phe Cys Lys Asn Thr Lys Asn Trp Tyr Cys Tyr Gly Lys
        145                 150                 155                 160

Met Val Ala Glu Gln Ser Ala Trp Glu Thr Ala Lys Ala Lys Gly Val
                            165                 170                 175

Asp Leu Val Val Leu Asn Pro Val Leu Val Leu Gly Pro Pro Leu Gln
                            180                 185                 190

Ser Ala Val Asn Ala Ser Leu Val His Ile Leu Lys Tyr Leu Thr Gly
                            195                 200                 205

Ser Ala Lys Thr Tyr Ala Asn Leu Thr Gln Val Tyr Val Asp Val Arg
                210                 215                 220

Asp Val Ala Leu Gly His Val Met Val Tyr Glu Ser Pro Ser Ala Ser
        225                 230                 235                 240

Gly Arg Tyr Ile Leu Ala Glu Thr Ala Leu His Arg Gly Glu Val Val
                            245                 250                 255

Glu Ile Leu Ala Lys Phe Phe Pro Glu Tyr Pro Leu Pro Thr Lys Cys
                            260                 265                 270

Ser Asp Asp Lys Asn Pro Arg Ala Lys Pro Tyr Lys Phe Thr Thr Gln
                275                 280                 285

Lys Ile Lys Asp Leu Gly Leu Glu Phe Thr Pro Ile Lys Gln Ser Leu
                290                 295                 300

Tyr Asp Ser Val Lys Ser Leu Gln Glu Lys Gly His Leu Pro Leu Pro
        305                 310                 315                 320

Gln Tyr Ser Asn Gln Asp Asn Val Thr Ile Glu Ser
                            325                 330

<210> SEQ ID NO 11
<211> LENGTH: 324
<212> TYPE: PRT
<213> ORGANISM: Pinus taeda

<400> SEQUENCE: 11

Met Thr Ala Gly Lys Gln Thr Glu Glu Gly Gln Thr Val Cys Val Thr
        1                   5                   10                  15

Gly Ala Gly Gly Phe Ile Ala Ser Trp Leu Val Lys Leu Leu Leu Glu
                            20                  25                  30

Arg Gly Tyr Thr Val Arg Gly Thr Val Arg Asn Pro Glu Asp Gln Lys
                    35                  40                  45

Asn Ala His Leu Lys Gln Leu Glu Gly Ala Glu Glu Arg Leu Thr Leu
                50                  55                  60

Val Lys Ala Asp Leu Met Asp Tyr Asn Ser Leu Leu Asn Ala Ile Asn
        65                  70                  75                  80

Gly Cys Gln Gly Val Phe His Val Ala Ser Pro Val Thr Asp Asp Pro
                            85                  90                  95

Glu Glu Met Val Glu Pro Ala Val Asn Gly Thr Lys Asn Val Leu Asp
                            100                 105                 110
```

```
Ala Cys Ala Val Ala Gly Val Arg Arg Val Val Phe Thr Ser Ser Ile
        115                 120                 125

Gly Ala Val Tyr Met Asp Pro Ser Arg Asp Tyr Asp Ala Leu Val Asp
        130                 135                 140

Glu Asn Cys Trp Ser Asn Leu Asp Tyr Cys Lys Glu Thr Lys Asn Trp
145                 150                 155                 160

Tyr Cys Tyr Gly Lys Thr Val Ala Glu Lys Ala Ala Trp Glu Arg Ala
                165                 170                 175

Lys Asp Lys Gly Leu Asp Leu Val Val Asn Pro Cys Val Val Leu
                180                 185                 190

Gly Pro Val Leu Gln Ser Ser Ile Asn Ser Ser Ile Ile His Ile Leu
        195                 200                 205

Lys Tyr Leu Thr Gly Ser Ala Lys Thr Tyr Ala Asn Ser Val Gln Ala
        210                 215                 220

Tyr Val His Val Arg Asp Val Ala Glu Ala His Ile Leu Val Tyr Glu
225                 230                 235                 240

Ser Pro Ser Ala Ser Gly Arg Tyr Leu Cys Ala Glu Ser Val Leu His
                245                 250                 255

Arg Gly Asp Val Val Asp Ser Leu Ala Ser Met Phe Pro Gln Tyr Pro
                260                 265                 270

Ile Pro Thr Lys Val Lys Glu Asp Gly Lys Pro Arg Val Lys Pro Trp
        275                 280                 285

Lys Val Ser Asn Gln Lys Leu Lys Asp Leu Gly Leu Glu Phe Thr Pro
        290                 295                 300

Ala Lys Gln Cys Leu Tyr Glu Thr Val Ile Ser Leu Gln Glu Lys Gly
305                 310                 315                 320

His Ile Ser Lys

<210> SEQ ID NO 12
<211> LENGTH: 324
<212> TYPE: PRT
<213> ORGANISM: Pinus massoniana

<400> SEQUENCE: 12

Met Thr Ala Gly Lys Gln Thr Glu Glu Gly Thr Gly Cys Val Thr
1               5                   10                  15

Gly Ala Gly Gly Phe Ile Ala Ser Trp Leu Val Lys Leu Leu Leu Glu
        20                  25                  30

Arg Gly Tyr Thr Val Arg Gly Thr Val Arg Asn Pro Glu Asp Gln Lys
        35                  40                  45

Asn Ala His Leu Lys Gln Leu Glu Gly Ala Glu Glu Arg Leu Thr Leu
    50                  55                  60

Val Lys Ala Asp Leu Met Asp Tyr Asn Ser Leu Leu Asn Ala Ile Asn
65                  70                  75                  80

Gly Cys Gln Gly Val Phe His Val Ala Ser Pro Val Thr Asp Asp Pro
                85                  90                  95

Glu Glu Met Val Glu Pro Ala Val Asn Gly Thr Lys Asn Val Leu Asp
            100                 105                 110

Ala Cys Ala Val Ala Gly Val Arg Arg Val Val Phe Thr Ser Ser Ile
        115                 120                 125

Gly Ala Val Tyr Met Asp Pro Ser Arg Asp Tyr Asp Ala Leu Val Asp
        130                 135                 140

Glu Asn Cys Trp Ser Asn Leu Asp Tyr Cys Lys Glu Thr Lys Asn Trp
145                 150                 155                 160
```

Tyr Cys Tyr Gly Lys Thr Val Ala Glu Lys Ala Ala Trp Glu Arg Ala
            165                 170                 175

Lys Asp Lys Gly Leu Asp Leu Val Val Val Asn Pro Cys Val Val Leu
            180                 185                 190

Gly Pro Val Leu Gln Ser Ser Ile Asn Ala Ser Ile Ile His Ile Leu
            195                 200                 205

Lys Tyr Leu Thr Gly Ser Ala Lys Thr Tyr Ala Asn Ser Val Gln Ala
            210                 215                 220

Tyr Val His Val Arg Asp Val Ala Glu Ala His Ile Leu Val Tyr Glu
225                 230                 235                 240

Ser Pro Ser Ala Ser Gly Arg Tyr Leu Cys Ala Glu Ser Val Leu His
            245                 250                 255

Arg Gly Asp Val Val Asp Leu Leu Ala Ser Met Phe Pro Gln Tyr Pro
            260                 265                 270

Ile Pro Thr Lys Val Lys Glu Asp Gly Lys Pro Arg Val Lys Pro Trp
            275                 280                 285

Lys Val Ser Asn Gln Lys Leu Lys Asp Leu Gly Leu Glu Phe Thr Pro
            290                 295                 300

Ala Lys Gln Cys Leu Tyr Glu Thr Val Ile Ser Leu Gln Glu Lys Gly
305                 310                 315                 320

His Ile Ser Lys

<210> SEQ ID NO 13
<211> LENGTH: 322
<212> TYPE: PRT
<213> ORGANISM: Picea abies

<400> SEQUENCE: 13

Met Thr Ala Gly Lys Gln Thr Gly Ala Gly Gln Thr Val Cys Val Thr
1               5                   10                  15

Gly Ala Gly Gly Phe Ile Ala Ser Trp Leu Val Lys Leu Leu Leu Glu
            20                  25                  30

Arg Gly Tyr Thr Val Arg Gly Thr Val Arg Asn Pro Glu Asp Gln Lys
            35                  40                  45

Asn Ala His Leu Arg Gln Leu Glu Gly Ala Glu Glu Arg Leu Thr Leu
            50                  55                  60

Val Lys Ala Asp Leu Met Asp Tyr Asn Ser Leu Leu Asn Ala Ile Thr
65                  70                  75                  80

Gly Cys Gln Gly Val Phe His Val Ala Ser Pro Val Thr Asp Asp Pro
            85                  90                  95

Val Gln Met Val Glu Pro Ala Val Asn Gly Thr Lys Asn Val Leu Asp
            100                 105                 110

Ala Cys Ala Glu Ala Ala Val Arg Arg Val Val Phe Thr Ser Ser Ile
            115                 120                 125

Gly Ala Val Tyr Met Asp Pro Thr Arg Asp Tyr Asp Ala Leu Val Asp
            130                 135                 140

Glu Ser Cys Trp Ser Asn Leu Asp Phe Cys Lys Asp Thr Lys Asn Trp
145                 150                 155                 160

Tyr Cys Tyr Gly Lys Ala Val Ala Glu Lys Ala Ala Trp Asp Arg Ala
            165                 170                 175

Lys Glu Lys Gly Leu Asp Leu Val Val Val Asn Pro Cys Val Val Leu
            180                 185                 190

Gly Pro Val Leu Gln Ser Ser Ile Asn Ala Ser Ile Leu His Ile Leu
            195                 200                 205

```
Lys Tyr Leu Thr Gly Ser Ala Lys Thr Tyr Ala Asn Ser Val Gln Ala
    210                 215                 220

Tyr Val His Val Arg Asp Val Ala Glu Ala His Ile Leu Val Tyr Glu
225                 230                 235                 240

Ser Pro Ser Ala Ser Gly Arg Tyr Leu Cys Ala Glu Ser Val Leu His
                245                 250                 255

Arg Gly Asp Val Val Glu Leu Leu Glu Lys Met Phe Pro Gln Tyr Pro
                260                 265                 270

Ile Pro Thr Lys Cys Lys Asp Gly Lys Pro Arg Val Lys Pro Trp
                275                 280                 285

Lys Val Ser Asn Gln Lys Leu Lys Asp Leu Gly Leu Glu Phe Thr Pro
290                 295                 300

Ala Lys Gln Cys Leu Tyr Glu Thr Val Ile Ser Leu Gln Glu Lys Gly
305                 310                 315                 320

His Ile

<210> SEQ ID NO 14
<211> LENGTH: 336
<212> TYPE: PRT
<213> ORGANISM: Leucaena leucocephala

<400> SEQUENCE: 14

Met Pro Ala Ala Pro Ala Pro Thr Ala Asn Thr Thr Ser Ser
1               5                   10                  15

Gly Ser Gly Gln Thr Val Cys Val Thr Gly Ala Gly Gly Phe Ile Ala
                20                  25                  30

Ser Trp Ile Val Lys Leu Leu Leu Glu Arg Gly Tyr Thr Val Arg Gly
            35                  40                  45

Thr Val Arg Asn Pro Asp Asp Ser Lys Asn Ser His Leu Lys Glu Leu
        50                  55                  60

Glu Gly Ala Glu Glu Arg Leu Thr Leu His Lys Val Asp Leu Leu Asp
65                  70                  75                  80

Leu Glu Ser Val Lys Ala Val Ile Asn Gly Cys Asp Gly Ile Ile His
                85                  90                  95

Thr Ala Ser Pro Val Thr Asp Asn Pro Glu Glu Met Val Glu Pro Ala
                100                 105                 110

Val Asn Gly Ala Lys Asn Val Ile Ala Ala Glu Ala Lys Val
                115                 120                 125

Arg Arg Val Val Phe Thr Ser Ser Ile Gly Ala Val Tyr Met Asp Pro
130                 135                 140

Ser Arg Asn Ile Asp Glu Val Val Asp Glu Ser Cys Trp Ser Asn Leu
145                 150                 155                 160

Glu Tyr Cys Lys Asn Thr Lys Asn Trp Tyr Cys Tyr Gly Lys Ala Val
                165                 170                 175

Ala Glu Gln Ala Ala Trp Asp Glu Ala Lys Ala Arg Gly Val Asp Leu
                180                 185                 190

Val Val Val Asn Pro Val Leu Val Leu Gly Pro Leu Leu Gln Ser Thr
                195                 200                 205

Met Asn Ala Ser Thr Ile His Ile Leu Lys Tyr Leu Thr Gly Ser Ala
210                 215                 220

Lys Thr Tyr Ala Asn Ala Thr Gln Ala Tyr Val His Val Lys Asp Val
225                 230                 235                 240

Ala Leu Ala His Val Leu Val Tyr Glu Ile Pro Ser Ala Ser Gly Arg
                245                 250                 255
```

```
Tyr Leu Cys Ser Glu Ser Ser Leu His Arg Gly Glu Leu Val Glu Ile
            260                 265                 270

Leu Ala Lys Tyr Phe Pro Glu Tyr Pro Ile Pro Thr Lys Cys Ser Asp
            275                 280                 285

Glu Lys Asn Pro Arg Ala Lys Ala Tyr Thr Phe Ser Asn Lys Arg Leu
290                 295                 300

Lys Asp Leu Gly Leu Glu Phe Thr Pro Val His Gln Cys Leu Tyr Asp
305                 310                 315                 320

Thr Val Lys Ser Leu Gln Asp Lys Gly His Leu Pro Leu Pro Thr Lys
            325                 330                 335

<210> SEQ ID NO 15
<211> LENGTH: 334
<212> TYPE: PRT
<213> ORGANISM: Leucaena leucocephala

<400> SEQUENCE: 15

Met Pro Ala Ala Pro Ala Ala Ala Asn Thr Thr Ser Ser Gly Ser
1               5                   10                  15

Gly Gln Thr Val Cys Val Thr Gly Ala Gly Gly Phe Ile Ala Ser Trp
            20                  25                  30

Ile Val Lys Leu Leu Leu Glu Arg Asp Tyr Thr Val Arg Gly Thr Ala
            35                  40                  45

Arg Asn Pro Asp Asp Ser Lys Asn Ala His Leu Lys Glu Leu Glu Gly
50                  55                  60

Ala Glu Glu Arg Leu Thr Leu His Lys Val Asp Leu Leu Asp Leu Glu
65                  70                  75                  80

Ser Val Lys Ala Ala Ile Asn Gly Cys Asp Gly Val Ile His Thr Ala
            85                  90                  95

Ser Pro Val Thr Asp Asn Pro Glu Glu Met Val Glu Pro Ala Val Asn
            100                 105                 110

Gly Ala Lys Asn Val Ile Ile Ala Ala Glu Ala Lys Val Arg Arg
            115                 120                 125

Val Val Phe Thr Ser Ser Ile Gly Ala Val Tyr Met Asp Pro Ser Arg
            130                 135                 140

Asn Ile Asp Glu Val Val Asp Glu Ser Cys Trp Ser Asn Leu Glu Tyr
145                 150                 155                 160

Cys Lys Thr Thr Lys Asn Trp Tyr Cys Tyr Gly Lys Ala Val Ala Glu
            165                 170                 175

Gln Ala Ala Trp Asp Glu Ala Lys Ala Arg Gly Val Asp Leu Val Val
            180                 185                 190

Val Asn Pro Val Leu Val Leu Gly Pro Leu Leu Gln Thr Thr Met Asn
            195                 200                 205

Ala Ser Thr Ile His Ile Leu Lys Tyr Leu Thr Gly Ser Ala Lys Thr
            210                 215                 220

Tyr Ala Asn Ala Thr Gln Ala Tyr Val His Val Lys Asp Val Ala Leu
225                 230                 235                 240

Ala His Val Leu Val Tyr Glu Thr Pro Ser Ala Ser Gly Arg Tyr Leu
            245                 250                 255

Cys Ser Glu Ser Ser Leu His Arg Gly Glu Leu Val Glu Ile Leu Ala
            260                 265                 270

Lys Tyr Phe Pro Glu Tyr Pro Ile Pro Thr Lys Cys Ser Asp Glu Lys
            275                 280                 285

Asn Pro Arg Ala Lys Pro Tyr Thr Phe Ser Asn Lys Arg Leu Lys Asp
290                 295                 300
```

```
Leu Gly Leu Glu Phe Thr Pro Val His Gln Cys Leu Tyr Asp Thr Val
305                 310                 315                 320

Lys Ser Leu Gln Asp Lys Gly His Leu Pro Leu Pro Thr Lys
                325                 330
```

<210> SEQ ID NO 16
<211> LENGTH: 336
<212> TYPE: PRT
<213> ORGANISM: Eucalyptus saligna

<400> SEQUENCE: 16

```
Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Leu Leu Glu
            20                  25                  30

Arg Gly Tyr Thr Val Arg Gly Thr Val Arg Asn Pro Asp Asp Pro Lys
        35                  40                  45

Asn Gly His Leu Arg Asp Leu Glu Gly Ala Ser Glu Arg Leu Thr Leu
    50                  55                  60

Tyr Lys Gly Asp Leu Met Asp Tyr Gly Ser Leu Glu Glu Ala Ile Lys
65                  70                  75                  80

Gly Cys Asp Gly Val Val His Thr Ala Ser Pro Val Thr Asp Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Gly Pro Asp Val Val Val Asp
    130                 135                 140

Glu Ser Cys Trp Ser Asp Leu Glu Phe Cys Lys Ser Thr Lys Asn Trp
145                 150                 155                 160

Tyr Cys Tyr Gly Lys Ala Val Ala Glu Lys Ala Arg Cys Ala Glu Ala
                165                 170                 175

Lys Glu Arg Gly Val Asp Leu Val Val Ile Asn Pro Val Leu Val Leu
            180                 185                 190

Gly Pro Leu Leu Gln Ser Thr Ile Asn Ala Ser Ile Ile His Ile Leu
        195                 200                 205

Lys Tyr Leu Thr Gly Ser Ala Lys Thr Tyr Ala Asn Ser Val Gln Ala
    210                 215                 220

Tyr Val His Val Lys Asp Val Ala Leu Ala His Val Leu Val Leu Glu
225                 230                 235                 240

Thr Pro Ser Ala Ser Gly Arg Tyr Leu Cys Asp Glu Ser Val Leu His
                245                 250                 255

Arg Gly Asp Val Val Glu Ile Leu Ala Lys Phe Phe Pro Glu Tyr Asn
            260                 265                 270

Val Pro Thr Lys Cys Ser Asp Glu Val Asn Pro Arg Val Lys Pro Tyr
        275                 280                 285

Lys Phe Ser Asn Gln Lys Leu Lys Asp Leu Gly Leu Glu Phe Thr Pro
    290                 295                 300

Val Lys Gln Cys Leu Tyr Glu Thr Val Lys Ser Leu Gln Glu Lys Gly
305                 310                 315                 320

His Leu Pro Val Pro Pro Pro Glu Asp Ser Val Arg Ile Gln Gly
                325                 330                 335
```

```
<210> SEQ ID NO 17
<211> LENGTH: 336
<212> TYPE: PRT
<213> ORGANISM: Eucalyptus urophylla

<400> SEQUENCE: 17
```

Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Leu Leu Glu
            20                  25                  30

Arg Gly Tyr Thr Val Arg Gly Thr Val Arg Asn Pro Asp Asp Pro Lys
        35                  40                  45

Asn Gly His Leu Arg Glu Leu Glu Gly Ala Ser Glu Arg Leu Thr Leu
    50                  55                  60

Tyr Lys Gly Asp Leu Met Asp Tyr Gly Ser Leu Glu Glu Ala Ile Lys
65                  70                  75                  80

Gly Cys Asp Gly Val Val His Thr Ala Ser Pro Val Thr Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Gly Pro Asp Val Val Asp
    130                 135                 140

Glu Ser Cys Trp Ser Asp Leu Glu Phe Cys Lys Ser Thr Lys Asn Trp
145                 150                 155                 160

Tyr Cys Tyr Gly Lys Ala Val Ala Glu Lys Ala Ala Cys Ala Glu Ala
                165                 170                 175

Lys Glu Arg Gly Val Asp Leu Val Val Ile Asn Pro Val Leu Val Leu
            180                 185                 190

Gly Pro Leu Leu Gln Ser Thr Ile Asn Ala Ser Ile Ile His Ile Leu
        195                 200                 205

Lys Tyr Leu Thr Gly Ser Ala Lys Thr Tyr Ala Asn Ser Val Gln Ala
    210                 215                 220

Tyr Val His Val Lys Asp Val Ala Leu Ala His Val Leu Val Leu Glu
225                 230                 235                 240

Asn Pro Ser Ala Ser Gly Arg Tyr Leu Cys Ala Glu Ser Val Leu His
                245                 250                 255

Arg Gly Asp Val Val Glu Ile Leu Ala Lys Phe Phe Pro Glu Tyr Asn
            260                 265                 270

Val Pro Thr Lys Cys Ser Asp Glu Val Asn Pro Arg Val Lys Pro Tyr
        275                 280                 285

Lys Phe Ser Asn Gln Lys Leu Lys Asp Leu Gly Leu Glu Phe Thr Pro
    290                 295                 300

Val Lys Gln Cys Leu Tyr Glu Thr Val Lys Ser Leu Gln Glu Lys Gly
305                 310                 315                 320

His Leu Pro Val Pro Pro Pro Glu Asp Ser Val Arg Ile Gln Gly
                325                 330                 335

```
<210> SEQ ID NO 18
<211> LENGTH: 336
<212> TYPE: PRT
<213> ORGANISM: Eucalyptus cordata
<220> FEATURE:
<221> NAME/KEY: misc_feature
<222> LOCATION: (4)..(4)
<223> OTHER INFORMATION: Xaa can be any naturally occurring amino acid
```

```
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 18
```

| Met | Pro | Val | Xaa | Ala | Leu | Xaa | Gly | Ser | Xaa | Gln | Thr | Val | Cys | Val | Thr |
|---|---|---|---|---|---|---|---|---|---|---|---|---|---|---|---|
| 1 | | | | 5 | | | | | 10 | | | | | 15 | |

| Gly | Ala | Gly | Gly | Phe | Ile | Ala | Ser | Trp | Ile | Val | Lys | Leu | Leu | Leu | Xaa |
|---|---|---|---|---|---|---|---|---|---|---|---|---|---|---|---|
| | | | 20 | | | | | 25 | | | | | 30 | | |

| Arg | Gly | Tyr | Thr | Val | Arg | Gly | Thr | Val | Arg | Asn | Pro | Asp | Asp | Pro | Lys |
| | | | 35 | | | | | 40 | | | | | 45 | | |

| Asn | Gly | His | Leu | Arg | Asp | Leu | Glu | Gly | Ala | Ser | Glu | Arg | Leu | Thr | Leu |
| | 50 | | | | | 55 | | | | | 60 | | | | |

| Tyr | Lys | Gly | Asp | Leu | Met | Asp | Tyr | Gly | Ser | Leu | Glu | Glu | Ala | Ile | Lys |
| 65 | | | | | 70 | | | | | 75 | | | | | 80 |

| Gly | Cys | Asp | Gly | Val | Val | His | Thr | Ala | Ser | Pro | Val | Thr | Asp | Asp | Pro |
| | | | | 85 | | | | | 90 | | | | | 95 | |

| Glu | Gln | Met | Val | Glu | Pro | Ala | Val | Ile | Gly | Thr | Lys | Asn | Val | Ile | Val |
| | | | 100 | | | | | 105 | | | | | 110 | | |

| Ala | Ala | Ala | Glu | Ala | Lys | Val | Arg | Arg | Val | Val | Phe | Thr | Ser | Ser | Ile |
| | | | 115 | | | | | 120 | | | | | 125 | | |

| Gly | Ala | Val | Thr | Met | Asp | Pro | Asn | Arg | Gly | Pro | Asp | Val | Val | Val | Asp |
| | 130 | | | | | 135 | | | | | 140 | | | | |

| Glu | Ser | Cys | Trp | Ser | Asp | Leu | Glu | Phe | Cys | Lys | Ser | Thr | Lys | Asn | Trp |
| 145 | | | | | 150 | | | | | 155 | | | | | 160 |

| Tyr | Cys | Tyr | Gly | Lys | Ala | Val | Ala | Glu | Lys | Ala | Ala | Cys | Ala | Glu | Ala |
| | | | | 165 | | | | | 170 | | | | | 175 | |

| Lys | Glu | Arg | Gly | Val | Asp | Leu | Val | Val | Ile | Asn | Pro | Val | Leu | Val | Leu |
| | | | 180 | | | | | 185 | | | | | 190 | | |

| Gly | Pro | Leu | Leu | Gln | Ser | Thr | Ile | Asn | Ala | Ser | Ile | Ile | His | Ile | Leu |
| | | | 195 | | | | | 200 | | | | | 205 | | |

| Lys | Tyr | Leu | Thr | Gly | Ser | Ala | Lys | Thr | Tyr | Ala | Asn | Ser | Val | Gln | Ala |
| | 210 | | | | | 215 | | | | | 220 | | | | |

| Tyr | Val | His | Val | Lys | Asp | Val | Ala | Leu | Ala | His | Val | Leu | Val | Leu | Glu |
| 225 | | | | | 230 | | | | | 235 | | | | | 240 |

| Thr | Pro | Ser | Ala | Ser | Gly | Arg | Tyr | Leu | Cys | Ala | Glu | Ser | Val | Leu | His |
| | | | | 245 | | | | | 250 | | | | | 255 | |

| Arg | Gly | Asp | Val | Val | Glu | Ile | Leu | Ala | Lys | Phe | Phe | Pro | Glu | Tyr | Asn |
| | | | 260 | | | | | 265 | | | | | 270 | | |

| Val | Pro | Thr | Lys | Cys | Ser | Asp | Glu | Val | Asn | Pro | Arg | Val | Lys | Pro | Tyr |
| | | | 275 | | | | | 280 | | | | | 285 | | |

| Lys | Phe | Ser | Asn | Gln | Lys | Leu | Arg | Asp | Leu | Gly | Leu | Glu | Phe | Thr | Pro |
| | 290 | | | | | 295 | | | | | 300 | | | | |

| Val | Lys | Gln | Cys | Leu | Tyr | Glu | Thr | Val | Lys | Ser | Leu | Gln | Glu | Lys | Gly |
| 305 | | | | | 310 | | | | | 315 | | | | | 320 |

| His | Leu | Pro | Val | Pro | Pro | Pro | Glu | Asp | Ser | Val | Arg | Ile | Gln | Gly |
| | | | | 325 | | | | | 330 | | | | | 335 |

<210> SEQ ID NO 19
<211> LENGTH: 336
<212> TYPE: PRT
<213> ORGANISM: Eucalyptus gunnii

<400> SEQUENCE: 19

```
Met Pro Val Asp Ala Leu Pro Gly Ser Gly Gln Thr Val Cys Val Thr
 1               5                  10                  15
Gly Ala Gly Gly Phe Ile Ala Ser Trp Ile Val Lys Leu Leu Leu Glu
            20                  25                  30
Arg Gly Tyr Thr Val Arg Gly Thr Val Arg Asn Pro Asp Asp Pro Lys
        35                  40                  45
Asn Gly His Leu Arg Glu Leu Glu Gly Ala Ser Glu Arg Leu Thr Leu
    50                  55                  60
Tyr Lys Gly Asp Leu Met Asp Tyr Gly Ser Leu Glu Glu Ala Ile Lys
 65                  70                  75                  80
Gly Cys Asp Gly Val Val His Thr Ala Ser Pro Val Thr Asp Asp Pro
                85                  90                  95
Glu Gln Met Val Glu Pro Ala Val Ile Gly Thr Lys Asn Val Ile Val
            100                 105                 110
Ala Ala Ala Glu Ala Lys Val Arg Arg Val Val Phe Thr Ser Ser Ile
        115                 120                 125
Gly Ala Val Thr Met Asp Pro Asn Arg Gly Pro Asp Val Val Val Asp
    130                 135                 140
Glu Ser Cys Trp Ser Asp Leu Glu Phe Cys Lys Ser Thr Lys Asn Trp
145                 150                 155                 160
Tyr Cys Tyr Gly Lys Ala Val Ala Glu Lys Ala Ala Trp Pro Glu Ala
                165                 170                 175
Lys Glu Arg Gly Val Asp Leu Val Val Ile Asn Pro Val Leu Val Leu
            180                 185                 190
Gly Pro Leu Leu Gln Ser Thr Ile Asn Ala Ser Ile Ile His Ile Leu
        195                 200                 205
Lys Tyr Leu Thr Gly Ser Ala Lys Thr Tyr Ala Asn Ser Val Gln Ala
    210                 215                 220
Tyr Val His Val Lys Asp Val Ala Leu Ala His Val Leu Val Leu Glu
225                 230                 235                 240
Thr Pro Ser Ala Ser Gly Arg Tyr Leu Cys Ala Glu Ser Val Leu His
                245                 250                 255
Arg Gly Asp Val Val Glu Ile Leu Ala Lys Phe Phe Pro Glu Tyr Asn
            260                 265                 270
Val Pro Thr Lys Cys Ser Asp Glu Val Asn Pro Arg Val Lys Pro Tyr
        275                 280                 285
Lys Phe Ser Asn Gln Lys Leu Arg Asp Leu Gly Leu Glu Phe Thr Pro
    290                 295                 300
Val Lys Gln Cys Leu Tyr Glu Thr Val Lys Ser Leu Gln Glu Lys Gly
305                 310                 315                 320
His Leu Pro Val Pro Ser Pro Glu Asp Ser Val Arg Ile Gln Gly
                325                 330                 335
```

<210> SEQ ID NO 20
<211> LENGTH: 336
<212> TYPE: PRT
<213> ORGANISM: Eucalyptus globulus
<220> FEATURE:
<221> NAME/KEY: misc_feature
<222> LOCATION: (175)..(175)
<223> OTHER INFORMATION: Xaa can be any naturally occurring amino acid

<400> SEQUENCE: 20

```
Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Leu Leu Glu
            20                  25                  30

Arg Gly Tyr Thr Val Arg Gly Thr Val Arg Asn Pro Asp Asp Pro Lys
        35                  40                  45

Asn Gly His Leu Arg Glu Leu Asp Gly Ala Ser Glu Arg Leu Thr Leu
    50                  55                  60

Tyr Lys Gly Asp Leu Met Asp Tyr Glu Ser Leu Arg Glu Ala Ile Met
65                  70                  75                  80

Gly Cys Asp Gly Val Val His Thr Ala Ser Pro Val Thr Asp Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Gly Pro Asp Val Val Val Asp
130                 135                 140

Glu Ser Cys Trp Ser Asp Leu Glu Phe Cys Lys Ser Thr Lys Asn Trp
145                 150                 155                 160

Tyr Cys Tyr Gly Lys Ala Val Ala Glu Lys Ala Ala Cys Ala Xaa Ala
                165                 170                 175

Lys Glu Arg Gly Val Asp Leu Val Val Ile Asn Pro Val Leu Val Leu
            180                 185                 190

Gly Pro Leu Leu Gln Ser Thr Ile Asn Ala Ser Ile Ile His Ile Leu
        195                 200                 205

Lys Tyr Leu Thr Gly Ser Ala Lys Thr Tyr Ala Asn Ser Val Gln Ala
210                 215                 220

Tyr Val His Val Lys Asp Val Ala Leu Ala His Val Leu Val Leu Glu
225                 230                 235                 240

Thr Pro Ser Ala Ser Gly Arg Tyr Leu Cys Ala Glu Ser Val Leu His
                245                 250                 255

Arg Gly Asp Val Val Glu Ile Leu Ala Lys Phe Phe Pro Glu Tyr Asn
            260                 265                 270

Val Pro Thr Lys Cys Ser Asp Glu Val Asn Pro Arg Val Lys Pro Tyr
        275                 280                 285

Lys Phe Ser Asn Gln Lys Leu Lys Asp Leu Gly Leu Glu Phe Thr Pro
290                 295                 300

Val Lys Gln Cys Leu Tyr Glu Thr Val Lys Ser Leu Gln Glu Lys Gly
305                 310                 315                 320

His Leu Pro Val Pro Pro Pro Glu Asp Ser Val Arg Ile Gln Gly
                325                 330                 335
```

<210> SEQ ID NO 21
<211> LENGTH: 336
<212> TYPE: PRT
<213> ORGANISM: Eucalyptus pilularis

<400> SEQUENCE: 21

```
Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Phe Leu Glu
            20                  25                  30
```

Arg Gly Tyr Thr Val Arg Gly Thr Val Arg Asn Pro Asp Pro Lys
            35                  40                  45

Asn Gly His Leu Arg Glu Leu Glu Gly Ala Ser Glu Arg Leu Thr Leu
 50                  55                  60

Tyr Lys Gly Asp Leu Met Asp Tyr Glu Ser Leu Arg Glu Ala Ile Met
 65                  70                  75                  80

Gly Cys Asp Gly Val Val His Thr Ala Ser Pro Val Thr Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Gln Arg Val Val Phe Thr Ser Ser Val
            115                 120                 125

Gly Ala Ile Thr Met Asp Pro Asn Arg Gly Leu Asp Val Val Asp
            130                 135                 140

Glu Ser Cys Trp Ser Asp Leu Asp Phe Cys Lys Ser Thr Lys Asn Trp
145                 150                 155                 160

Tyr Cys Tyr Gly Lys Ala Val Ala Glu Lys Ser Ala Cys Ala Glu Ala
                165                 170                 175

Lys Glu Arg Gly Val Asp Leu Val Val Ile Asn Pro Val Leu Val Leu
            180                 185                 190

Gly Pro Leu Leu Gln Ser Thr Val Asn Ala Ser Ile Ile His Ile Leu
            195                 200                 205

Lys Tyr Leu Thr Gly Ser Ala Lys Thr Tyr Ala Asn Ser Val Gln Ala
            210                 215                 220

Tyr Val His Val Lys Asp Val Ala Leu Ala His Ile Leu Val Phe Glu
225                 230                 235                 240

Thr Pro Ser Ala Ser Gly Arg Tyr Leu Cys Ala Glu Ser Val Leu His
                245                 250                 255

Arg Gly Asp Val Val Glu Ile Leu Ala Lys Phe Phe Pro Glu Tyr Asn
            260                 265                 270

Leu Pro Thr Lys Cys Ser Asp Glu Val Asn Pro Arg Val Lys Pro Tyr
            275                 280                 285

Lys Phe Ser Asn Gln Lys Leu Arg Asp Leu Gly Leu Glu Phe Thr Pro
            290                 295                 300

Val Lys Gln Cys Leu Tyr Glu Thr Val Lys Ser Leu Gln Glu Lys Gly
305                 310                 315                 320

His Leu Ala Ile Pro Ser Pro Glu Asp Ser Val Arg Ile Arg Gly
                325                 330                 335

<210> SEQ ID NO 22
<211> LENGTH: 338
<212> TYPE: PRT
<213> ORGANISM: Populus trichocarpa

<400> SEQUENCE: 22

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
            35                  40                  45

Pro Lys Asn Ser His Leu Arg Glu Leu Glu Gly Ala Glu Glu Arg Leu
 50                  55                  60

Thr Leu Cys Lys Ala Asp Leu Leu Asp Tyr Glu Ser Leu Lys Glu Ala

```
            65                  70                  75                  80
Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Ile Ala Ala Glu Ala Lys Val Arg Arg Val Phe Thr Ser
            115                 120                 125

Ser Ile Gly Ala Val Tyr Met Asp Pro Asn Lys Gly Pro Asp Val Val
            130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
                165                 170                 175

Met Ala Lys Glu Lys Gly Val Asp Leu Val Val Val Asn Pro Val Leu
            180                 185                 190

Val Leu Gly Pro Leu Leu Gln Pro Thr Val Asn Ala Ser Ile Thr His
                195                 200                 205

Ile Leu Lys Tyr Leu Thr Gly Ser Ala Lys Thr Tyr Ala Asn Ser Val
            210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
                260                 265                 270

Tyr Pro Ile Pro Thr Lys Cys Ser Asp Glu Lys Asn Pro Arg Lys Gln
                275                 280                 285

Pro Tyr Lys Phe Ser Asn Gln Lys Leu Arg Asp Leu Gly Phe Glu Phe
            290                 295                 300

Thr Pro Val Lys Gln Cys Leu Tyr Glu Thr Val Lys Ser Leu Gln Glu
305                 310                 315                 320

Lys Gly His Leu Pro Ile Pro Lys Gln Ala Ala Glu Glu Ser Leu Lys
                325                 330                 335

Ile Gln

<210> SEQ ID NO 23
<211> LENGTH: 338
<212> TYPE: PRT
<213> ORGANISM: Populus tomentosa

<400> SEQUENCE: 23

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
            35                  40                  45

Pro Lys Asn Ser His Leu Arg Glu Leu Glu Gly Ala Gln Glu Arg Leu
50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
```

```
              100                 105                 110
Ile Ile Ala Ala Ala Glu Ala Lys Val Arg Arg Val Val Phe Thr Ser
            115                 120                 125

Ser Ile Gly Ala Val Tyr Met Asp Pro Asn Lys Gly Pro Asp Val Val
            130                 135                 140

Ile Asp Glu Ser Cys Trp Ser Asp Leu Glu Phe Cys Lys Asn Thr Lys
145                 150                 155                 160

Asn Trp Tyr Cys Tyr Gly Lys Ala Val Ala Glu Gln Ala Ala Trp Asp
                165                 170                 175

Met Ala Lys Glu Lys Gly Val Asp Leu Val Val Asn Pro Val Leu
            180                 185                 190

Val Leu Gly Pro Leu Leu Gln Pro Thr Val Asn Ala Ser Ile Val His
            195                 200                 205

Ile Leu Lys Tyr Leu Thr Gly Ser Ala Lys Thr Tyr Ala Asn Ser Val
            210                 215                 220

Gln Ala Tyr Val His Val Arg Asp Val Ala Leu Ala His Ile Leu Val
225                 230                 235                 240

Phe Glu Thr Pro Ser Ala Ser Gly Arg Tyr Leu Cys Ser Glu Ser Val
                245                 250                 255

Leu His Arg Gly Glu Val Val Glu Ile Leu Ala Lys Phe Phe Pro Glu
                260                 265                 270

Tyr Pro Ile Pro Thr Lys Cys Ser Asp Glu Lys Asn Pro Arg Lys Gln
            275                 280                 285

Pro Tyr Lys Phe Ser Asn Gln Lys Leu Arg Asp Leu Gly Phe Glu Phe
            290                 295                 300

Thr Pro Val Lys Gln Cys Leu Tyr Glu Thr Val Lys Ser Leu Gln Glu
305                 310                 315                 320

Arg Gly His Leu Pro Ile Pro Lys Gln Ala Ala Glu Glu Ser Val Lys
                325                 330                 335

Ile Gln

<210> SEQ ID NO 24
<211> LENGTH: 338
<212> TYPE: PRT
<213> ORGANISM: Hevea brasiliensis

<400> SEQUENCE: 24

Met Pro Val Asp Thr Ser Ser Leu Ser Gly His Gly Gln Thr Val Cys
1               5                   10                  15

Val Thr Gly Ala Gly Gly Phe Ile Ala Ser Trp Ile Val Lys Leu Leu
            20                  25                  30

Leu Glu Arg Gly Tyr Thr Val Lys Gly Thr Val Arg Asn Pro Asp Asp
            35                  40                  45

Pro Lys Asn Ser His Leu Arg Glu Leu Glu Gly Ala Lys Glu Arg Leu
        50                  55                  60

Thr Leu Cys Lys Ala Asp Leu Leu Asp Tyr Glu Ser Leu Arg Lys Ala
65                  70                  75                  80

Ile Met Gly Cys Asp Gly Val Phe His Ala Ala Ser Pro Val Thr Asp
                85                  90                  95

Asp Pro Glu Gln Met Val Glu Pro Ala Val Asn Gly Thr Lys Asn Val
            100                 105                 110

Val Ile Ala Ala Ala Glu Ala Lys Val Arg Arg Val Val Phe Thr Ser
            115                 120                 125

Ser Ile Gly Ala Val Tyr Met Asp Pro Asn Arg Asn Pro Asp Val Val
```

```
                130               135               140
Val Asp Glu Ser Cys Trp Ser Asp Leu Asp Phe Cys Lys Asn Thr Lys
145                 150                 155                 160

Asn Trp Tyr Cys Tyr Gly Lys Ala Val Ala Glu Gln Ala Ala Trp Glu
                165                 170                 175

Val Ala Lys Glu Lys Gly Val Asp Leu Val Ala Val Asn Pro Val Leu
            180                 185                 190

Val Leu Gly Pro Leu Leu Gln Ser Thr Val Asn Ala Ser Ile Ile His
            195                 200                 205

Ile Leu Lys Tyr Leu Thr Gly Ser Ala Lys Thr Tyr Ala Asn Ser Val
        210                 215                 220

Gln Ala Tyr Ala His Val Lys Asp Val Ala Leu Ala His Ile Leu Val
225                 230                 235                 240

Tyr Glu Ile Pro Ser Ala Ser Gly Arg Tyr Leu Cys Ala Glu Ser Val
                245                 250                 255

Leu His Arg Gly Glu Val Val Glu Ile Leu Ala Lys Ser Phe Pro Glu
            260                 265                 270

Tyr Pro Ile Pro Thr Arg Cys Ser Asp Glu Lys Asn Pro Arg Ala Lys
            275                 280                 285

Pro Tyr Lys Phe Ser Asn Gln Lys Leu Lys Asp Leu Gly Met Glu Phe
        290                 295                 300

Thr Pro Val Lys Gln Cys Leu Tyr Glu Thr Val Lys Ser Leu Gln Glu
305                 310                 315                 320

Arg Gly His Leu Pro Ile Pro Lys Gln Pro Glu Asp Ser Ile Arg Ile
                325                 330                 335

Gln Ser

<210> SEQ ID NO 25
<211> LENGTH: 338
<212> TYPE: PRT
<213> ORGANISM: Gossypium hirsutum

<400> SEQUENCE: 25

Met Pro Ile Glu Ser Ser Ser Thr Asn Gly Pro Thr Val Cys Val Thr
1               5                   10                  15

Gly Ala Gly Gly Phe Ile Ala Ser Trp Ile Val Lys Leu Leu Leu Glu
            20                  25                  30

Lys Gly Tyr Thr Val Lys Gly Thr Val Arg Asn Pro Asp Asp Pro Lys
        35                  40                  45

Asn Cys His Leu Arg Glu Leu Glu Gly Ala Lys Glu Arg Leu Ser Leu
    50                  55                  60

His Lys Ala Asp Leu Leu Asp Tyr Gln Ser Leu Lys Glu Ala Ile Ser
65                  70                  75                  80

Gly Cys Asp Gly Val Phe His Thr Ala Ser Pro Val Thr Asp Asp Pro
                85                  90                  95

Glu Gln Met Val Glu Pro Ala Val Ile Gly Thr Lys Asn Val Ile Met
            100                 105                 110

Ala Ala Ala Glu Ala Lys Val Arg Arg Val Val Phe Thr Ser Ser Ile
        115                 120                 125

Gly Ala Val Tyr Met Asp Pro Asn Arg Ser Pro Asp Val Val Val Asp
    130                 135                 140

Glu Ser Cys Trp Ser Asp Leu Glu Phe Cys Lys Asn Thr Lys Asn Trp
145                 150                 155                 160

Tyr Cys Tyr Gly Lys Ala Val Ala Glu Gln Ala Ala Trp Glu Thr Ala
```

```
                    165                 170                 175
Lys Glu Lys Gly Val Asp Leu Val Ala Ile Thr Pro Val Leu Val Leu
            180                 185                 190

Gly Pro Leu Leu Gln Pro Thr Val Asn Ala Ser Ile Val His Ile Leu
        195                 200                 205

Lys Tyr Leu Thr Gly Ser Ala Lys Thr Tyr Ala Asn Ser Val Gln Ala
    210                 215                 220

Tyr Val His Val Arg Asp Val Ala Leu Ala His Leu Leu Val Tyr Glu
225                 230                 235                 240

Asn Pro Ser Ala Ser Gly Arg Tyr Leu Cys Ala Glu Ser Val Leu His
                245                 250                 255

Arg Gly Glu Val Val Glu Ile Leu Ala Lys Phe Phe Pro Glu Tyr Pro
            260                 265                 270

Ile Pro Thr Lys Cys Ser Asp Glu Lys Asn Pro Arg Ala Lys Pro Tyr
        275                 280                 285

Lys Phe Thr Asn Gln Lys Leu Arg Asp Leu Gly Leu Glu Phe Thr Pro
    290                 295                 300

Val Lys Gln Cys Leu Tyr Glu Thr Val Lys Ser Leu Gln Glu Lys Gly
305                 310                 315                 320

His Leu Pro Ile Pro Ala Gln His Gln Glu Asp Ser Gly Leu Arg Ile
                325                 330                 335

Gln Ser

<210> SEQ ID NO 26
<211> LENGTH: 338
<212> TYPE: PRT
<213> ORGANISM: Hibiscus cannabinus

<400> SEQUENCE: 26

Met Pro Thr Asp Thr Pro Ser Ser Asn Gly Met Thr Val Cys Val Thr
1               5                   10                  15

Gly Ala Gly Gly Phe Ile Ala Ser Trp Met Val Lys Leu Leu Leu Glu
            20                  25                  30

Lys Gly Tyr Ser Val Lys Gly Thr Val Arg Asn Pro Asp Asp Pro Lys
        35                  40                  45

Asn Ser His Leu Arg Glu Leu Glu Gly Ala Lys Glu Arg Leu Ser Leu
    50                  55                  60

His Arg Ala Asp Leu Leu Asp Tyr Pro Ser Leu Lys Glu Ala Ile Ser
65                  70                  75                  80

Gly Cys Asp Gly Val Phe His Thr Ala Ser Pro Val Thr Asp Asp Pro
                85                  90                  95

Glu Gln Met Val Glu Pro Ala Val Asn Gly Thr Lys Asn Val Ile Met
            100                 105                 110

Ala Ala Ala Glu Ala Lys Val Arg Arg Val Val Phe Thr Ser Ser Ile
        115                 120                 125

Gly Ala Val Tyr Met Asp Pro Asn Arg Ser Pro Asp Val Val Val Asp
    130                 135                 140

Glu Ser Cys Trp Ser Asp Leu Glu Phe Cys Lys Asn Thr Lys Asn Trp
145                 150                 155                 160

Tyr Cys Tyr Gly Lys Ala Val Ala Glu Gln Ala Ala Trp Glu Thr Ala
                165                 170                 175

Lys Glu Lys Gly Val Asp Leu Val Val Val Ala Pro Val Leu Val Leu
            180                 185                 190

Gly Pro Leu Leu Gln Ser Thr Val Asn Ala Ser Thr Val His Ile Leu
```

```
            195                 200                 205
Lys Tyr Leu Thr Gly Ser Ala Lys Thr Tyr Ala Asn Ser Val Gln Ala
    210                 215                 220

Tyr Val His Val Arg Asp Val Ala Leu Ala His Ile Leu Val Phe Glu
225                 230                 235                 240

Asn Pro Ser Ala Ser Gly Arg Tyr Leu Cys Ala Glu Ser Val Leu His
                245                 250                 255

Arg Gly Glu Val Val Glu Ile Leu Ala Lys Leu Phe Pro Glu Tyr Pro
            260                 265                 270

Val Pro Thr Lys Cys Ser Asp Glu Ser Asn Pro Arg Lys Lys Pro Tyr
            275                 280                 285

Lys Phe Ser Asn Gln Lys Leu Arg Glu Leu Gly Leu Glu Phe Thr Pro
            290                 295                 300

Val Lys Gln Cys Leu Tyr Glu Thr Val Lys Ser Leu Gln Glu Lys Gly
305                 310                 315                 320

His Leu Ala Ile Pro Ala Gln Gln Gln Glu Asp Pro Val Leu Arg Ile
                325                 330                 335

Gln Ser
```

<210> SEQ ID NO 27
<211> LENGTH: 336
<212> TYPE: PRT
<213> ORGANISM: Betula luminifera

<400> SEQUENCE: 27

```
Met Pro Phe Asp Cys Ser Ser Ala Ser Gly Leu Thr Val Cys Val Thr
1               5                   10                  15

Gly Ala Gly Gly Phe Ile Ala Ser Trp Ile Val Lys Leu Leu Leu Glu
            20                  25                  30

Lys Gly Tyr Thr Val Lys Gly Thr Leu Arg Asn Pro Asp Asp Pro Lys
        35                  40                  45

Asn Ala His Leu Lys Glu Leu Glu Gly Ala Lys Glu Arg Leu Thr Leu
    50                  55                  60

Trp Lys Thr Asp Leu Leu Asp Tyr Glu Ser Leu Lys Ala Ala Ile Asp
65                  70                  75                  80

Gly Cys Asp Gly Val Ile His Thr Ala Ser Pro Val Thr Asp Asp Pro
                85                  90                  95

Glu Leu Met Val Glu Pro Ala Val Asp Gly Thr Lys Asn Val Ile Ile
            100                 105                 110

Ala Ala Ala Glu Thr Lys Val Arg Arg Val Val Phe Thr Ser Ser Ile
        115                 120                 125

Gly Ala Val Tyr Met Asp Pro Asn Arg Gly Pro Asp Val Val Val Asp
    130                 135                 140

Glu Ser Cys Trp Ser Asp Leu Glu Phe Cys Lys Asn Thr Lys Asn Trp
145                 150                 155                 160

Tyr Cys Tyr Gly Lys Ala Val Ala Glu Gln Ala Ala Trp Glu Val Ala
                165                 170                 175

Glu Glu Lys Gly Val Asp Leu Val Val Val Asn Pro Val Leu Val Leu
            180                 185                 190

Gly Pro Leu Leu Gln Pro Asn Val Asn Ala Ser Val Val His Val Leu
        195                 200                 205

Lys Tyr Leu Thr Gly Ser Ala Lys Thr Tyr Ala Asn Ser Val Gln Ala
    210                 215                 220

Tyr Val His Val Arg Asp Val Ala Leu Ala His Ile Leu Val Leu Glu
```

```
                225                 230                 235                 240
Thr Pro Ser Ala Ser Gly Arg Tyr Leu Cys Ala Glu Ala Val Leu His
                    245                 250                 255

Arg Gly Asp Val Val Gln Ile Leu Ala Lys Leu Phe Pro Glu Tyr Pro
                260                 265                 270

Ile Pro Thr Met Cys Ser Asp Glu Lys Asn Pro Arg Ala Lys Pro Tyr
                    275                 280                 285

Lys Phe Ser Asn Gln Lys Leu Lys Asp Leu Gly Leu Glu Phe Thr Pro
                290                 295                 300

Val Lys Gln Cys Leu Tyr Glu Thr Val Lys Ser Leu Gln Glu Lys Gly
305                 310                 315                 320

Val Leu Pro Ile Pro Thr Gln Gln Glu Glu Pro Val Arg Ile Gln Ser
                    325                 330                 335

<210> SEQ ID NO 28
<211> LENGTH: 332
<212> TYPE: PRT
<213> ORGANISM: Solanum lycopersicum

<400> SEQUENCE: 28

Met Pro Ser Val Ser Gly Arg Val Val Cys Val Thr Gly Ala Gly Gly
1               5                   10                  15

Phe Ile Ala Ser Trp Leu Val Lys Leu Leu Leu Glu Lys Gly Tyr Thr
                20                  25                  30

Val Arg Gly Thr Val Arg Asn Pro Asp Asp Pro Lys Asn Cys His Leu
                35                  40                  45

Arg Glu Leu Glu Gly Ala Lys Glu Arg Leu Thr Leu Cys Arg Gly Asp
50                  55                  60

Leu Leu Asp Tyr Gln Ser Leu Arg Glu Ala Ile Asn Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Thr Ala Ala Ala Glu
                100                 105                 110

Ala Asn Val Arg Arg Val Val Phe Thr Ser Ser Ile Gly Ala Val Tyr
                115                 120                 125

Met Asp Pro Ser Arg Asp Pro Glu Lys Val Val Asp Glu Thr Cys Trp
130                 135                 140

Ser Asp Pro Asp Phe Cys Lys Asn Thr Lys Asn Trp Tyr Cys Tyr Gly
145                 150                 155                 160

Lys Met Val Ala Glu Gln Ala Ala Trp Asp Glu Ala Arg Glu Lys Gly
                165                 170                 175

Val Asp Leu Val Ala Ile Asn Pro Val Leu Val Leu Gly Pro Leu Leu
                180                 185                 190

Gln Asn Thr Val Asn Ala Ser Val Leu His Ile Leu Lys Tyr Leu Thr
                195                 200                 205

Gly Ser Ala Lys Thr Tyr Ala Asn Ser Val Gln Ala Tyr Val His Val
                210                 215                 220

Lys Asp Val Ala Leu Ala His Ile Leu Leu Tyr Glu Thr Pro Ser Ala
225                 230                 235                 240

Ser Gly Arg Tyr Leu Cys Ala Glu Ser Val Leu His Arg Gly Asp Ile
                245                 250                 255

Val Glu Ile Leu Ala Lys Phe Phe Pro Glu Tyr Pro Ile Pro Thr Lys
                260                 265                 270
```

```
Cys Ser Asp Val Thr Lys Pro Arg Val Lys Pro Tyr Lys Phe Ser Asn
            275                 280                 285

Gln Lys Leu Lys Asp Leu Gly Met Glu Phe Thr Pro Val Lys Gln Cys
        290                 295                 300

Leu Tyr Glu Thr Val Lys Ser Leu Gln Glu Lys Gly His Leu Pro Ile
305                 310                 315                 320

Pro Thr Gln Lys Asp Glu Ile Ile Arg Ile Gln Thr
                325                 330
```

```
<210> SEQ ID NO 29
<211> LENGTH: 332
<212> TYPE: PRT
<213> ORGANISM: Solanum tuberosum

<400> SEQUENCE: 29

Met Pro Ser Glu Ser Gly Lys Val Val Cys Val Thr Gly Ala Gly Gly
1               5                   10                  15

Phe Ile Ala Ser Trp Leu Val Lys Leu Leu Glu Lys Gly Tyr Thr
            20                  25                  30

Val Arg Gly Thr Val Arg Asn Pro Asp Asp Pro Lys Asn Gly His Leu
            35                  40                  45

Lys Glu Leu Glu Gly Ala Lys Glu Arg Leu Ile Leu Arg Ala Asp
    50                  55                  60

Leu Leu Asp Tyr Gln Ser Leu Arg Glu Ala Ile Tyr Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Thr Ala Ala Ala Glu
            100                 105                 110

Ala Lys Val Gly Arg Val Val Phe Thr Ser Ser Ile Gly Thr Val Tyr
            115                 120                 125

Met Asp Pro Asn Arg Ala Pro Asp Lys Val Val Asp Glu Thr Cys Trp
130                 135                 140

Ser Asp Leu Gly Phe Cys Lys Asn Thr Lys Asn Trp Tyr Cys Tyr Gly
145                 150                 155                 160

Lys Thr Val Ala Glu Lys Thr Ala Trp Asp Glu Ala Arg Glu Lys Gly
                165                 170                 175

Val Asp Leu Val Val Ile Asn Pro Val Leu Val Leu Gly Pro Leu Leu
            180                 185                 190

Gln Pro Thr Val Asn Ala Ser Val Leu His Ile Leu Lys Tyr Leu Thr
            195                 200                 205

Gly Ser Ala Lys Thr Tyr Ala Asn Ser Ile Gln Ala Tyr Val His Val
210                 215                 220

Lys Asp Val Ala Leu Ala His Ile Leu Leu Tyr Glu Ala Pro Ser Ala
225                 230                 235                 240

Ser Gly Arg Tyr Ile Cys Ala Glu Ser Val Leu His Arg Gly Asp Val
                245                 250                 255

Val Glu Ile Leu Ala Lys Phe Phe Pro Glu Tyr Pro Ile Pro Thr Lys
            260                 265                 270

Cys Ser Asp Glu Thr Arg Pro Arg Ala Lys Pro Tyr Lys Phe Thr Asn
            275                 280                 285

Gln Lys Leu Lys Asp Leu Gly Leu Gly Phe Thr Pro Val Lys Gln Cys
        290                 295                 300

Leu Tyr Glu Thr Val Lys Ser Leu Gln Glu Lys Gly His Leu Pro Ile
305                 310                 315                 320
```

```
Pro Thr Gln Asn Asp Glu Pro Ile Lys Ile His Ser
                325                 330

<210> SEQ ID NO 30
<211> LENGTH: 336
<212> TYPE: PRT
<213> ORGANISM: Codonopsis lanceolate

<400> SEQUENCE: 30

Met Pro Pro Val Ser Asn Gln Val Ile Cys Val Thr Gly Ala Gly Gly
1               5                   10                  15

Phe Ile Ala Ser Trp Met Val Lys Leu Leu Glu Lys Gly Tyr Ser
            20                  25                  30

Val Arg Gly Thr Val Arg Asn Pro Asp Asp Pro Lys Asn Ser His Leu
            35                  40                  45

Arg Asp Leu Glu Gly Ala Lys Asp Arg Leu Thr Leu Cys Lys Ala Asp
    50                  55                  60

Leu Leu Asp Tyr Gln Ser Leu Leu Glu Ala Ile Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Val Ala Ala Ala Glu
            100                 105                 110

Ala Lys Cys Arg Arg Val Val Phe Thr Ser Ser Ile Gly Ala Val Tyr
        115                 120                 125

Met Asp Pro Asn Arg Ser Pro Asp Ala Val Val Asp Glu Thr Cys Trp
130                 135                 140

Ser Asp Leu Glu Phe Cys Lys Asn Thr Lys Asn Trp Tyr Cys Tyr Gly
145                 150                 155                 160

Lys Ala Val Ala Glu Gln Ala Ala Trp Asp Glu Ala Lys Val Arg Gly
                165                 170                 175

Val Asp Leu Val Val Val Asn Pro Val Leu Val Leu Gly Pro Leu Leu
            180                 185                 190

Gln His Thr Val Asn Ala Ser Ile Val His Val Gln Lys Tyr Leu Thr
        195                 200                 205

Gly Ser Ala Lys Thr Tyr Ala Asn Ser Val Gln Ala Tyr Val His Val
    210                 215                 220

Arg Asp Val Ala Leu Ala His Ile Leu Leu Phe Glu Thr Pro Ser Ala
225                 230                 235                 240

Ser Gly Arg Tyr Leu Cys Ala Glu Ser Val Leu His Arg Gly Glu Val
                245                 250                 255

Val Glu Ile Leu Ala Lys Phe Phe Pro Glu Tyr Pro Ile Pro Thr Lys
            260                 265                 270

Cys Lys Asp Asp Gly Lys Pro Arg Ala Lys Pro Tyr Lys Phe Ser Asn
        275                 280                 285

Gln Lys Leu Lys Asp Leu Gly Leu Glu Phe Thr Pro Val Lys Gln Gly
    290                 295                 300

Leu Tyr Glu Thr Val Lys Ser Leu Gln Glu Lys Gly His Leu Pro Val
305                 310                 315                 320

Leu Ser Pro Pro Pro Gln Gln Thr Asp Asp Ser Ile Arg Ile Gln Ser
                325                 330                 335

<210> SEQ ID NO 31
<211> LENGTH: 347
<212> TYPE: PRT
```

<213> ORGANISM: Vaccinium corymbosum

<400> SEQUENCE: 31

```
Met Pro Ser Val Ser Gly Gln Thr Val Cys Val Thr Gly Ala Gly Gly
1               5                   10                  15

Phe Ile Ala Ser Trp Met Val Lys Leu Leu Glu Lys Gly Tyr Thr
            20                  25                  30

Val Arg Gly Thr Val Arg Asn Pro Asp Asp Pro Lys Asn Ser His Leu
            35                  40                  45

Arg Asn Leu Glu Gly Ala Glu Arg Leu Thr Leu Cys Lys Ala Asp
    50                  55                  60

Leu Leu Asp Phe Gly Ser Leu Arg Gln Val Ile Asn Gly Cys Asp Gly
65                  70                  75                  80

Val Phe His Thr Ala Ser Pro Val Thr Asp Asp Pro Glu Glu Met Val
                85                  90                  95

Glu Pro Ala Val Ile Gly Thr Lys Asn Val Ile Val Ala Ala Ala Glu
            100                 105                 110

Ala Lys Val Arg Arg Val Val Phe Thr Ser Ser Ile Gly Ala Val Thr
        115                 120                 125

Met Asp Pro Asn Arg Gly Pro Asp Thr Val Val Asp Glu Ser Cys Trp
130                 135                 140

Ser Asp Leu Glu Phe Cys Lys Asn Thr Lys Asn Trp Tyr Cys Tyr Gly
145                 150                 155                 160

Lys Ala Val Ala Glu Gln Ala Ala Trp Asp Glu Ala Lys Asp Lys Gly
                165                 170                 175

Val Asp Leu Val Val Val Thr Pro Val Leu Val Met Gly Pro Leu Leu
            180                 185                 190

Gln Pro Thr Leu Asn Ala Ser Ile Ile His Val Leu Lys Tyr Leu Asn
        195                 200                 205

Gly Ser Ala Lys Thr Tyr Ala Asn Ser Val Gln Ala Tyr Val His Val
    210                 215                 220

Lys Asp Val Ala Leu Ala His Ile Leu Val Tyr Glu Thr Pro Ser Ala
225                 230                 235                 240

Ser Gly Arg Tyr Leu Cys Ala Glu Ser Val Leu His Arg Gly Asp Val
                245                 250                 255

Val Glu Ile Leu Ala Lys Phe Phe Pro Glu Tyr Pro Ile Pro Thr Lys
            260                 265                 270

Cys Lys Asp Glu Thr Lys Pro Arg Ala Lys Pro Tyr Lys Phe Ser Asn
        275                 280                 285

Gln Lys Leu Lys Asp Leu Gly Leu Glu Phe Thr Pro Thr Lys Gln Ser
    290                 295                 300

Leu Tyr Glu Thr Val Lys Ser Leu Gln Asp Lys Gly His Leu Pro Ile
305                 310                 315                 320

Pro Thr His Leu Ser Arg Ile Met Asn Leu Leu Phe Ala Phe Thr Leu
                325                 330                 335

Glu Ile Arg Ser His Glu Gln Val Tyr Leu Pro
            340                 345
```

<210> SEQ ID NO 32
<211> LENGTH: 339
<212> TYPE: PRT
<213> ORGANISM: Fragaria x ananassa

<400> SEQUENCE: 32

```
Met Pro Ala Asp His Ser Ser Ser Leu Ser Gly His Gly Gln Thr Val
```

```
  1               5                  10                 15
Cys Val Thr Gly Ala Gly Gly Phe Ile Ala Ser Trp Leu Val Lys Leu
             20                 25                 30

Leu Leu Glu Arg Gly Tyr Asn Val Arg Gly Thr Val Arg Asn Pro Glu
             35                 40                 45

Asp Pro Lys Asn Ala His Leu Arg Glu Leu Gly Ala Lys Glu Arg
 50                 55                 60

Leu Ser Leu Arg Lys Ala Asp Leu Leu Asp Phe Glu Ser Leu Lys Glu
 65                 70                 75                 80

Ala Ile Asn Gly Cys Asp Gly Val Phe His Thr Ala Ser Pro Val Thr
                 85                 90                 95

Asp Asp Pro Glu Gln Met Val Glu Pro Ala Val Asn Gly Thr Lys Asn
                100                105                110

Val Ile Val Ala Ala Glu Ala Lys Val Lys Arg Val Val Phe Thr
             115                120                125

Ser Ser Ile Gly Ala Val Tyr Met Asp Pro Ala Arg Gly Pro Asp Val
             130                135                140

Val Val Asp Glu Ser Cys Trp Ser Asp Leu Glu Phe Cys Lys Asn Thr
145                150                155                160

Lys Asn Trp Tyr Cys Tyr Gly Lys Ala Val Ala Glu Gln Ala Ala Trp
                165                170                175

Glu Glu Ala Lys Glu Arg Gly Val Asp Leu Val Val Asn Pro Val
             180                185                190

Leu Val Leu Gly Pro Leu Leu Gln Pro Thr Ile Asn Ala Ser Ile Ile
             195                200                205

His Ile Leu Lys Tyr Leu Thr Gly Ser Ala Lys Thr Tyr Ala Asn Ser
210                215                220

Val Gln Ala Tyr Val His Val Lys Asp Val Ala Leu Ala His Ile Leu
225                230                235                240

Val Tyr Glu Thr Pro Ser Ala Ser Gly Arg Tyr Leu Cys Ala Glu Ser
                245                250                255

Val Leu His Arg Gly Asp Val Val Glu Ile Leu Ala Lys Phe Phe Pro
             260                265                270

Glu Tyr Pro Ile Pro Ser Lys Leu Lys Asp Asp Gly Lys Pro Arg Ala
             275                280                285

Ile Pro Tyr Lys Phe Ser Asn Gln Lys Leu Gln Asp Leu Gly Leu Glu
             290                295                300

Phe Thr Ser Val Lys Gln Ser Leu Tyr Asp Thr Val Lys Ser Leu Gln
305                310                315                320

Glu Lys Gly His Leu Lys Val Pro Thr Lys Gln Glu Glu Ser Ile
             325                330                335

Lys Ile Gln

<210> SEQ ID NO 33
<211> LENGTH: 348
<212> TYPE: PRT
<213> ORGANISM: Hordeum vulgare

<400> SEQUENCE: 33

Met Thr Val Val Asp Ala Ala Ala Val Ala Gln Glu Leu Pro Gly
 1               5                  10                 15

His Gly Gln Thr Val Cys Val Thr Gly Ala Ala Gly Tyr Ile Ala Ser
             20                 25                 30

Trp Leu Val Lys Leu Leu Leu Glu Arg Gly Tyr Thr Val Lys Gly Thr
```

```
              35                  40                  45
Val Arg Asn Pro Asp Asp Pro Lys Asn Ala His Leu Lys Ala Leu Asp
 50                  55                  60

Gly Ala Ala Glu Arg Leu Val Leu Cys Lys Ala Asp Leu Leu Asp Tyr
 65                  70                  75                  80

Asp Ala Ile Cys Ala Ala Val Glu Gly Cys His Gly Val Phe His Thr
                 85                  90                  95

Ala Ser Pro Val Thr Asp Pro Glu Gln Met Val Glu Pro Ala Val
                100                 105                 110

Arg Gly Thr Glu Tyr Val Ile Asp Ala Ala Asp Ala Gly Thr Val
                115                 120                 125

Arg Arg Val Val Phe Thr Ser Ser Ile Gly Ala Val Thr Met Asp Pro
130                 135                 140

Asn Arg Gly Pro Asp Val Val Asp Glu Ser Cys Trp Ser Asp Leu
145                 150                 155                 160

Glu Phe Cys Lys Lys Thr Lys Asn Trp Tyr Cys Tyr Gly Lys Ala Val
                165                 170                 175

Ala Glu Gln Ala Ala Trp Glu Lys Ala Arg Ala Arg Gly Val Asp Leu
                180                 185                 190

Val Val Val Asn Pro Val Leu Val Val Gly Pro Leu Leu Gln Pro Thr
                195                 200                 205

Val Asn Ala Ser Ala Ala His Ile Leu Lys Tyr Leu Asp Gly Ser Ala
                210                 215                 220

Arg Lys Tyr Ala Asn Ala Val Gln Ala Tyr Val Asp Val Arg Asp Val
225                 230                 235                 240

Ala Gly Ala His Leu Arg Val Phe Glu Ala Pro Gln Ala Ser Gly Arg
                245                 250                 255

Tyr Leu Cys Ala Glu Arg Val Leu His Arg Gln Asp Val Val His Ile
                260                 265                 270

Leu Ala Lys Leu Phe Pro Glu Tyr Pro Val Pro Thr Arg Cys Ser Asp
                275                 280                 285

Glu Val Asn Pro Arg Lys Gln Pro Tyr Lys Met Ser Asn Gln Lys Leu
                290                 295                 300

Gln Asp Leu Gly Leu Lys Phe Thr Pro Val Asn Asp Ser Leu Tyr Glu
305                 310                 315                 320

Thr Val Lys Ser Leu Gln Glu Lys Gly His Leu Pro Val Pro Arg Lys
                325                 330                 335

Asp Ile Leu Ala Pro Gln Leu Asp Gly Ala Thr Ala
                340                 345

<210> SEQ ID NO 34
<211> LENGTH: 349
<212> TYPE: PRT
<213> ORGANISM: Triticum aestivum

<400> SEQUENCE: 34

Met Thr Val Val Ala Ala Ala Ala Ala Ala Gln Glu Leu Pro
  1               5                  10                  15

Gly His Gly Gln Thr Val Cys Val Thr Gly Ala Ala Gly Tyr Ile Ala
                 20                  25                  30

Ser Trp Leu Val Lys Leu Leu Leu Glu Arg Gly Tyr Thr Val Lys Gly
                 35                  40                  45

Thr Val Arg Asn Pro Asp Asp Pro Lys Asn Ala His Leu Lys Ala Leu
 50                  55                  60
```

-continued

```
Asp Gly Ala Ala Glu Arg Leu Val Leu Cys Lys Ala Asp Leu Leu Asp
 65                  70                  75                  80

Tyr Asp Ala Ile Cys Ala Ala Val Glu Gly Cys His Gly Val Phe His
                 85                  90                  95

Thr Ala Ser Pro Val Thr Asp Pro Glu Gln Met Val Glu Pro Ala
            100                 105                 110

Val Arg Gly Thr Glu Tyr Val Ile Asn Ala Ala Asp Ala Gly Thr
        115                 120                 125

Val Arg Arg Val Gly Val Thr Ser Ser Ile Gly Ala Val Thr Met Asp
    130                 135                 140

Pro Asn Arg Gly Pro Asp Val Val Asp Glu Ser Cys Trp Ser Asp
145                 150                 155                 160

Leu Glu Phe Cys Lys Lys Thr Lys Asn Trp Tyr Cys Tyr Gly Lys Ala
                165                 170                 175

Val Ala Glu Gln Ala Ala Trp Glu Lys Ala Ala Arg Gly Val Asp
            180                 185                 190

Leu Val Val Val Asn Pro Val Leu Val Val Gly Pro Leu Leu Gln Pro
        195                 200                 205

Thr Val Asn Ala Ser Ala Ala His Ile Leu Lys Tyr Leu Asp Gly Ser
    210                 215                 220

Ala Lys Lys Tyr Ala Asn Ala Val Gln Ala Tyr Val Asn Val Arg Asp
225                 230                 235                 240

Val Ala Ala Ala His Val Arg Val Phe Glu Ala Pro Gly Ala Ser Gly
                245                 250                 255

Arg His Leu Cys Ala Glu Arg Val Leu His Arg Glu Asp Val Val His
            260                 265                 270

Ile Leu Gly Lys Leu Phe Pro Glu Tyr Pro Val Pro Thr Arg Cys Ser
        275                 280                 285

Asp Glu Val Asn Pro Arg Lys Gln Pro Tyr Lys Met Ser Asn Gln Lys
    290                 295                 300

Leu Gln Asp Leu Gly Leu Gln Phe Thr Pro Val Asn Asp Ser Leu Tyr
305                 310                 315                 320

Glu Thr Val Lys Ser Leu Gln Glu Lys Gly His Leu Pro Ala Pro Arg
                325                 330                 335

Lys Asp Ile Leu Pro Ala Glu Leu Asp Gly Ala Thr Ala
            340                 345
```

<210> SEQ ID NO 35
<211> LENGTH: 372
<212> TYPE: PRT
<213> ORGANISM: Saccharum officinarum

<400> SEQUENCE: 35

```
Met Thr Val Val Asp Ala Val Ser Thr Asp Ala Ala Gly Ala Pro Ala
  1               5                  10                  15

Ala Ala Ala Ala Pro Val Gln Gln Pro Gly Asn Gly Gln Thr Val Cys
                 20                  25                  30

Val Thr Gly Ala Ala Gly Tyr Ile Ala Ser Trp Leu Val Lys Leu Leu
             35                  40                  45

Leu Glu Lys Gly Tyr Thr Val Lys Gly Thr Val Arg Asn Pro Asp Asp
         50                  55                  60

Pro Lys Asn Ala His Leu Lys Ala Leu Asp Gly Ala Ala Glu Arg Leu
 65                  70                  75                  80

Ile Leu Cys Lys Ala Asp Leu Leu Asp Tyr Asp Ala Ile Cys Arg Ala
                 85                  90                  95
```

```
Val Gln Gly Cys His Gly Val Phe His Thr Ala Ser Pro Val Thr Asp
            100                 105                 110

Asp Pro Glu Gln Met Val Glu Pro Ala Val Arg Gly Thr Glu Tyr Val
            115                 120                 125

Ile Asn Ala Ala Glu Ala Gly Thr Val Arg Val Val Phe Thr
130                 135                 140

Ser Ser Ile Gly Ala Val Thr Met Asp Pro Ser Arg Gly Pro Asp Val
145                 150                 155                 160

Val Val Asp Glu Ser Cys Trp Ser Asp Leu Glu Phe Cys Lys Lys Thr
                165                 170                 175

Arg Asn Trp Tyr Cys Tyr Gly Lys Ala Val Ala Glu Gln Ala Ala Trp
            180                 185                 190

Asp Ala Ala Arg Gln Arg Gly Val Asp Leu Val Val Asn Pro Val
            195                 200                 205

Leu Val Val Gly Pro Leu Leu Gln Pro Thr Val Asn Ala Ser Ile Ala
    210                 215                 220

His Val Val Lys Tyr Leu Asp Gly Ser Ala Arg Thr Phe Ala Asn Ala
225                 230                 235                 240

Val Gln Ala Tyr Val Asp Val Arg Asp Val Ala Asp Ala His Leu Arg
                245                 250                 255

Val Phe Glu Ser Pro Arg Ala Ser Gly Arg Tyr Leu Cys Ala Glu Arg
                260                 265                 270

Val Leu His Arg Glu Asp Val Val Arg Ile Leu Ala Lys Leu Phe Pro
            275                 280                 285

Glu Tyr Pro Val Pro Thr Arg Cys Ser Asp Glu Val Asn Pro Arg Lys
            290                 295                 300

Gln Pro Tyr Lys Phe Ser Asn Gln Lys Leu Arg Asp Leu Gly Leu Glu
305                 310                 315                 320

Phe Arg Pro Val Ser Gln Ser Leu Tyr Asp Thr Val Lys Asn Leu Gln
                325                 330                 335

Glu Lys Gly His Leu Pro Val Leu Gly Glu Gln Thr Thr Glu Ala Asp
            340                 345                 350

Asp Lys Glu Ala Ala Pro Ala Ala Ala Glu Leu Gln Gln Gly Gly Ile
            355                 360                 365

Ala Ile Arg Ala
    370

<210> SEQ ID NO 36
<211> LENGTH: 367
<212> TYPE: PRT
<213> ORGANISM: Zea Mays

<400> SEQUENCE: 36

Met Thr Val Val Asp Ala Val Ser Ser Thr Asp Ala Gly Ala Ala Ala
1               5                   10                  15

Ala Thr Val Pro Ala Gly Asn Gly Gln Thr Val Cys Val Thr Gly Ala
            20                  25                  30

Ala Gly Tyr Ile Ala Ser Trp Leu Val Lys Leu Leu Glu Lys Gly
        35                  40                  45

Tyr Thr Val Lys Gly Thr Val Arg Asn Pro Asp Asp Pro Lys Asn Ala
    50                  55                  60

His Leu Lys Ala Leu Asp Gly Ala Ala Glu Arg Leu Ile Leu Cys Lys
65                  70                  75                  80

Ala Asp Leu Leu Asp Tyr Asp Ala Ile Cys Arg Ala Val Gln Gly Cys
```

Gln Gly Val Phe His Thr Ala Ser Pro Val Thr Asp Asp Pro Glu Gln
            85                  90                  95

Met Val Glu Pro Ala Val Arg Gly Thr Glu Tyr Val Ile Asn Ala Ala
        100                 105                 110

Ala Glu Ala Gly Thr Val Arg Val Val Phe Thr Ser Ser Ile Gly
        115                 120                 125

Ala Val Thr Met Asp Pro Lys Arg Gly Pro Asp Val Val Asp Glu
130                 135                 140

Ser Cys Trp Ser Asp Leu Glu Phe Cys Glu Lys Thr Arg Asn Trp Tyr
145                 150                 155                 160

Cys Tyr Gly Lys Ala Val Ala Glu Gln Ala Ala Trp Glu Thr Ala Arg
                165                 170                 175

Arg Arg Gly Val Asp Leu Val Val Val Asn Pro Val Leu Val Val Gly
                180                 185                 190

Pro Leu Leu Gln Ala Thr Val Asn Ala Ser Ile Ala His Ile Leu Lys
            195                 200                 205

Tyr Leu Asp Gly Ser Ala Arg Thr Phe Ala Asn Ala Val Gln Ala Tyr
210                 215                 220

Val Asp Val Arg Asp Val Ala Asp Ala His Leu Arg Val Phe Glu Ser
225                 230                 235                 240

Pro Arg Ala Ser Gly Arg His Leu Cys Ala Glu Arg Val Leu His Arg
                245                 250                 255

Glu Asp Val Val Arg Ile Leu Ala Lys Leu Phe Pro Glu Tyr Pro Val
                260                 265                 270

Pro Ala Arg Cys Ser Asp Glu Val Asn Pro Arg Lys Gln Pro Tyr Lys
            275                 280                 285

Phe Ser Asn Gln Lys Leu Arg Asp Leu Gly Leu Gln Phe Arg Pro Val
290                 295                 300

Ser Gln Ser Leu Tyr Asp Thr Val Lys Asn Leu Gln Glu Lys Gly His
305                 310                 315                 320

Leu Pro Val Leu Gly Glu Arg Thr Thr Thr Glu Ala Ala Asp Lys Asp
                325                 330                 335

Ala Pro Thr Ala Glu Met Gln Gln Gly Gly Ile Ala Ile Arg Ala
                340                 345                 350

355                 360                 365

<210> SEQ ID NO 37
<211> LENGTH: 363
<212> TYPE: PRT
<213> ORGANISM: Panicum virgatum

<400> SEQUENCE: 37

Met Thr Val Val Asp Ala Val Ser Ala Gly Ala Gly Asp Ala Ala Ala
1               5                   10                  15

Ala Val Pro Gln Pro Ala Gly Asn Gly Gln Thr Val Cys Val Thr Gly
            20                  25                  30

Ala Ala Gly Tyr Ile Ala Ser Trp Leu Val Lys Leu Leu Glu Lys
        35                  40                  45

Gly Tyr Thr Val Lys Gly Thr Val Arg Asn Pro Asp Asp Pro Lys Asn
50                  55                  60

Ala His Leu Lys Ala Leu Asp Gly Ala Ala Glu Arg Leu Ile Leu Cys
65                  70                  75                  80

Lys Ala Asp Leu Leu Asp Tyr Asp Ala Ile Cys Arg Ala Val Glu Gly
                85                  90                  95

Cys His Gly Val Phe His Thr Ala Ser Pro Val Thr Asp Asp Pro Glu
                100                 105                 110

Gln Met Val Glu Pro Ala Val Arg Gly Thr Glu Tyr Val Ile Arg Ala
            115                 120                 125

Ala Ala Glu Ala Gly Thr Val Arg Arg Val Val Phe Thr Ser Ser Ile
        130                 135                 140

Gly Ala Val Thr Met Asp Pro Asn Arg Gly Pro Asp Val Val Val Asp
145                 150                 155                 160

Glu Ser Cys Trp Ser Asp Leu Asp Phe Cys Lys Lys Thr Arg Asn Trp
                165                 170                 175

Tyr Cys Tyr Gly Lys Ala Val Ala Glu Gln Ala Ala Trp Asp Ala Ala
            180                 185                 190

Arg Gln Arg Gly Val Asp Leu Val Val Val Asn Pro Val Leu Val Val
        195                 200                 205

Gly Pro Leu Leu Gln Pro Thr Val Asn Ala Ser Ile Ala His Ile Leu
210                 215                 220

Lys Tyr Leu Asp Gly Ser Ala Arg Thr Phe Ala Asn Ala Val Gln Ala
225                 230                 235                 240

Tyr Val Asp Val Arg Asp Val Ala Ala Ala His Leu Leu Val Phe Glu
            245                 250                 255

Ala Pro Ala Ala Ser Gly Arg His Leu Cys Ala Asp Arg Val Leu His
        260                 265                 270

Arg Glu Asp Val Val Arg Ile Leu Ala Lys Leu Phe Pro Glu Tyr Pro
        275                 280                 285

Val Pro Thr Arg Cys Ser Asp Glu Val Asn Pro Arg Lys Gln Ala Tyr
290                 295                 300

Lys Phe Ser Asn Gln Lys Leu Arg Asp Leu Gly Leu Glu Phe Arg Pro
305                 310                 315                 320

Val Ser Gln Ser Leu Tyr Asp Thr Val Lys Ser Leu Gln Glu Lys Gly
            325                 330                 335

His Leu Pro Val Leu Ala Glu Gln Ala Pro Glu Ala Ala Pro Gly Ala
        340                 345                 350

Glu Ala Gln Gln Gly Gly Ile Ala Ile Arg Ala
        355                 360

<210> SEQ ID NO 38
<211> LENGTH: 369
<212> TYPE: PRT
<213> ORGANISM: Cenchrus purpureus

<400> SEQUENCE: 38

Met Thr Val Val Asp Ala Val Ser Ala Asp Ala Asp Ala Pro Ala Ala
1               5                   10                  15

Ala Thr Val Val Ala Pro Val Gly Asn Gly Gln Thr Val Cys Val Thr
            20                  25                  30

Gly Ala Ala Gly Tyr Ile Ala Ser Trp Leu Val Lys Leu Leu Leu Glu
        35                  40                  45

Lys Gly Tyr Thr Val Lys Gly Thr Val Arg Asn Pro Asp Asp Pro Lys
    50                  55                  60

Asn Ala His Leu Lys Ala Leu Asp Gly Ala Ala Glu Arg Leu Ile Leu
65                  70                  75                  80

Cys Lys Ala Asp Leu Leu Asp Tyr Asp Ala Ile Arg Arg Ala Val Gln
                85                  90                  95

Gly Cys Gln Gly Val Phe His Thr Ala Ser Pro Val Thr Asp Asp Pro
                100                 105                 110

```
Glu Gln Met Val Glu Pro Ala Val Arg Gly Thr Glu Tyr Val Leu Ser
            115                 120                 125

Ala Ala Ala Glu Ala Gly Thr Val Arg Arg Val Val Phe Thr Ser Ser
        130                 135                 140

Ile Gly Ala Val Thr Met Asp Pro Asn Arg Gly Pro Asp Val Val Val
145                 150                 155                 160

Asp Glu Ser Cys Trp Ser Asp Leu Asp Phe Cys Lys Lys Thr Arg Asn
                165                 170                 175

Trp Tyr Cys Tyr Gly Lys Ala Val Ala Glu Gln Ser Ala Trp Asp Ala
            180                 185                 190

Ala Arg Gln Arg Gly Val Asp Leu Val Val Asn Pro Val Leu Val
            195                 200                 205

Val Gly Pro Leu Leu Gln Pro Thr Val Asn Ala Ser Ile Ala His Ile
        210                 215                 220

Leu Lys Tyr Leu Asp Gly Ser Ala Arg Thr Phe Ala Asn Ala Val Gln
225                 230                 235                 240

Ala Tyr Val Asp Val Arg Asp Val Ala Ala His Leu Ala Val Phe
                245                 250                 255

Glu Ser Ala Ala Ala Ser Gly Arg His Leu Cys Ala Glu Arg Val Leu
                260                 265                 270

His Arg Glu Asp Val Val Arg Ile Leu Ala Lys Leu Phe Pro Glu Tyr
            275                 280                 285

Pro Val Pro Thr Arg Cys Ser Asp Glu Lys Asn Pro Arg Lys Gln Pro
        290                 295                 300

Tyr Lys Phe Thr Asn Gln Lys Leu Arg Asp Leu Gly Met Glu Phe Arg
305                 310                 315                 320

Pro Val Ser Gln Ser Leu Tyr Asp Thr Val Lys Ser Leu Gln Glu Lys
                325                 330                 335

Gly His Leu Pro Val Leu Gly Asp Gly Glu Gln Thr Pro Glu Gly Glu
            340                 345                 350

Lys Lys Asp Ala Ala Ala Glu Val Gln Gln Gly Gly Ile Ala Ile Arg
            355                 360                 365

Ala

<210> SEQ ID NO 39
<211> LENGTH: 329
<212> TYPE: PRT
<213> ORGANISM: Camellia oleifera

<400> SEQUENCE: 39

Met Ser Ser Asn Thr Lys Ala Gly Gly Asp Gly Gln Val Val Cys Val
1               5                   10                  15

Thr Gly Gly Ser Gly Phe Ile Gly Ser Trp Leu Val Arg Leu Leu Leu
            20                  25                  30

Asp Arg Gly Tyr Thr Val His Ala Thr Val Lys Asp Leu Lys Asp Glu
        35                  40                  45

Lys Glu Thr Lys His Leu Glu Ala Leu Glu Gly Ala Glu Ser Arg Leu
    50                  55                  60

Arg Leu Phe Gln Ile Asp Leu Leu Asp Tyr Asp Ser Ile Val Ala Ala
65                  70                  75                  80

Val Thr Gly Ser Ser Gly Val Phe His Leu Ala Ser Pro Cys Ile Val
                85                  90                  95

Asp Gln Val Lys Asp Pro Glu Arg Glu Leu Leu Glu Pro Ala Ile Lys
            100                 105                 110
```

```
Gly Thr Leu Asn Val Leu Thr Ala Ala Lys Glu Leu Gly Val Arg Arg
            115                 120                 125

Val Val Val Thr Ser Ser Asn Thr Ala Ile Thr Pro Ser Pro Asn Trp
        130                 135                 140

Pro Ala Asp Lys Val Lys Asn Glu Asp Cys Trp Thr Asp Val Glu Tyr
145                 150                 155                 160

Cys Lys Gln Asn Gly Leu Trp Tyr Pro Leu Ser Lys Thr Leu Ala Glu
                165                 170                 175

Lys Ala Ala Trp Glu Phe Ala Lys Glu Lys Gly Leu Asp Val Val Val
                180                 185                 190

Val Asn Pro Gly Thr Val Met Gly Pro Ile Ile Pro Ala Leu Asn
                195                 200                 205

Ala Ser Met Leu Met Leu Leu Arg Phe Leu Gln Gly Cys Thr Glu Ile
        210                 215                 220

Tyr Glu Asn Phe Phe Met Gly Pro Val His Val Lys Asp Val Ala Leu
225                 230                 235                 240

Ala His Ile Leu Val Tyr Glu Asn Thr Ser Ala Thr Gly Arg His Leu
                245                 250                 255

Cys Val Glu Ala Ile Ser His Tyr Gly Asp Phe Thr Ala Met Val Ala
                260                 265                 270

Glu Leu Tyr Pro Glu Tyr Asn Val Pro Arg Leu Pro Lys Asp Thr Gln
        275                 280                 285

Pro Gly Leu Leu Arg Thr Lys Asp Gly Ser Lys Leu Met Asp Leu
        290                 295                 300

Gly Phe Gln Phe Ile Pro Met Glu Gln Ile Ile Lys Glu Thr Val Glu
305                 310                 315                 320

Ser Leu Lys Ser Lys Gly Tyr Ile Ser
                325

<210> SEQ ID NO 40
<211> LENGTH: 319
<212> TYPE: PRT
<213> ORGANISM: Acacia auriculiformis x Acacia mangium

<400> SEQUENCE: 40

Met Ser Lys Val Val Cys Val Thr Gly Ala Ser Gly Ala Ile Gly Ser
1               5                   10                  15

Trp Leu Val Arg Leu Leu Asp Arg Gly Tyr Thr Ile His Ala Thr
                20                  25                  30

Val Gln Asn Leu Lys Asp Glu Asn Glu Thr Lys His Leu Glu Val Met
            35                  40                  45

Glu Gly Ala Lys Ser Arg Leu Arg Leu Phe Glu Met Asp Leu Leu Asp
        50                  55                  60

Glu Asp Ser Ile Met Ala Thr Val Lys Gly Cys Ala Gly Val Phe His
65                  70                  75                  80

Leu Ala Cys Pro Asn Val Ile Gly Gln Val Gln Asp Pro Glu Lys Glu
                85                  90                  95

Ile Val Glu Pro Ala Val Lys Gly Thr Val Asn Val Leu Lys Ala Ala
                100                 105                 110

Arg Glu Ala Gly Val Glu Arg Val Val Ala Thr Ser Ser Ile Ser Ala
                115                 120                 125

Ile Ile Pro Ser Pro Asn Trp Pro Ser Asp Arg Ile Lys Asn Glu Asp
            130                 135                 140

Cys Trp Cys Asp Leu Asp Tyr Cys Lys Arg Lys Gly Leu Trp Tyr Pro
```

```
            145                 150                 155                 160
        Ile Ala Lys Thr Leu Ala Glu Lys Ala Gly Trp Glu Phe Ala Lys Glu
                        165                 170                 175

Thr Gly Tyr Asp Val Val Met Ile Asn Pro Gly Thr Ala Leu Gly Pro
                        180                 185                 190

Leu Ile Pro Pro Arg Leu Asn Ser Met Ala Val Leu Leu Gly Val
                        195                 200                 205

Leu Lys Gly Asp Thr Glu Thr Tyr Glu Asp Phe Phe Met Gly Met Ala
                210                 215                 220

His Phe Lys Asp Val Ala Met Ala His Ile Leu Ala Phe Glu Lys Lys
        225                 230                 235                 240

Glu Ala Ser Gly Arg Asn Leu Cys Val Glu Ala Ile Arg His Tyr Gly
                        245                 250                 255

Asp Phe Val Glu Lys Val Ala Glu Leu Tyr Pro Gln Tyr His Val Ala
                        260                 265                 270

Lys Val Pro Lys Asp Thr Gln Pro Gly Leu Leu Arg Ala Thr Asp Ala
                        275                 280                 285

Ser Lys Lys Leu Ile Asn Leu Gly Met Lys Phe Thr Pro Ile Glu Gln
                290                 295                 300

Ile Ile Thr Asp Ala Val Glu Ser Leu Lys Ser Leu Gly Phe Leu
        305                 310                 315

<210> SEQ ID NO 41
<211> LENGTH: 320
<212> TYPE: PRT
<213> ORGANISM: Jatropha curcas

<400> SEQUENCE: 41

Met Pro Glu Tyr Cys Val Thr Gly Gly Thr Gly Phe Ile Ala Ala Tyr
        1               5                   10                  15

Leu Ile Lys Ser Leu Leu Asp Lys Gly His Thr Val Arg Ala Thr Val
                        20                  25                  30

Arg Asp Pro Gly Asp Ser Glu Lys Val Gly Phe Leu Arg Glu Phe Asn
                        35                  40                  45

Gly Ala Lys Glu Arg Leu Lys Ile Leu Lys Ala Asp Leu Leu Val Glu
                50                  55                  60

Gly Ser Phe Asp Glu Ala Ile Gln Gly Val Asp Gly Val Phe His Thr
        65                  70                  75                  80

Ala Ser Pro Val Ile Val Ser Tyr Asp Asp Asn Val Gln Ala Thr Leu
                        85                  90                  95

Ile Asp Pro Cys Ile Lys Gly Thr Leu Asn Val Leu Ser Ser Cys Thr
                        100                 105                 110

Lys Ala Thr Ser Val Lys Arg Val Val Leu Thr Ser Ser Cys Ser Ser
                        115                 120                 125

Ile Arg Tyr Arg Tyr Asp Val Gln Gln Val Cys Pro Leu Asn Glu Ser
                130                 135                 140

His Trp Ser Asp Thr Asp Tyr Cys Lys Arg Tyr Asn Leu Trp Tyr Ala
        145                 150                 155                 160

Tyr Ala Lys Thr Ile Gly Glu Thr Glu Ala Trp Arg Ile Ala Lys Glu
                        165                 170                 175

Ser Gly Ile Asp Leu Val Val Val Asn Pro Ser Phe Val Val Gly Pro
                        180                 185                 190

Leu Leu Ala Pro Gln Pro Thr Ser Thr Leu His Leu Ile Leu Ser Ile
                        195                 200                 205
```

```
Val Lys Gly Ser Leu Gly Gln Tyr Pro Asn Thr Thr Val Gly Phe Val
210                 215                 220

His Ile Asp Asp Val Ile Ala Ala His Ile Leu Ala Met Glu Asp Ser
225                 230                 235                 240

Arg Ala Ser Gly Arg Leu Val Cys Ser Ser Val Ala His Trp Ser
                245                 250                 255

Glu Ile Ile Glu Met Leu Arg Ala Lys Tyr Pro Ser Tyr Pro Tyr Glu
                260                 265                 270

Asn Lys Cys Ser Ser Gln Glu Gly Asp Asn Pro His Ser Met Asp
                275                 280                 285

Thr Thr Lys Ile Thr Gln Leu Gly Phe Pro Pro Phe Arg Thr Leu Glu
290                 295                 300

Gln Met Phe Asp Asp Cys Ile Lys Ser Phe Gln Asp Lys Gly Phe Leu
305                 310                 315                 320
```

```
<210> SEQ ID NO 42
<211> LENGTH: 38
<212> TYPE: DNA
<213> ORGANISM: Artificial Sequence
<220> FEATURE:
<223> OTHER INFORMATION: ccr2 line

<400> SEQUENCE: 42
gcagtgaacg ggaccaaaaa tgtgatcatt tgcggcgg                           38

<210> SEQ ID NO 43
<211> LENGTH: 28
<212> TYPE: DNA
<213> ORGANISM: Artificial Sequence
<220> FEATURE:
<223> OTHER INFORMATION: ccr2 line

<400> SEQUENCE: 43
gcagtgaacg ggaccaaaaa tgtgatca                                      28

<210> SEQ ID NO 44
<211> LENGTH: 36
<212> TYPE: DNA
<213> ORGANISM: Artificial Sequence
<220> FEATURE:
<223> OTHER INFORMATION: ccr2 line

<400> SEQUENCE: 44
gcagtgaacg ggaccaaaaa tgtgatcttg cggcgg                             36

<210> SEQ ID NO 45
<211> LENGTH: 30
<212> TYPE: DNA
<213> ORGANISM: Artificial Sequence
<220> FEATURE:
<223> OTHER INFORMATION: ccr2 line

<400> SEQUENCE: 45
gcagtgaacg ggaccaaaaa tgtgatgcgg                                    30

<210> SEQ ID NO 46
<211> LENGTH: 38
<212> TYPE: DNA
<213> ORGANISM: Artificial Sequence
<220> FEATURE:
<223> OTHER INFORMATION: ccr2 line

<400> SEQUENCE: 46
```

```
gcagtgaacg ggaccaaaaa tgtgatcaat tgcggcgg                          38

<210> SEQ ID NO 47
<211> LENGTH: 38
<212> TYPE: DNA
<213> ORGANISM: Artificial Sequence
<220> FEATURE:
<223> OTHER INFORMATION: ccr2 line

<400> SEQUENCE: 47
gcagtgaacg ggaccaaaaa tgtgatcaat tgcggcgg                          38

<210> SEQ ID NO 48
<211> LENGTH: 38
<212> TYPE: DNA
<213> ORGANISM: Artificial Sequence
<220> FEATURE:
<223> OTHER INFORMATION: ccr2 line

<400> SEQUENCE: 48
gcagtgaacg ggaccaaaaa tgtgatcaat tgcggcgg                          38

<210> SEQ ID NO 49
<211> LENGTH: 21
<212> TYPE: DNA
<213> ORGANISM: Artificial Sequence
<220> FEATURE:
<223> OTHER INFORMATION: ccr2 line

<400> SEQUENCE: 49
gcagtgaacg ggaccaaaaa t                                            21

<210> SEQ ID NO 50
<211> LENGTH: 38
<212> TYPE: DNA
<213> ORGANISM: Artificial Sequence
<220> FEATURE:
<223> OTHER INFORMATION: ccr2 line

<400> SEQUENCE: 50
gcagtgaacg ggaccaaaaa tgtgatcaat tgcggcgg                          38

<210> SEQ ID NO 51
<211> LENGTH: 36
<212> TYPE: DNA
<213> ORGANISM: Artificial Sequence
<220> FEATURE:
<223> OTHER INFORMATION: ccr2 line

<400> SEQUENCE: 51
gcagtgaacg ggaccaaaaa tgtgatcttg cggcgg                            36

<210> SEQ ID NO 52
<211> LENGTH: 38
<212> TYPE: DNA
<213> ORGANISM: Artificial Sequence
<220> FEATURE:
<223> OTHER INFORMATION: ccr2 line

<400> SEQUENCE: 52
gcagtgaacg ggaccaaaaa tgtgatcaat tgcggcgg                          38

<210> SEQ ID NO 53
<211> LENGTH: 36
<212> TYPE: DNA
<213> ORGANISM: Artificial Sequence
```

```
<220> FEATURE:
<223> OTHER INFORMATION: ccr2 line

<400> SEQUENCE: 53
gcagtgaacg ggaccaaaaa tgtgatcttg cggcgg                                    36

<210> SEQ ID NO 54
<211> LENGTH: 38
<212> TYPE: DNA
<213> ORGANISM: Artificial Sequence
<220> FEATURE:
<223> OTHER INFORMATION: ccr2 line

<400> SEQUENCE: 54
gcagtgaacg ggaccaaaaa tgtgatcact tgcggcgg                                  38

<210> SEQ ID NO 55
<211> LENGTH: 29
<212> TYPE: DNA
<213> ORGANISM: Artificial Sequence
<220> FEATURE:
<223> OTHER INFORMATION: ccr2 line

<400> SEQUENCE: 55
gcagtgaacg ggaccaaaaa ttgcggcgg                                            29

<210> SEQ ID NO 56
<211> LENGTH: 38
<212> TYPE: DNA
<213> ORGANISM: Artificial Sequence
<220> FEATURE:
<223> OTHER INFORMATION: ccr2 line

<400> SEQUENCE: 56
gcagtgaacg ggaccaaaaa tgtgatcaat tgcggcgg                                  38

<210> SEQ ID NO 57
<211> LENGTH: 34
<212> TYPE: DNA
<213> ORGANISM: Artificial Sequence
<220> FEATURE:
<223> OTHER INFORMATION: ccr2 line

<400> SEQUENCE: 57
gcagtgaacg ggaccaaaaa tgtgatcacg gcgg                                      34

<210> SEQ ID NO 58
<211> LENGTH: 37
<212> TYPE: DNA
<213> ORGANISM: Populus tremula x Populus alba

<400> SEQUENCE: 58
gcagtgaacg ggaccaaaaa tgtgatcatt gcggcgg                                   37

<210> SEQ ID NO 59
<211> LENGTH: 37
<212> TYPE: DNA
<213> ORGANISM: Populus tremula x Populus alba

<400> SEQUENCE: 59
gcagtgaacg ggaccaaaaa tgtgatcatt gcggcgg                                   37

<210> SEQ ID NO 60
<211> LENGTH: 8
<212> TYPE: PRT
```

```
<213> ORGANISM: Artificial Sequence
<220> FEATURE:
<223> OTHER INFORMATION: cofactor binding motif
<220> FEATURE:
<221> NAME/KEY: MISC_FEATURE
<222> LOCATION: (3)..(4)
<223> OTHER INFORMATION: X can be any amino acid
<220> FEATURE:
<221> NAME/KEY: MISC_FEATURE
<222> LOCATION: (6)..(7)
<223> OTHER INFORMATION: X can be any amino acid

<400> SEQUENCE: 60

Thr Gly Xaa Xaa Gly Xaa Xaa Gly
1               5

<210> SEQ ID NO 61
<211> LENGTH: 9
<212> TYPE: PRT
<213> ORGANISM: Artificial Sequence
<220> FEATURE:
<223> OTHER INFORMATION: cofactor binding motif
<220> FEATURE:
<221> NAME/KEY: MISC_FEATURE
<222> LOCATION: (3)..(5)
<223> OTHER INFORMATION: X can be any amino acid
<220> FEATURE:
<221> NAME/KEY: MISC_FEATURE
<222> LOCATION: (8)..(8)
<223> OTHER INFORMATION: X can be any amino acid

<400> SEQUENCE: 61

Thr Gly Xaa Xaa Xaa Ala Gly Xaa Gly
1               5

<210> SEQ ID NO 62
<211> LENGTH: 7
<212> TYPE: PRT
<213> ORGANISM: Artificial Sequence
<220> FEATURE:
<223> OTHER INFORMATION: cofactor binding motif
<220> FEATURE:
<221> NAME/KEY: MISC_FEATURE
<222> LOCATION: (3)..(6)
<223> OTHER INFORMATION: X can be any amino acid

<400> SEQUENCE: 62

Thr Gly Xaa Xaa Xaa Xaa Gly
1               5

<210> SEQ ID NO 63
<211> LENGTH: 5
<212> TYPE: PRT
<213> ORGANISM: Artificial Sequence
<220> FEATURE:
<223> OTHER INFORMATION: active site motif
<220> FEATURE:
<221> NAME/KEY: MISC_FEATURE
<222> LOCATION: (2)..(4)
<223> OTHER INFORMATION: X can be any amino acid

<400> SEQUENCE: 63

Tyr Xaa Xaa Xaa Lys
1               5

<210> SEQ ID NO 64
<211> LENGTH: 23
<212> TYPE: DNA
<213> ORGANISM: Artificial Sequence
<220> FEATURE:
<223> OTHER INFORMATION: protospacer
```

```
<400> SEQUENCE: 64
gaaaaatgtg atcattgcgg cgg                                              23

<210> SEQ ID NO 65
<211> LENGTH: 7
<212> TYPE: PRT
<213> ORGANISM: Artificial Sequence
<220> FEATURE:
<223> OTHER INFORMATION: Signatural CCR sequence

<400> SEQUENCE: 65

Asn Trp Tyr Cys Tyr Gly Lys
1               5

<210> SEQ ID NO 66
<211> LENGTH: 20
<212> TYPE: DNA
<213> ORGANISM: Artificial Sequence
<220> FEATURE:
<223> OTHER INFORMATION: protospacer

<400> SEQUENCE: 66
ggaacaagct gcatgggata                                                  20

<210> SEQ ID NO 67
<211> LENGTH: 20
<212> TYPE: DNA
<213> ORGANISM: Artificial Sequence
<220> FEATURE:
<223> OTHER INFORMATION: protospacer

<400> SEQUENCE: 67
gtggtattgc tatggaaagg                                                  20

<210> SEQ ID NO 68
<211> LENGTH: 67
<212> TYPE: DNA
<213> ORGANISM: Populus alba

<400> SEQUENCE: 68
cagaattggt attgctatgg aaaggcggtg gcagaacaag ctgcgtggga tatggctaag      60
gagaaag                                                                67

<210> SEQ ID NO 69
<211> LENGTH: 67
<212> TYPE: DNA
<213> ORGANISM: Populus tremula

<400> SEQUENCE: 69
cagaattggt attgctatgg aaaggctgtg gcagaacaag ctgcatggga tatggctaag      60
gagaaag                                                                67

<210> SEQ ID NO 70
<211> LENGTH: 62
<212> TYPE: DNA
<213> ORGANISM: Populus alba

<400> SEQUENCE: 70
cagaattggt attgctatgg cggtggcaga acaagctgcg tgggatatgg ctaaggagaa      60
ag                                                                     62
```

```
<210> SEQ ID NO 71
<211> LENGTH: 60
<212> TYPE: DNA
<213> ORGANISM: Populus alba

<400> SEQUENCE: 71
cagaattggt attgcaggcg gtggcagaac aagctgcgtg ggatatggct aaggagaaag      60

<210> SEQ ID NO 72
<211> LENGTH: 60
<212> TYPE: DNA
<213> ORGANISM: Populus alba

<400> SEQUENCE: 72
cagaattggt attgcaggcg gtggcagaac aagctgcgtg ggatatggct aaggagaaag      60

<210> SEQ ID NO 73
<211> LENGTH: 66
<212> TYPE: DNA
<213> ORGANISM: Populus alba

<400> SEQUENCE: 73
cagaattggt attgctatgg aaggcggtgg cagaacaagc tgcgtgggat atggctaagg      60
agaaag                                                                66

<210> SEQ ID NO 74
<211> LENGTH: 63
<212> TYPE: DNA
<213> ORGANISM: Populus alba

<400> SEQUENCE: 74
cagaattggt attgctaaag gcggtggcag aacaagctgc gtgggatatg gctaaggaga      60
aag                                                                   63

<210> SEQ ID NO 75
<211> LENGTH: 59
<212> TYPE: DNA
<213> ORGANISM: Populus alba

<400> SEQUENCE: 75
cagaattggt attgctatgg agaaagcaca agctgcgtgg gatatggcta aggagaaag       59

<210> SEQ ID NO 76
<211> LENGTH: 68
<212> TYPE: DNA
<213> ORGANISM: Populus alba

<400> SEQUENCE: 76
cagaattggt attgctatgg aaaggcggt ggcagaacaa gctgcgtggg atatggctaa       60
ggagaaag                                                              68

<210> SEQ ID NO 77
<211> LENGTH: 70
<212> TYPE: DNA
<213> ORGANISM: Populus alba

<400> SEQUENCE: 77
ggcagaacaa gctgcgtggg atatggctaa ggagaaaggg gtggacctag tggtggttaa      60
cccagtgctg                                                            70

<210> SEQ ID NO 78
```

```
<211> LENGTH: 70
<212> TYPE: DNA
<213> ORGANISM: Populus tremula

<400> SEQUENCE: 78
ggcagaacaa gctgcatggg atatggctaa ggagaaaggg gtggacctag tggtggttaa      60
cccagtgctg                                                             70

<210> SEQ ID NO 79
<211> LENGTH: 66
<212> TYPE: DNA
<213> ORGANISM: Populus tremula

<400> SEQUENCE: 79
ggcagaacaa gctgcgatat ggctaaggag aaaggggtgg acctagtggt ggttaaccca      60
gtgctg                                                                 66

<210> SEQ ID NO 80
<211> LENGTH: 71
<212> TYPE: DNA
<213> ORGANISM: Populus tremula

<400> SEQUENCE: 80
ggcagaacaa gctgcatggg aatatggcta aggagaaagg ggtggaccta gtggtggtta      60
acccagtgct g                                                           71

<210> SEQ ID NO 81
<211> LENGTH: 65
<212> TYPE: DNA
<213> ORGANISM: Populus tremula

<400> SEQUENCE: 81
ggcagaacaa gctgcatatg gctaaggaga aaggggtgga cctagtggtg gttaacccag      60
tgctg                                                                  65

<210> SEQ ID NO 82
<211> LENGTH: 18
<212> TYPE: DNA
<213> ORGANISM: Populus tremula

<400> SEQUENCE: 82
ggcagaacaa gctgcatg                                                    18

<210> SEQ ID NO 83
<211> LENGTH: 68
<212> TYPE: DNA
<213> ORGANISM: Populus tremula

<400> SEQUENCE: 83
ggcagaacaa gctgcatgat atggctaagg agaaagggt ggacctagtg gtggttaacc       60
cagtgctg                                                               68

<210> SEQ ID NO 84
<211> LENGTH: 71
<212> TYPE: DNA
<213> ORGANISM: Populus tremula

<400> SEQUENCE: 84
ggcagaacaa gctgcatggg aatatggcta aggagaaagg ggtggaccta gtggtggtta      60
acccagtgct g                                                           71
```

```
<210> SEQ ID NO 85
<211> LENGTH: 71
<212> TYPE: DNA
<213> ORGANISM: Populus tremula

<400> SEQUENCE: 85
ggcagaacaa gctgcatggg aatatggcta aggagaaagg ggtggaccta gtggtggtta      60
acccagtgct g                                                          71

<210> SEQ ID NO 86
<211> LENGTH: 67
<212> TYPE: DNA
<213> ORGANISM: Populus alba

<400> SEQUENCE: 86
ggcggtggca gaacaagctg cgtgggatat ggctaaggag aaaggggtgg acctagtggt      60
ggttaac                                                               67

<210> SEQ ID NO 87
<211> LENGTH: 67
<212> TYPE: DNA
<213> ORGANISM: Populus tremula

<400> SEQUENCE: 87
ggctgtggca gaacaagctg catgggatat ggctaaggag aaaggggtgg acctagtggt      60
ggttaac                                                               67

<210> SEQ ID NO 88
<211> LENGTH: 62
<212> TYPE: DNA
<213> ORGANISM: Populus alba

<400> SEQUENCE: 88
ggcggtggca gaacaagctg catatggcta aggagaaagg ggtggaccta gtggtggtta      60
ac                                                                    62

<210> SEQ ID NO 89
<211> LENGTH: 68
<212> TYPE: DNA
<213> ORGANISM: Populus tremula

<400> SEQUENCE: 89
ggctgtggca gaacaagctg catgggaata tggctaagga gaaaggggtg gacctagtgg      60
tggttaac                                                              68

<210> SEQ ID NO 90
<211> LENGTH: 68
<212> TYPE: DNA
<213> ORGANISM: Populus alba

<400> SEQUENCE: 90
gaaatggtgg agccagcagt gaacgggacc aaaaatgtga tcattgcggc ggctgaggcc      60
aaagtccg                                                              68

<210> SEQ ID NO 91
<211> LENGTH: 64
<212> TYPE: DNA
<213> ORGANISM: Populus tremula x Populus alba
```

<400> SEQUENCE: 91
gaaatggtgg agccagcagt gaacgggacc aaaaatgtga tgcggcggct gaggccaaag    60
tccg                                                                 64

<210> SEQ ID NO 92
<211> LENGTH: 65
<212> TYPE: DNA
<213> ORGANISM: Populus tremula x Populus alba

<400> SEQUENCE: 92
gaaatggtgg agccagcagt gaacgggacc aaaaatgtga ttgcggcggc tgaggccaaa    60
gtccg                                                                65

<210> SEQ ID NO 93
<211> LENGTH: 337
<212> TYPE: PRT
<213> ORGANISM: Populus tremula

<400> SEQUENCE: 93

Met Pro Val Asp Ala Ser Ser Leu Ser Gly Gln Gly Gln Thr Ile Cys
1               5                   10                  15

Val Thr Gly Ala Gly Gly Phe Ile Ala Ser Trp Met Val Lys Leu Leu
            20                  25                  30

Leu Asp Lys Gly Tyr Thr Val Arg Gly Thr Ala Arg Asn Pro Ala Asp
        35                  40                  45

Pro Lys Asn Ser His Leu Arg Glu Leu Glu Gly Ala Gln Glu Arg Leu
    50                  55                  60

Thr Leu Cys Lys Ala Asp Leu Leu Asp Tyr Glu Ser Leu Lys Glu Ala
65                  70                  75                  80

Ile Gln Gly Cys Asp Gly Val Phe His Thr Ala Ser Pro Val Thr Asp
                85                  90                  95

Asp Pro Glu Glu Met Val Glu Pro Ala Val Asn Gly Thr Lys Asn Val
            100                 105                 110

Ile Ala Ala Ala Glu Ala Lys Val Arg Arg Val Val Phe Thr Ser Ser
        115                 120                 125

Ile Gly Ala Val Tyr Met Asp Pro Asn Lys Gly Pro Asp Val Val Ile
    130                 135                 140

Asp Glu Ser Cys Trp Ser Asp Leu Glu Phe Cys Lys Asn Thr Lys Asn
145                 150                 155                 160

Trp Tyr Cys Tyr Gly Lys Ala Val Ala Glu Gln Ala Ala Trp Asp Met
                165                 170                 175

Ala Lys Glu Lys Gly Val Asp Leu Val Val Val Asn Pro Val Leu Val
            180                 185                 190

Leu Gly Pro Leu Leu Gln Pro Thr Val Asn Ala Ser Ile Val His Ile
        195                 200                 205

Leu Lys Tyr Leu Thr Gly Ser Ala Lys Thr Tyr Ala Asn Ser Val Gln
    210                 215                 220

Ala Tyr Val His Val Arg Asp Val Ala Leu Ala His Ile Leu Val Phe
225                 230                 235                 240

Glu Thr Pro Ser Ala Ser Gly Arg Tyr Leu Cys Ser Glu Ser Val Leu
                245                 250                 255

His Arg Gly Glu Val Val Glu Ile Leu Ala Lys Phe Phe Pro Glu Tyr
            260                 265                 270

Pro Ile Pro Thr Lys Cys Ser Asp Glu Lys Asn Pro Arg Lys Gln Pro
        275                 280                 285

-continued

```
Tyr Lys Phe Ser Asn Gln Lys Leu Arg Asp Leu Gly Phe Glu Phe Thr
    290                 295                 300

Pro Val Lys Gln Cys Leu Tyr Glu Thr Val Lys Ser Leu Gln Glu Arg
305                 310                 315                 320

Gly His Leu Pro Ile Pro Lys Gln Ala Ala Glu Glu Ser Val Lys Ile
                325                 330                 335

Gln
```